(12) United States Patent
Binggeli et al.

(10) Patent No.: US 7,772,253 B2
(45) Date of Patent: Aug. 10, 2010

(54) AMIDE DERIVATIVES AS SOMATOSTATIN RECEPTOR 5 ANTAGONISTS

(75) Inventors: Alfred Binggeli, Binningen (CH); Andreas Christ, Arlesheim (CH); Luke Gideon Granville Green, Basel (CH); Wolfgang Guba, Muellheim (DE); Hans-Peter Maerki, Basel (CH); Rainer Eugen Martin, Basel (CH); Peter Mohr, Basel (CH)

(73) Assignee: Hoffman-La Roche Inc., Nutley, NJ (US)

( * ) Notice: Subject to any disclaimer, the term of this patent is extended or adjusted under 35 U.S.C. 154(b) by 1016 days.

(21) Appl. No.: 11/442,619

(22) Filed: May 26, 2006

(65) Prior Publication Data

US 2006/0276508 A1 Dec. 7, 2006

(30) Foreign Application Priority Data

Jun. 2, 2005 (EP) .................................. 05104774

(51) Int. Cl.
*A61K 31/4545* (2006.01)
*C07D 403/02* (2006.01)
(52) U.S. Cl. ...................... 514/317; 514/318; 514/323; 514/326; 546/194; 546/201; 546/209; 546/225
(58) Field of Classification Search ................. 514/317, 514/318, 323, 326; 546/194, 201, 209, 225
See application file for complete search history.

(56) References Cited

U.S. PATENT DOCUMENTS

| 5,098,915 A * | 3/1992 | Desai et al. ................... 514/324 |
| 2004/0006089 A1 | 1/2004 | Thurieau et al. |
| 2005/0096337 A1 | 5/2005 | Ackermann et al. |

FOREIGN PATENT DOCUMENTS

| CH | 628 885 | 3/1982 |
| DE | 2435934 | 2/1975 |
| WO | WO 9905123 | 2/1999 |
| WO | WO 00/66558 A1 | 11/2000 |
| WO | WO 2004/110995 | 12/2004 |

OTHER PUBLICATIONS

Benmehdi et al. "synthesis of new trisubstituted . . ." CA 149:490369 (2008).*
Boren et al. "Pyrazole . . . " CA 149:79594 (2008).*
Belanger et al. "Preparation of pyridines . . . " CA 149:153074 (2008).*
Crider "Somatostatin receptor . . . " Exp. Opionion ther. Patents 13(9) p. 1427-1441 (2003).*
Martin et al. Discovery of the first . . . J. Med. Chem. v. 50(5) p. 6291-6294 (2007).*
Joslin's Diabetes Mellitus 13th Ed. (Eds. C. R. Kahn, G. C. Weir), Lea & Febiger, Malvern, PA, pp. 240-264, (1994).

H. E. Lebovitz, 1994, Oral antidiabetic agents. Joslin's Diabetes Mellitus 13th Ed. (Eds. C. R. Kahn, G. C. Weir), Lea & Febiger, Malvern, PA, pp. 508-529.
C. J. Bailey, R. C. Turner *New Engl. J. Med.*, 1996, 574-579.
G. L. Plosker, D. Faulds *Drugs*, 1999, 57, 409-438.
Y. Zambre, et al., *Biochem. Pharmacol.*, 1999, 57, 1159-1164.
S. P. Fagan, et. al., *Surgery* 1998, 124, 254-258.
M. Norman, et. al., *Ann. Surg.* 2002, 235, 767-774.
T.A. Tirone, et. al., *Pancreas* 2003, 26, e67-73.
M. Z. Strowski, et. al., *Mol. Endocrinol.* 2003, 17, 93-106.
K. Cejvan, D. H. Coy, S. Efendic *Diabetes* 2003, 52, 1176-1181.
M. Z. Strowski, et. al., *Endocrinology* 2000, 141, 111-117.
E. Náslund, et. al., *Int. J. Obes.* 1999, 23, 304-311.
J.-P. Gutzwiller, et. al., *Gut* 1999, 44, 81-88.
J.-P. Gutzwiller, et al., *Am. J. Physiol.* 1999, 276, R1541-1544.
M. D. Turton, et al., *Nature* 1996, 69-72.
A. Flint, et al., *J. Clin. Invest.* 1998, 101, 515-520.
M. B. Toft-Nielsen, et al., *Diabetes Care* 1999, 22, 1137-1143.
L. Hansen, et al., *Am. J. Phys.* 2000, 278, E1010-1018.
D. G. Burrin, et al., *Domest. Anim. Endocrinol.* 2003, 24, 103-122.
K. V. Haderslev, et al., *Scand. J. Gastroenterol.* 2002, 37, 392-398.
P. B. Jeppesen *J. Nutr.* 2003, 133, 3721-3724.
T. Talme, et al, *Clin. Exp. Immunol.* 2001, 125, 71-79.
D. Ferone, et al., *Dig. Liver Dis.* 2004, 36, S68-77.
C. E. Ghamrawy, et al., *Peptides* 1999, 20, 305-311.
*J. Org. Chem.* 1999, 9, 2293.
*Chem. Ber.* 1910, 43, 3474.
*J. Med. Chem.* 2000, 43 (16), 3168.

(Continued)

*Primary Examiner*—Celia Chang
(74) *Attorney, Agent, or Firm*—George W. Johnston; Dennis P. Tramaloni; Samuel H. Megerditchian

(57) ABSTRACT

This invention is concerned with compounds of the formula

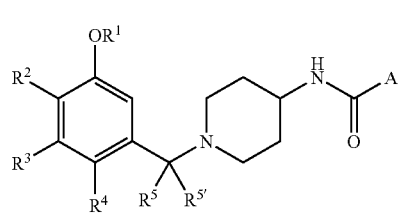

I wherein $R^1$ to $R^5$, $R^{5'}$ and A are as defined in the description and claims, and pharmaceutically acceptable salts thereof. The invention further relates to pharmaceutical compositions containing such compounds, to a process for their preparation and to their use for the treatment and/or prevention of diseases which are associated with the modulation of SST receptors subtype 5.

10 Claims, No Drawings

OTHER PUBLICATIONS

*Helv. Chim. Acta* 1977, 60, 3025-3034.
*J. Med. Chem.* 1975, 18(7), 708.
Journal of Organic Chemistry (1985), 50(13), 2236-40.
*J. Org. Chem.* 2004, 69, 6945.
Synthetic Communications, 31(12), 1921-1926; 2001.

* cited by examiner

AMIDE DERIVATIVES AS SOMATOSTATIN RECEPTOR 5 ANTAGONISTS

PRIORITY TO RELATED APPLICATIONS

This application claims the benefit of European Application No. 05104774.4, filed Jun. 2, 2005, which is hereby incorporated by reference in its entirety.

FIELD OF THE INVENTION

The present invention is directed to novel piperidin-4-yl-amide derivatives, their manufacture, pharmaceutical compositions containing them and their use as medicaments. The active compounds of the present invention are useful in the prevention and/or treatment of diabetes mellitus and other disorders.

In particular, the present invention is concerned with compounds of the general formula I

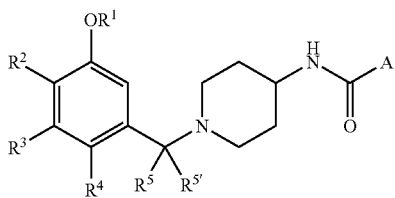

I and pharmaceutically acceptable salts thereof.

All documents cited or relied upon below are expressly incorporated herein by reference.

BACKGROUND

The compounds of formula I possess pharmaceutical activity, in particular they are modulators of somatostatin receptor activity. More particularly, the compounds are antagonists of the somatostatin receptor subtype 5 (SSTR5).

Diabetes mellitus is a systemic disease characterized by metabolic disorders involving insulin, carbohydrates, fats and proteins, and disorders in the structure and function of blood vessels. The primary symptom of acute diabetes is hyperglycemia, often accompanied by glucosuria, the presence of large amounts of glucose in urine, and polyuria, the excretion of large volumes of urine. Additional symptoms arise in chronic diabetes, including degeneration of the walls of blood vessels. Although many different human organs are affected by these vascular changes, the eyes and kidneys appear to be the most susceptible. As such, long-standing diabetes mellitus, even when treated with insulin, is a leading cause of blindness.

There are three recognized types of diabetes mellitus. Type I diabetes or insulin dependent diabetes mellitus (IDDM) is typically of juvenile onset; ketosis develops early in life with much more severe symptoms and has a near-certain prospect of later vascular involvement. Control of Type I diabetes is difficult and requires exogenous insulin administration. Type II diabetes or non-insulin dependent diabetes mellitus (NIDDM) is ketosis-resistant, generally develops later in life, is milder and has a more gradual onset. Gestational diabetes is related to type II diabetes and associated with an increased risk of later development of that disease. Type III diabetes is malnutrition-related diabetes.

NIDDM is a condition that poses a major threat to the health of the citizens of the western world. NIDDM accounts for over 85% of diabetes incidence worldwide and about 160 million people are suffering from NIDDM. The incidence is expected to increase considerably within the next decades, especially in developing countries. NIDDM is associated with morbidity and premature mortality resulting from serious complications, e.g. cardiovascular disease (G. C. Weir, J. L. Leahy, 1994, Pathogenesis of non-insulin dependent (Type II) diabetes mellitus. Joslin's Diabetes Mellitus 13th Ed. (Eds. C. R. Kahn, G. C. Weir), Lea & Febiger, Malvern, Pa., pp. 240-264). NIDDM is characterized by both fasting and post-prandial hyperglycemia resulting from abnormalities in insulin secretion and insulin action (G. C. Weir et al. vide supra).

The hyperglycemia in patients suffering from NIDDM can usually be initially treated by dieting, but eventually most NIDDM patients have to take oral antidiabetic agents and/or insulin injections to normalize their blood glucose levels. The introduction of orally effective hypoglycemic agents was an important development in the treatment of hyperglycemia by lowering blood glucose levels. Currently, the most widely used oral antidiabetic agents are the sulfonylureas, which act by increasing the secretion of insulin from the pancreas (H. E. Lebovitz, 1994, Oral antidiabetic agents. Joslin's Diabetes Mellitus 13th Ed. (Eds. C. R. Kahn, G. C. Weir), Lea & Febiger, Malvern, Pa., pp. 508-529), the biguanides (e.g. metformin) which act on the liver and periphery by unknown mechanisms (C. J. Bailey, R. C. Turner *New Engl. J. Med.*, 1996, 334, 574-579) and the thiazolidinediones (e.g. rosiglitazone/Avandia®) which enhance the effects of insulin at peripheral target sites (G. L. Plosker, D. Faulds *Drugs*, 1999, 57, 409-438). These existing therapies which comprise a wide variety of biguanide, sulfonylurea and thiazolidinedione derivatives have been used clinically as hypoglycemic agents. However, all three classes of compound have side effects. The biguanides, for example metformin, are unspecific and in certain cases have been associated with lactic acidosis, and need to be given over a longer period of time, i.e. they are not suitable for acute administration (Bailey et al., vide supra). The sulfonylureas, though having good hypoglycemic activity, require great care during use because they frequently cause serious hypoglycemia and are most effective over a period of circa ten years. The thiazolidinediones may cause weight gain following chronic administration (Plosker and Faulds, vide supra) and troglitazone has been associated with the occurrence of serious hepatic dysfunction.

Thus, there is a significant and rising need for antidiabetic drugs that have novel mechanisms of action, thereby avoiding side effects produced by known therapies. The hormone somatostatin (SST) is primarily produced in the intestinal tract and in the pancreas. In addition it acts as a neurotransmitter. The hormone is involved through its receptors in the regulation of several other hormones and in immunoregulation. In particular, SST suppresses the secretion of insulin by pancreatic β cells and the secretion of glucagon-like peptide 1 (GLP-1) by L cells. GLP-1 in turn is one of the most potent stimulators of insulin production and secretion and is a trophic factor for β cells. β and L cells express SST receptor subtype 5 (SSTR5) and agonizing this receptor suppresses insulin and GLP-1 secretion in humans and in animal models (e.g. Y. Zambre, Z. Ling, M. C. Chen, X. Hou, C. W. Woon, M. Culler, J. E. Taylor, D. H. Coy, C. van Schravendijk, F. Schuit, D. G. Pipeleers, D. L. Eizirik *Biochem. Pharmacol.*, 1999, 57, 1159-1164; S. P. Fagan, A. Azizzadeh, S. Moldovan, M. K. Ray, T. E. Adrian, X. Ding, D. H. Coy, F. C. Brunicardi *Surgery* 1998, 124, 254-258; M. Norman, S. Moldovan, V.

Seghers, X.-P. Wang, F. J. DeMayo, F. C. Brunicardi *Ann. Surg.* 2002, 235, 767-774; T. A. Tirone, M. A. Norman, S. Moldovan, F. J. DeMayo, X.-P. Wang, F. C. Brunicardi *Pancreas* 2003, 26, e67-73; M. Z. Strowski, M. Köhler, H. Y. Chen, M. E. Trumbauer, Z. Li, D. Szalkowski, S. Gopal-Truter, J. K. Fisher, J. M. Schaeffer, A. D. Blake, B. B. Zhang, H. A. Wilkinson *Mol. Endocrinol.* 2003, 17, 93-106).

Consequently, antagonizing the effect of SST would lead to higher plasma insulin concentrations. In patients suffering from impaired glucose tolerance and NIDDM, a higher plasma insulin concentration would moderate the dangerous hyperglycemia and accordingly reduce the risk of tissue damage. If such SSTR5 antagonists are sufficiently selective over the other four SST receptors, little influence is expected on secretion of other hormones. Particularly, selectivity over SST receptor subtype 2 avoids influences on glucagon secretion (K. Cejvan, D. H. Coy, S. Efendic *Diabetes* 2003, 52, 1176-1181; M. Z. Strowski, R. M. Parmar, A. D. Blake, J. M. Schaeffer *Endocrinology* 2000, 141, 111-117). Advantageous over established therapies is the dual mechanism of action to increase insulin secretion: directly on pancreatic β cells and indirectly through GLP-1 release from L cells. Additionally, SSTR5 knockout mice demonstrated higher insulin sensitivity than littermates (Strowski, Kohler et al, vide supra). Therefore, SSTR5 antagonists could have the potential to beneficially influence insulin resistance in patients with NIDDM. In summary, SSTR5 antagonists are expected to beneficially influence NIDDM, the underlying impaired fasting glucose and impaired glucose tolerance, as well as complications of long-standing, insufficiently controlled diabetes mellitus.

GLP-1 is known as an endogenous regulator of food intake reducing appetite as shown in laboratory animals, healthy volunteers and patients with NIDDM (E. Näslund, B. Barkeling, N. King, M. Gutniak, J. E. Blundell, J. J. Holst, S. Rössner, P. M. Hellström *Int. J. Obes.* 1999, 23, 304-311; J.-P. Gutzwiller, B. Göke, J. Drewe, P. Hildebrand, S. Ketterer, D. Handschin, R. Winterhalder, D. Conen, C. Beglinger *Gut* 1999, 44, 81-88; J.-P. Gutzwiller, J. Drewe, B. Göke, H. Schmidt, B. Rohrer, J. Lareida, C. Beglinger *Am. J. Physiol.* 1999, 276, R1541-1544; M. D. Turton, D. O'Shea, I. Gunn, S. A. Beak, C. M. Edwards, K. Meeran, S. J. Choi, G. M. Taylor, M. M. Heath, P. D. Lambert, J. P. Wilding, D. M. Smith, M. A. Ghatei, J. Herbert, S. R. Bloom *Nature* 1996, 379, 69-72; A. Flint, A. Raben, A. Astrup, J. J. Holst *J. Clin. Invest.* 1998, 101, 515-520; M. B. Toft-Nielsen, S. Madsbad, J. J. Holst *Diabetes Care* 1999, 22, 1137-1143); thus, elevated GLP-1 will also counteract obesity, a typical condition associated with and leading to NIDDM. Consequently, SSTR5 antagonists may also be useful for the prevention and treatment of obesity.

GLP-1 is co-secreted with GLP-2 that is, consequently, also regulated by SST through SSTR5 (L. Hansen, B. Hartmann, T. Bisgaard, H. Mineo, P. N. Jørgensen, J. J. Holst *Am. J. Phys.* 2000, 278, E1010-1018). GLP-2 is enterotrophic and beneficial in patients with malabsorption of certain origins, such as short bowel syndrome (D. G. Burrin, B. Stoll, X. Guan *Domest. Anim. Endocrinol.* 2003, 24, 103-122; K. V. Haderslev, P. B. Jeppesen, B. Hartmann, J. Thulesen, H. A. Sorensen, J. Graff, B. S. Hansen, F. Tofteng, S. S. Poulsen, J. L. Madsen, J. J. Holst, M. Staun, P. B. Mortensen *Scand. J. Gastroenterol.* 2002, 37, 392-398; P. B. Jeppesen *J. Nutr.* 2003, 133, 3721-3724).

Moreover, there is increasing evidence for a role of SST on immune cells and expression of SSTR5 on activated T lymphocytes (T. Talme, J. Ivanoff, M. Hägglund, R. J. J. van Neerven, A. Ivanoff, K. G. Sundqvist *Clin. Exp. Immunol.* 2001, 125, 71-79; D. Ferone, P. M. van Hagen, C. Semino, V. A. Dalm, A. Barreca, A. Colao, S. W. J. Lamberts, F. Minuto, L. J. Hofland *Dig. Liver Dis.* 2004, 36, S68-77, C. E. Ghamrawy, C. Rabourdin-Combe, S. Krantic *Peptides* 1999, 20, 305-311). Consequently, SSTR5 antagonists could also prove valuable in treating diseases characterized by a disturbed immune system, such as inflammatory bowel disease.

SUMMARY OF THE INVENTION

In an embodiment of the present invention, provided is a compound of the formula

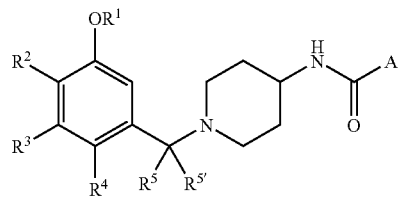

wherein $R^1$ is selected from the group consisting of ethyl, 2-fluoroethyl, isopropyl and isobutyl;

$R^2$ is selected from the group consisting of hydrogen, $C_{1-7}$-alkyl, hydroxy, $C_{1-7}$-alkoxy, $C_{3-7}$-cycloalkyl, —O—$C_{3-7}$-cycloalkyl, halogen, halogen-$C_{1-7}$-alkyl, —C(O)OR$^6$, wherein R$^6$ is $C_{1-7}$-alkyl, —NH—C(O)—R$^7$, wherein R$^7$ is $C_{1-7}$-alkyl, amino, phenyl, phenyl substituted by one to three substituents selected from the group consisting of halogen, halogen-$C_{1-7}$-alkyl and halogen-$C_{1-7}$-alkoxy, pyridyl, imidazolyl, triazolyl and pyrrolyl;

$R^3$ is selected from the group consisting of hydrogen, $C_{1-7}$-alkoxy, amino, —NH—C(O)—R$^8$, wherein R$^8$ is $C_{1-7}$-alkyl, —O-benzyl and —O-tetrahydropyranyl;

or $R^2$ and $R^3$ are bonded to each other to form a ring together with the carbon atoms they are attached to and $R^2$ and $R^3$ together are —CH=CH—NH—;

$R^4$ is selected from the group consisting of hydrogen, halogen, pyridyl and pyrimidyl;

$R^5$ and $R^{5'}$ independently from each other are selected from hydrogen or methyl;

A is selected from the group consisting of phenyl;
  phenyl substituted by one to three substituents selected from the group consisting of $C_{1-7}$-alkyl, $C_{3-7}$-cycloalkyl, $C_{1-7}$-alkylsulfonyl, —O—$C_{1-7}$-alkylsulfonyl, $C_{1-7}$-alkylsulfonyl-$C_{2-7}$-alkoxy, hydroxy, $C_{1-7}$-alkoxy, —O—$C_{3-7}$-cycloalkyl, $C_{3-7}$-cycloalkyl-$C_{1-7}$-alkoxy, hydroxy-$C_{1-7}$-alkyl, hydroxy-$C_{2-7}$-alkoxy, dihydroxy-$C_{3-7}$-alkoxy, $C_{1-7}$-alkoxy-$C_{2-7}$-alkoxy, $C_{1-7}$-alkoxy-hydroxy-$C_{3-7}$-alkoxy, $C_{1-7}$-alkylamino, di-$C_{1-7}$-alkylamino, amino-$C_{2-7}$-alkoxy, amino-$C_{1-7}$-alkyl, —C(O)NR$^{10}$R$^{11}$, —$C_{1-7}$-alkylene-C(O)NR$^{10}$R$^{11}$, —O—$C_{1-7}$-alkylene-C(O)NR$^{10}$R$^{11}$, —C(O)OR$^{10}$, —$C_{1-7}$-alkylene-C(O)OR$^{10}$, —O—$C_{1-7}$-alkylene-C(O)OR$^{10}$, halogen, cyano, halogen-$C_{1-7}$-alkyl, halogen-$C_{1-7}$-alkoxy, cyano-$C_{1-7}$-alkoxy, fluorophenyl, pyridyl, tetrazolyl and tetrazolyl-$C_{1-7}$-alkoxy; 1,3-benzodioxolyl; naphthyl; pyrimidinyl; pyridyl; pyridyl substituted by one ore two substituents selected from the group consisting of $C_{1-7}$-alkyl, $C_{1-7}$-alkoxy, amino, $C_{1-7}$-alkylamino, di-$C_{1-7}$-alkylamino, $C_{3-7}$-cycloalkylamino, halogen, cyano, morpholinyl, imidazolyl, and —NH—C(O)—R$^9$, wherein R$^9$ is $C_{1-7}$-alkyl or $C_{3-7}$-cycloalkyl, and indolyl;

$R^{10}$ and $R^{11}$ independently from each other are hydrogen or $C_{1-7}$-alkyl;

and pharmaceutically acceptable salts thereof.

In another embodiment of the present invention, provided is a process for the manufacture of a compound according to formula I, comprising the steps of: reacting a compound of the general formula

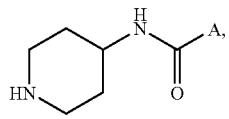

II wherein A is as defined above, with an aldehyde of the formula

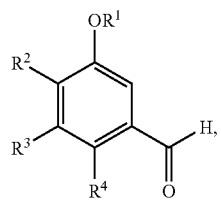

III wherein $R^1$, $R^2$, $R^3$ and $R^4$ are as defined above, by employing a reducing agent to obtain a compound of the formula

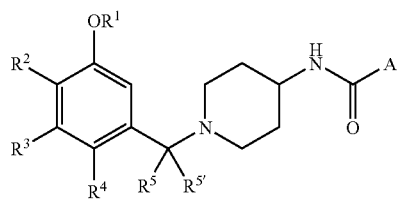

I-A wherein $R^5$ and $R^{5'}$ are hydrogen, and, if desired, converting the compound of formula I into a pharmaceutically acceptable salt, or, alternatively, reacting a compound of the general formula

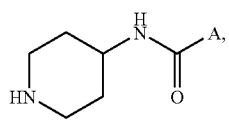

II wherein A is as defined above, with an alkyl halide of the formula

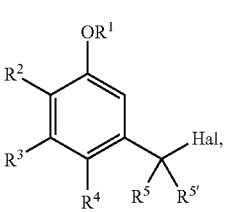

IV wherein $R^1$ to $R^5$ and $R^{5'}$ are as defined above and Hal is halogen, with the addition of a suitable base to obtain a compound of the formula

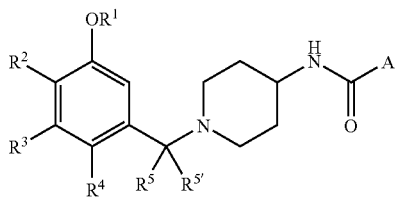

I and, if desired, converting the compound of formula I into a pharmaceutically acceptable salt, or, alternatively, coupling an amine of the general formula

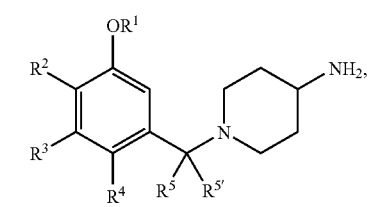

V wherein $R^1$ to $R^5$ and $R^{5'}$ are as defined above, with a carboxylic acid of the formula

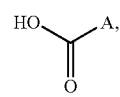

VI wherein A is as defined above, by employing a suitable coupling agent to obtain a compound of the formula

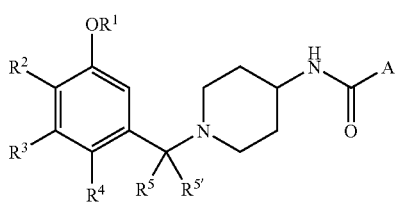

I and, if desired, converting the compound of formula I into a pharmaceutically acceptable salt, or, alternatively, coupling an amine of the general formula

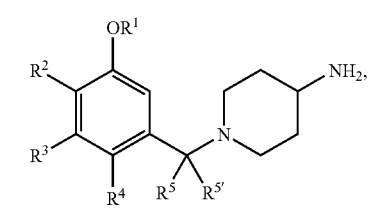

V wherein R¹ to R⁵ and R⁵' are as defined above, with an acid chloride of the formula

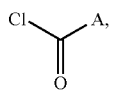

wherein A is as defined above, with the addition of a suitable base to obtain a compound of the formula

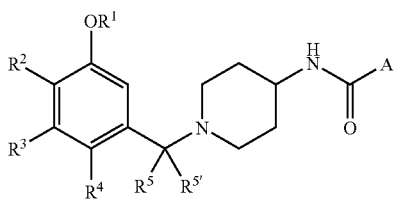

and, if desired, converting the compound of formula I into a pharmaceutically acceptable salt.

In a further embodiment of the present invention, provided is a pharmaceutical composition, comprising a therapeutically effective amount of a compound according to formula I as well as a pharmaceutically acceptable carrier and/or adjuvant.

In a yet another embodiment of the present invention, provided is a method for the treatment and/or prevention of diseases which are associated with the modulation of SST receptors subtype 5, comprising the step of administering a therapeutically effective amount of a compound according to formula I to a human being or animal in need thereof.

DETAILED DESCRIPTION

The present invention provides for selective, directly acting SSTR5 antagonists. Such antagonists are useful as therapeutically active substances, particularly in the treatment and/or prevention of diseases which are associated with the modulation of SST receptors subtype 5.

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_{1-7}$-alkyl", alone or in combination, signifies a straight-chain or branched-chain alkyl group with 1 to 7 carbon atoms, preferably a straight or branched-chain alkyl group with 1 to 4 carbon atoms. Examples of straight-chain and branched $C_{1-7}$ alkyl groups are methyl, ethyl, propyl, isopropyl, butyl, isobutyl, tert-butyl, the isomeric pentyls, the isomeric hexyls and the isomeric heptyls, preferably methyl and ethyl and most preferred the groups specifically exemplified herein.

The term "lower alkylene" or "$C_{1-7}$-alkylene", alone or in combination, signifies a straight-chain or branched-chain divalent saturated aliphatic hydrocarbyl radical of 1 to 7 carbon atoms, preferably of 1 to 4 carbon atoms, more preferably 1 to 3 carbon atoms. $C_{1-7}$-Alkylenes include the groups $(CH_2)_n$ with n being from 1 to 7, but also branched-chain groups such as —$C(CH_2)_2$—.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl.

The term "alkoxy" refers to the group R'—O—, wherein R' is alkyl. The term "lower alkoxy" or "$C_{1-7}$-alkoxy" refers to the group R'—O—, wherein R' is lower alkyl and the term "lower alkyl" has the previously given significance. Examples of lower alkoxy groups are e.g. methoxy, ethoxy, n-propoxy, isopropoxy, n-butoxy, isobutoxy, sec-butoxy and tert-butoxy, preferably methoxy and ethoxy and most preferred the groups specifically exemplified herein.

The term "halogen" refers to fluorine, chlorine, bromine and iodine, with fluorine, chlorine and bromine being preferred.

The term "lower halogenalkyl" or "halogen-$C_{1-7}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, fluoromethyl, 2-fluoroethyl, 2,2,2-trifluoroethyl and chloromethyl, with trifluoromethyl and 2-fluoroethyl being especially preferred.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluoromethoxy and chloromethoxy, with trifluoromethoxy being especially preferred.

The term "alkylsulfonyl" refers to the group R'—$SO_2$—, wherein R' is alkyl. The term "lower alkylsulfonyl" or "$C_{1-7}$-alkylsulfonyl" refers to the group R'—$SO_2$—, wherein R' is lower alkyl. Examples of lower alkylsulfonyl groups are e.g. methylsulfonyl or ethylsulfonyl.

The term "lower alkylsulfonyl-alkoxy" or "$C_{1-7}$-alkylsulfonyl-$C_{1-7}$-alkoxy" refers to lower alkoxy groups as defined above wherein at least one of the hydrogen atoms of the lower alkoxy group is replaced by a lower alkylsulfonyl group as defined above. A preferred lower alkylsulfonyl-alkoxy group is methylsulfonylmethoxy.

The term "$C_{3-7}$-cycloalkyl-$C_{1-7}$-alkoxy" refers to lower alkoxy groups as defined above wherein at least one of the hydrogen atoms of the lower alkoxy group is replaced by a cycloalkyl group as defined above.

The term "alkylamino" or "$C_{1-7}$-alkylamino" refers to the group —NHR', wherein R' is lower alkyl and the term "lower alkyl" has the previously given significance. A preferred alkylamino group is methylamino.

The term "dialkylamino" or "di-$C_{1-7}$-alkylamino" refers to the group —NR'R", wherein R' and R" are lower alkyl and the term "lower alkyl" has the previously given significance. A preferred dialkylamino group is dimethylamino.

The term "cycloalkylamino" or "$C_{3-7}$-cycloalkylamino" refers to the group —NHR", wherein R" is a cycloalkyl group as defined above. A preferred cycloalkylamino group is cyclopropylamino.

The term "lower hydroxyalkyl" or "hydroxy-$C_{1-7}$-alkyl" refers to lower alkyl groups as defined above wherein one of the hydrogen atoms of the lower alkyl group is replaced by a hydroxy group. Preferred hydroxyalkyl groups are hydroxymethyl and 2-hydroxyethyl.

The term "lower hydroxyalkoxy" or "hydroxy-$C_{2-7}$-alkoxy" refers to lower alkoxy groups as defined above (however, having at least 2 carbon atoms) wherein one of the hydrogen atoms of the lower alkoxy group is replaced by a hydroxy group.

The term "dihydroxy-$C_{3-7}$-alkoxy" refers to lower alkoxy groups as defined above (however, having at least 3 carbon atoms) wherein two hydrogen atoms on different carbon atoms of the lower alkoxy group are replaced by hydroxy groups. A preferred dihydroxyalkoxy group is 2,3-dihydroxypropoxy.

The term "$C_{1-7}$-alkoxy-$C_{2-7}$-alkoxy" refers to refers to lower alkoxy groups as defined above (however, having at least 2 carbon atoms) wherein at least one of the hydrogen atoms of the lower alkoxy group is replaced by a lower alkoxy group as defined above.

The term "$C_{1-7}$-alkoxy-hydroxy-$C_{3-7}$-alkoxy" refers to refers to lower alkoxy groups as defined above (however, having at least 3 carbon atoms) wherein one of the hydrogen atoms of the lower alkoxy group is replaced by a lower alkoxy group as defined above and a hydrogen atom bound to another carbon atom of the alkoxy group is replaced by a hydroxy group.

The term "cyano-$C_{1-7}$-alkoxy" refers to lower alkoxy groups as defined above wherein at least one of the hydrogen atoms of the lower alkoxy group is replaced by a cyano group. A preferred cyanoalkoxy group is cyanomethoxy.

The term "tetrazolyl-$C_{1-7}$-alkoxy" refers to a lower alkoxy group as defined above wherein at least one of the hydrogen atoms of the lower alkoxy group is replaced by a tetrazolyl group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place, e.g. as a consequence of hygroscopic properties of an initially anhydrous compound of formula I (hydration). The term pharmaceutically acceptable salts also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four non-identical substituents is termed a "chiral center".

In detail, the present invention relates to the general formula I

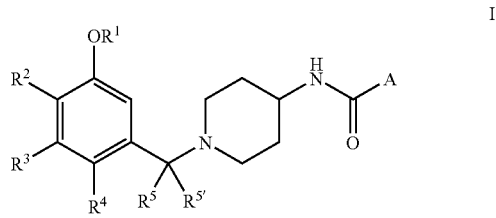

wherein $R^1$ is selected from the group consisting of ethyl, 2-fluoroethyl, isopropyl and isobutyl;

$R^2$ is selected from the group consisting of hydrogen, $C_{1-7}$-alkyl, hydroxy, $C_{1-7}$-alkoxy, $C_{3-7}$-cycloalkyl, —O—$C_{3-7}$-cycloalkyl, halogen, halogen-$C_{1-7}$-alkyl, —C(O)OR$^6$, wherein R$^6$ is $C_{1-7}$-alkyl, —NH—C(O)—R$^7$, wherein R$^7$ is $C_{1-7}$-alkyl, amino, phenyl, phenyl substituted by one to three substituents selected from the group consisting of halogen, halogen-$C_{1-7}$-alkyl and halogen-$C_{1-7}$-alkoxy, pyridyl, imidazolyl, triazolyl and pyrrolyl;

$R^3$ is selected from the group consisting of hydrogen, $C_{1-7}$-alkoxy, amino, —NH—C(O)—R$^8$, wherein R$^8$ is $C_{1-7}$-alkyl, —O-benzyl and —O-tetrahydropyranyl;

or $R^2$ and $R^3$ are bonded to each other to form a ring together with the carbon atoms they are attached to and $R^2$ and $R^3$ together are —CH=CH—NH—;

$R^4$ is selected from the group consisting of hydrogen, halogen, pyridyl and pyrimidyl;

$R^5$ and $R^{5'}$ independently from each other are selected from hydrogen or methyl;

A is selected from the group consisting of phenyl;
  phenyl substituted by one to three substituents selected from the group consisting of $C_{1-7}$-alkyl, $C_{3-7}$-cycloalkyl, $C_{1-7}$-alkylsulfonyl, —O—$C_{1-7}$-alkylsulfonyl, $C_{1-7}$-alkylsulfonyl-$C_{2-7}$-alkoxy, hydroxy, $C_{1-7}$-alkoxy, —O—$C_{3-7}$-cycloalkyl, —$C_{3-7}$-cycloalkyl-$C_{1-7}$-alkoxy, hydroxy-$C_{1-7}$-alkyl, hydroxy-$C_{2-7}$-alkoxy, dihydroxy-$C_{3-7}$-alkoxy, $C_{1-7}$-alkoxy-$C_{2-7}$-alkoxy, $C_{1-7}$-alkoxy-hydroxy-$C_{3-7}$-alkoxy, $C_{1-7}$-alkylamino, di-$C_{1-7}$-alkylamino, amino-$C_{2-7}$-alkoxy, amino-$C_{1-7}$-alkyl, —C(O)NR$^{10}$R$^{11}$, —$C_{1-7}$-alkyl-C(O)NR$^{10}$R$^{11}$, —O—$C_{1-7}$-alkyl-C(O)NR$^{10}$R$^{11}$, —C(O)OR$^{10}$, —$C_{1-7}$-alkyl-C(O)OR$^{10}$, —O—$C_{1-7}$-alkyl-C(O)OR$^{10}$, halogen, cyano, halogen-$C_{1-7}$-alkyl, halogen-$C_{1-7}$-alkoxy, cyano-$C_{1-7}$-alkoxy, fluorophenyl, pyridyl, tetrazolyl and tetrazolyl-$C_{1-7}$-alkoxy; 1,3-benzodioxolyl; naphthyl; pyrimidinyl; pyridyl;
  pyridyl substituted by one ore two substituents selected from the group consisting of $C_{1-7}$-alkyl, $C_{1-7}$-alkoxy, amino, $C_{1-7}$-alkylamino, di-$C_{1-7}$-alkylamino, $C_{3-7}$-cycloalkylamino, halogen, cyano, morpholinyl, imidazolyl, and —NH—C(O)—R$^9$, wherein R$^9$ is $C_{1-7}$-alkyl or $C_{3-7}$-cycloalkyl, and indolyl;

$R^{10}$ and $R^{11}$ independently from each other are hydrogen or $C_{1-7}$-alkyl;

and pharmaceutically acceptable salts thereof.

One group of preferred compounds of formula I according to the present invention are those, wherein A is phenyl or phenyl substituted by one to three substituents selected from the group consisting of $C_{1-7}$-alkyl, $C_{3-7}$-cycloalkyl, $C_{1-7}$-alkylsulfonyl, —O—$C_{1-7}$-alkylsulfonyl, $C_{1-7}$-alkylsulfonyl-$C_{2-7}$-alkoxy, hydroxy, $C_{1-7}$-alkoxy, —O—$C_{3-7}$-cycloalkyl, $C_{3-7}$-cycloalkyl-$C_{1-7}$-alkoxy, hydroxy-$C_{1-7}$-alkyl, hydroxy-$C_{2-7}$-alkoxy, dihydroxy-$C_{3-7}$-alkoxy, $C_{1-7}$-alkoxy-$C_{2-7}$-alkoxy, $C_{1-7}$-alkoxy-hydroxy-$C_{3-7}$-alkoxy, $C_{1-7}$-alkylamino, di-$C_{1-7}$-alkylamino, amino-$C_{2-7}$-alkoxy, amino-$C_{1-7}$-alkyl, —C(O)NR$^{10}$R$^{11}$, —$C_{1-7}$-alkylene-C(O)NR$^{10}$R$^{11}$, —O—$C_{1-7}$-alkylene-C(O)NR$^{10}$R$^{11}$, —C(O)OR$^{10}$, —$C_{1-7}$-alkylene-C(O)OR$^{10}$, —O—$C_{1-7}$-alkylene-C(O)OR$^{10}$, halogen, cyano, halogen-$C_{1-7}$-alkyl, halogen-$C_{1-7}$-alkoxy, cyano-$C_{1-7}$-alkoxy, fluorophenyl, pyridyl, tetrazolyl and tetrazolyl-$C_{1-7}$-alkoxy.

More preferred compounds of formula I of the present invention are those, wherein A is phenyl or phenyl substituted by one to three substituents selected from the group consisting of $C_{1-7}$-alkylsulfonyl, $C_{1-7}$-alkoxy, $C_{1-7}$-alkyl, $C_{1-7}$-alkylamino, di-$C_{1-7}$-alkylamino, —C(O)NH$_2$ and halogen.

Especially preferred are further those compounds of formula I, wherein A is phenyl substituted by one to three substituents selected from the group consisting of $C_{1-7}$-alkyl, $C_{1-7}$-aklylsulfonyl, $C_{1-7}$-alkoxy, hydroxy-$C_{1-7}$-alkyl, $C_{1-7}$-alkylamino, di-$C_{1-7}$-alkylamino, hydroxy-$C_{2-7}$-alkoxy, dihydroxy-$C_{3-7}$-alkoxy, —O—$C_{1-7}$-alkylene-C(O)NR$^{10}$R$^{11}$, —C(O)OR$^{10}$, halogen, cyano, halogen-$C_{1-7}$-alkyl, halogen-$C_{1-7}$-alkoxy and cyano-$C_{1-7}$-alkoxy.

Also preferred are compounds of formula I according to the invention, wherein A is phenyl substituted by one to three substituents selected from the group consisting of $C_{1-7}$-alkylsulfonyl, $C_{1-7}$-alkoxy, $C_{1-7}$-alkyl, $C_{1-7}$-alkylamino, di-$C_{1-7}$-alkylamino, —C(O)NH$_2$ and halogen, with those compounds of formula I, wherein A is phenyl substituted by $C_{1-7}$-alkylsulfonyl or $C_{1-7}$-alkyl, being especially preferred.

Furthermore, compounds of formula I according to the invention are preferred, wherein A is selected from the group consisting of 1,3-benzodioxolyl;

naphthyl;

pyrimidyl;

pyridyl;

pyridyl substituted by one or two substituents selected from the group consisting of $C_{1-7}$-alkyl, $C_{1-7}$-alkoxy, amino, $C_{1-7}$-alkylamino, di-$C_{1-7}$-alkylamino, $C_{3-7}$-cycloalkylamino, halogen, cyano, morpholinyl, imidazolyl, and —NH—C(O)—R$^9$, wherein R$^9$ is $C_{1-7}$-alkyl or $C_{3-7}$-cycloalkyl, and indolyl.

Especially preferred are those compounds of formula I according to the invention, wherein A is pyridyl or pyridyl substituted by one or two substituents selected from the group consisting of $C_{1-7}$-alkyl, $C_{1-7}$-alkoxy, amino, $C_{1-7}$-alkylamino, di-$C_{1-7}$-alkylamino, $C_{3-7}$-cycloalkylamino, halogen, cyano, morpholinyl, imidazolyl, and —NH—C(O)—R$^9$, wherein R$^9$ is $C_{1-7}$-alkyl or $C_{3-7}$-cycloalkyl, with those compounds, wherein A is pyridyl substituted by one or two substituents selected from the group consisting of $C_{1-7}$-alkyl, amino, $C_{1-7}$-alkylamino, cyano and halogen, being more preferred.

Also preferred are compounds of formula I, wherein A is pyridyl or pyridyl substituted by one ore two substituents selected from the group consisting of $C_{1-7}$-alkyl, $C_{1-7}$-alkoxy, amino, $C_{1-7}$-alkylamino, di-$C_{1-7}$-alkylamino, morpholinyl, imidazolyl, and —NH—C(O)—R$^9$, wherein R$^9$ is $C_{1-7}$-alkyl or $C_{3-7}$-cycloalkyl, with those compounds of formula I, wherein A is pyridyl substituted by $C_{1-7}$-alkyl, being especially preferred.

Furthermore, compounds of formula I according to the present invention are preferred, wherein R$^2$ is selected from the group consisting of hydrogen, $C_{1-7}$-alkyl, hydroxy, $C_{1-7}$-alkoxy, $C_{3-7}$-cycloalkyl, —O—$C_{3-7}$-cycloalkyl, halogen, halogen-$C_{1-7}$-alkyl, —C(O)OR$^6$, wherein R$^6$ is $C_{1-7}$-alkyl, —NH—C(O)—R$^7$, wherein R$^7$ is $C_{1-7}$-alkyl, amino, pyridyl, imidazolyl, triazolyl and pyrrolyl.

Especially preferred are those compounds of formula I, wherein R$^2$ is selected from the group consisting of $C_{1-7}$-alkyl, hydroxy, $C_{1-7}$-alkoxy, —O—$C_{3-7}$-cycloalkyl, halogen, halogen-$C_{1-7}$-alkyl, —C(O)OR$^6$, wherein R$^6$ is $C_{1-7}$-alkyl, —NH—C(O)—R$^7$, wherein R$^7$ is $C_{1-7}$-alkyl, amino and pyrrolyl.

More preferred are compounds of formula I, wherein R$^2$ is selected from $C_{1-7}$-alkyl, $C_{1-7}$-alkoxy and halogen.

Also more preferred are compounds of formula I, wherein R$^2$ is imidazolyl or pyrrolyl.

Furthermore, compounds of formula I are also preferred, wherein R$^2$ is phenyl or phenyl substituted by one to three substituents selected from the group consisting of halogen, halogen-$C_{1-7}$-alkyl and halogen-$C_{1-7}$-alkoxy, with those compounds of formula I being most preferred, wherein R$^2$ is phenyl substituted by one to three substituents selected from the group consisting of halogen, halogen-$C_{1-7}$-alkyl and halogen-$C_{1-7}$-alkoxy.

Also preferred are compounds of formula I according to the invention, wherein R$^3$ and R$^4$ are hydrogen.

Furthermore, compounds of formula I are preferred, wherein R$^3$ is $C_{1-7}$-alkoxy or —O-tetrahydropyranyl.

Another group of preferred compounds of formula I are those, wherein R$^4$ is pyridyl or pyrimidyl. Within this group those compounds of formula I are preferred, wherein R$^3$ is hydrogen.

Preferred compounds of formula I according to the invention are further those, wherein R$^5$ and R$^{5'}$ are hydrogen.

Furthermore, compounds of formula I according to the present invention are preferred, wherein R$^1$ is ethyl.

Preferred are furthermore compounds of formula I, wherein

R$^1$ is selected from the group consisting of ethyl, isopropyl and isobutyl;

R$^2$ is selected from the group consisting of hydrogen, $C_{1-7}$-alkyl, hydroxy, $C_{1-7}$-alkoxy, —O—$C_{3-7}$-cycloalkyl, halogen, halogen-$C_{1-7}$-alkyl, —C(O)OR$^6$, wherein R$^6$ is $C_{1-7}$-alkyl, —NH—C(O)—R$^7$, wherein R$^7$ is $C_{1-4}$-alkyl, amino and pyrrolyl;

R$^3$ is selected from the group consisting of hydrogen, $C_{1-7}$-alkoxy, amino, —NH—C(O)—R$^8$, wherein R$^8$ is $C_{1-7}$-alkyl, and —O-tetrahydropyranyl;

R$^4$ is selected from the group consisting of hydrogen, halogen, pyridyl and pyrimidyl;

R$^5$ and R$^{5'}$ independently from each other are selected from hydrogen or methyl;

A is selected from the group consisting of phenyl;

phenyl substituted by one to three substituents selected from the group consisting of $C_{1-7}$-alkylsulfonyl, $C_{1-7}$-alkoxy, $C_{1-7}$-alkyl, $C_{1-7}$-alkylamino, di-$C_{1-7}$-alkylamino, —C(O)NH$_2$ and halogen;

1,3-benzodioxolyl;

naphthyl;

pyridyl;

pyridyl substituted by one ore two substituents selected from the group consisting of $C_{1-7}$-alkyl, $C_{1-7}$-alkoxy, amino, $C_{1-7}$-alkylamino, di-$C_{1-7}$-alkylamino, morpholinyl, imidazolyl, and —NH—C(O)—$R^9$, wherein $R^9$ is $C_{1-7}$-alkyl or $C_{3-7}$-cycloalkyl; and
indolyl;
and pharmaceutically acceptable salts thereof.

Within this group, compounds of formula I of the present invention are preferred, wherein $R^2$ is selected from the group consisting of $C_{1-7}$-alkyl, hydroxy, $C_{1-7}$-alkoxy, —O—$C_{3-7}$-cycloalkyl, halogen, halogen-$C_{1-7}$-alkyl, —C(O)O$R^6$, wherein $R^6$ is $C_{1-7}$-alkyl, —NH—C(O)—$R^7$, wherein $R^7$ is $C_{1-7}$-alkyl, amino and pyrrolyl.

More preferred in this group are those compounds of formula I, wherein $R^2$ is selected from $C_{1-7}$-alkyl, $C_{1-7}$-alkoxy and halogen, with those compounds wherein $R^2$ is halogen, especially chloro, being most preferred.

Especially preferred are also compounds of formula I according to the invention, wherein $R^2$ is selected from the group consisting of $C_{1-7}$-alkyl, hydroxy, $C_{1-7}$-alkoxy, —O—$C_{3-7}$-cycloalkyl, halogen, halogen-$C_{1-7}$-alkyl, —C(O)O$R^6$, —NH—C(O)—$R^7$, amino and pyrrolyl, and wherein $R^3$ and $R^4$ are hydrogen.

Examples of preferred compounds of formula I are the following:

N-[1-(4-chloro-3-ethoxy-benzyl)piperidin-4-yl]-6-imidazol-1-yl-nicotinamide,
N-[1-(4-chloro-3-ethoxy-benzyl)piperidin-4-yl]-2-morpholin-4-yl-isonicotinamide,
1H-indole-4-carboxylic acid[1-(4-chloro-3-ethoxy-benzyl)piperidin-4-yl]-amide,
N-[1-(4-chloro-3-ethoxy-benzyl)piperidin-4-yl]-3-methanesulfonylbenzamide,
N-[1-(4-chloro-3-ethoxy-benzyl)piperidin-4-yl]-6-dimethylamino-nicotinamide,
N-[1-(4-chloro-3-ethoxy-benzyl)piperidin-4-yl]-isophthalimide,
N-[1-(4-chloro-3-ethoxy-benzyl)piperidin-4-yl]-benzamide,
1H-indole-7-carboxylic acid[1-(4-chloro-3-ethoxy-benzyl)piperidin-4-yl]-amide,
N-[1-(4-chloro-3-ethoxy-benzyl)piperidin-4-yl]-4-isopropyl-benzamide,
4-tert-butyl-N-[1-(4-chloro-3-ethoxy-benzyl)piperidin-4-yl]-benzamide,
N-[1-(4-chloro-3-ethoxy-benzyl)piperidin-4-yl]-4-ethyl-benzamide,
N-[1-(4-chloro-3-ethoxy-benzyl)piperidin-4-yl]-3-methyl-benzamide,
N-[1-(4-chloro-3-ethoxy-benzyl)piperidin-4-yl]-5-methoxy-nicotinamide,
N-[1-(4-chloro-3-ethoxy-benzyl)piperidin-4-yl]-4-methyl-benzamide,
N-[1-(4-chloro-3-ethoxy-benzyl)piperidin-4-yl]-4-chloro-benzamide,
N-[1-(4-chloro-3-ethoxy-benzyl)piperidin-4-yl]-3-methoxy-benzamide,
N-[1-(4-chloro-3-ethoxy-benzyl)piperidin-4-yl]-2-methyl-benzamide,
N-[1-(4-chloro-3-ethoxy-benzyl)piperidin-4-yl]-2,5-dimethyl-benzamide,
N-[1-(4-chloro-3-ethoxy-benzyl)piperidin-4-yl]-4-methoxy-benzamide,
N-[1-(4-chloro-3-ethoxy-benzyl)piperidin-4-yl]-2,4-dimethyl-benzamide,
napthalene-1-carboxylic acid[1-(4-chloro-3-ethoxy-benzyl)piperidin-4-yl]-amide,
N-[1-(4-chloro-3-ethoxy-benzyl)piperidin-4-yl]-3-dimethylamino-benzamide,
N-[1-(4-chloro-3-ethoxy-benzyl)piperidin-4-yl]-6-methyl-nicotinamide,
N-[1-(4-chloro-3-ethoxy-benzyl)piperidin-4-yl]-3,5-dimethoxy-benzamide,
N-[1-(4-chloro-3-ethoxy-benzyl)piperidin-4-yl]-3-methoxy-4-methyl-benzamide,
benzo[1,3]dioxole-5-carboxylic acid[1-(4-chloro-3-ethoxy-benzyl)piperidin-4-yl]-amide,
N-[1-(4-chloro-3-ethoxy-benzyl)piperidin-4-yl]-2,3-dimethoxy-benzamide,
6-amino-N-[1-(4-chloro-3-ethoxy-benzyl)piperidin-4-yl]-nicotinamide,
5-amino-N-[1-(4-chloro-3-ethoxy-benzyl)piperidin-4-yl]-nicotinamide,
N-[1-(4-chloro-3-ethoxy-benzyl)piperidin-4-yl]-5-methyl-nicotinamide,
N-[1-(3,5-diethoxy-benzyl)piperidin-4-yl]-5-methyl-nicotinamide,
N-[1-(4-amino-3,5-diethoxy-benzyl)piperidin-4-yl]-5-methyl-nicotinamide,
N-{1-[3-ethoxy-5-(tetrahydro-pyran-4-yl-oxy)-benzyl]piperidin-4-yl}-5-methyl-nicotinamide,
N-[1-(3-ethoxy-4-methyl-benzyl)piperidin-4-yl]-5-methyl-nicotinamide,
N-[1-(3,5-diethoxy-4-ethoxycarbonyl-benzyl)piperidin-4-yl]-5-methyl-nicotinamide,
N-[1-(3-ethoxy-4-fluoro-benzyl)piperidin-4-yl]-5-methyl-nicotinamide,
N-{1-[3-ethoxy-4-(1-ethyl-propoxy)-benzyl]piperidin-4-yl}-5-methyl-nicotinamide,
N-[1-(5-amino-3-ethoxy-4-iodo-benzyl)piperidin-4-yl]-5-methyl-nicotinamide,
N-[1-(3-ethoxy-4-hydroxy-benzyl)piperidin-4-yl]-5-methyl-nicotinamide,
N-[1-(3,5-diethoxy-4-pyrrol-1-yl-benzyl)piperidin-4-yl]-5-methyl-nicotinamide,
N-[1-(3-ethoxy-4-methoxy-benzyl)piperidin-4-yl]-5-methyl-nicotinamide,
N-[1-(4-chloro-3-ethoxy-benzyl)piperidin-4-yl]-6-(cyclopropanecarbonyl-amino)-nicotinamide,
N-[1-(4-chloro-3-ethoxy-benzyl)piperidin-4-yl]-5-(cyclopropanecarbonyl-amino)-nicotinamide,
5-acetylamino-N-[1-(4-chloro-3-ethoxy-benzyl)piperidin-4-yl]-nicotinamide,
N-[1-(3-ethoxy-4-methoxy-2-pyridine-4-yl-)piperidin-4-yl-benzyl]-5-methyl-nicotinamide,
N-[1-(3-ethoxy-4-methoxy-2-pyrimidin-5-yl-benzyl)piperidin-4-yl]-5-methyl-nicotinamide,
rac-N-{1-[1-(4-chloro-3-ethoxy-phenyl)piperidin-4-yl]-ethyl}-5-methyl-nicotinamide,
N-[1-(4-chloro-3-ethoxy-benzyl)-piperidin-4-yl]-isophthalamic acid methyl ester,
N-[1-(4-chloro-3-ethoxy-benzyl)-piperidin-4-yl]-isophthalamic acid,
2-{3-[1-(3,5-diethoxy-4-fluoro-benzyl)-piperidin-4-ylcarbamoyl]-phenoxy}-2-methyl-propionic acid ethyl ester,
2-{3-[1-(3,5-diethoxy-4-pyrrol-1-yl-benzyl)-piperidin-4-ylcarbamoyl]-phenoxy}-2-methyl-propionic acid ethyl ester,
2-{3-[1-(3-ethoxy-4-methoxy-benzyl)-piperidin-4-ylcarbamoyl]-phenoxy}-2-methyl-propionic acid ethyl ester,
2-{3-[1-(3,5-diethoxy-4-fluoro-benzyl)-piperidin-4-ylcarbamoyl]-phenoxy}-2-methyl-propionic acid,
2-{3-[1-(3,5-diethoxy-4-pyrrol-1-yl-benzyl)-piperidin-4-ylcarbamoyl]-phenoxy}-2-methyl-propionic acid,
2-{3-[1-(3-ethoxy-4-methoxy-benzyl)-piperidin-4-ylcarbamoyl]-phenoxy}-2-methyl-propionic acid, pyrimidine-5-carboxylic acid[1-(3,5-diethoxy-4-fluoro-benzyl)-piperidin-4-yl]-amide,
pyrimidine-5-carboxylic acid[1-(3,5-diethoxy-4-pyrrol-1-yl-benzyl)-piperidin-4-yl]-amide,
pyrimidine-5-carboxylic acid[1-(3-ethoxy-4-methoxy-benzyl)-piperidin-4-yl]-amide,
pyrimidine-5-carboxylic acid[1-(3-ethoxy-4-fluoro-benzyl)-piperidin-4-yl]-amide,
2-{4-[1-(3-ethoxy-4-methoxy-benzyl)-piperidin-4-ylcarbamoyl]-phenyl}-2-methyl-propionic acid methyl ester,
2-{4-[1-(3,5-diethoxy-4-fluoro-benzyl)-piperidin-4-ylcarbamoyl]-phenyl}-2-methyl-propionic acid methyl ester,
2-{4-[1-(3,5-diethoxy-4-pyrrol-1-yl-benzyl)-piperidin-4-ylcarbamoyl]-phenyl}-2-methyl-propionic acid methyl ester,
2-{4-[1-(3-ethoxy-4-methoxy-benzyl)-piperidin-4-ylcarbamoyl]-phenyl}-2-methyl-propionic acid,
2-{4-[1-(3,5-diethoxy-4-fluoro-benzyl)-piperidin-4-ylcarbamoyl]-phenyl}-2-methyl-propionic acid,
2-{4-[1-(3,5-diethoxy-4-pyrrol-1-yl-benzyl)-piperidin-4-ylcarbamoyl]-phenyl}-2-methyl-propionic acid,
2-{3-[1-(3,5-diethoxy-4-fluoro-benzyl)-piperidin-4-ylcarbamoyl]-5-methoxy-phenoxy}-2-methyl-propionic acid ethyl ester,
2-{3-[1-(3,5-diethoxy-4-pyrrol-1-yl-benzyl)-piperidin-4-ylcarbamoyl]-5-methoxy-phenoxy}-2-methyl-propionic acid ethyl ester,
2-{3-[1-(3-ethoxy-4-methoxy-benzyl)-piperidin-4-ylcarbamoyl]-5-methoxy-phenoxy}-2-methyl-propionic acid ethyl ester,
2-{3-[1-(3,5-diethoxy-4-fluoro-benzyl)-piperidin-4-ylcarbamoyl]-5-methoxy-phenoxy}-2-methyl-propionic acid,
2-{3-[1-(3,5-diethoxy-4-pyrrol-1-yl-benzyl)-piperidin-4-ylcarbamoyl]-5-methoxy-phenoxy}-2-methyl-propionic acid,
2-{3-[1-(3-ethoxy-4-methoxy-benzyl)-piperidin-4-ylcarbamoyl]-5-methoxy-phenoxy}-2-methyl-propionic acid,
methanesulfonic acid 3-[1-(3-ethoxy-4-methyl-benzyl)-piperidin-4-ylcarbamoyl]-phenyl ester,
methanesulfonic acid 3-[1-(4-chloro-3-ethoxy-benzyl)-piperidin-4-ylcarbamoyl]-phenyl ester,
methanesulfonic acid 3-[1-(3,5-diethoxy-4-pyrrol-1-yl-benzyl)-piperidin-4-ylcarbamoyl]-phenyl ester,
methanesulfonic acid 3-[1-(2-ethoxy-4'-trifluoromethyl-biphenyl-4-ylmethyl)-piperidin-4-ylcarbamoyl]-phenyl ester,
methanesulfonic acid 3-{1-[4-fluoro-3-(2-fluoro-ethoxy)-benzyl]-piperidin-4-ylcarbamoyl}-phenyl ester,
methanesulfonic acid 3-[1-(3-ethoxy-4-fluoro-benzyl)-piperidin-4-ylcarbamoyl]-phenyl ester,
methanesulfonic acid 3-[1-(2-ethoxy-4'-fluoro-biphenyl-4-ylmethyl)-piperidin-4-ylcarbamoyl]-phenyl ester,
6-amino-N-[1-(2-ethoxy-4'-fluoro-biphenyl-4-ylmethyl)-piperidin-4-yl]-nicotinamide,
6-amino-N-[1-(3-ethoxy-4-fluoro-benzyl)-piperidin-4-yl]-nicotinamide,
N-[1-(3-ethoxy-4-methyl-benzyl)-piperidin-4-yl]-3-methanesulfonyl-benzamide,
N-[1-(2-ethoxy-4'-fluoro-biphenyl-4-ylmethyl)-piperidin-4-yl]-3-methanesulfonyl-benzamide,
N-[1-(3-ethoxy-4-fluoro-benzyl)-piperidin-4-yl]-3-methanesulfonyl-benzamide,
6-amino-N-[1-(3,5-diethoxy-4-fluoro-benzyl)-piperidin-4-yl]-nicotinamide,
6-amino-N-[1-(3-ethoxy-4-methyl-benzyl)-piperidin-4-yl]-nicotinamide,
N-[1-(3,5-diethoxy-4-fluoro-benzyl)-piperidin-4-yl]-5-methyl-nicotinamide,
6-amino-N-{1-[4-fluoro-3-(2-fluoro-ethoxy)-benzyl]-piperidin-4-yl}-nicotinamide,
N-[1-(2-ethoxy-4'-fluoro-biphenyl-4-ylmethyl)-piperidin-4-yl]-5-methyl-nicotinamide,
6-amino-N-[1-(2-ethoxy-4'-trifluoromethyl-biphenyl-4-ylmethyl)-piperidin-4-yl]-nicotinamide,
N-[1-(2-ethoxy-biphenyl-4-ylmethyl)-piperidin-4-yl]-5-methyl-nicotinamide,
N-[1-(2-ethoxy-4'-trifluoromethyl-biphenyl-4-ylmethyl)-piperidin-4-yl]-5-methyl-nicotinamide,
6-amino-N-[1-(2-ethoxy-biphenyl-4-ylmethyl)-piperidin-4-yl]-nicotinamide,
6-amino-N-{1-[3-(2-fluoro-ethoxy)-4-methyl-benzyl]-piperidin-4-yl}-nicotinamide,
6-amino-N-[1-(2-benzyloxy-6-ethoxy-4'-fluoro-biphenyl-4-ylmethyl)-piperidin-4-yl]-nicotinamide,
6-amino-N-[1-(3,5-diisopropoxy-benzyl)-piperidin-4-yl]-nicotinamide,
methanesulfonic acid 3-[1-(4-ethoxy-1H-indol-6-ylmethyl)-piperidin-4-ylcarbamoyl]-phenyl ester,
N-[1-(4-ethoxy-1H-indol-6-ylmethyl)-piperidin-4-yl]-5-methyl-nicotinamide,
N-[1-(3,5-diisopropoxy-benzyl)-piperidin-4-yl]-5-methyl-nicotinamide,
N-[1-(3,5-diisopropoxy-benzyl)-piperidin-4-yl]-3-methanesulfonyl-benzamide,
N-[1-(4-ethoxy-1H-indol-6-ylmethyl)-piperidin-4-yl]-3-methanesulfonyl-benzamide,
methanesulfonic acid 3-[1-(3,5-diisopropoxy-benzyl)-piperidin-4-ylcarbamoyl]-phenyl ester,
methanesulfonic acid 3-[1-(2,6-diethoxy-4'-fluoro-biphenyl-4-ylmethyl)-piperidin-4-ylcarbamoyl]-phenyl ester,
N-[1-(3,5-diethoxy-4-fluoro-benzyl)-piperidin-4-yl]-6-methylamino-nicotinamide,
N-[1-(3-ethoxy-4-pyridin-3-yl-benzyl)-piperidin-4-yl]-3-methanesulfonyl-benzamide,
N-[1-(3-ethoxy-4-pyridin-3-yl-benzyl)-piperidin-4-yl]-5-methyl-nicotinamide,
methanesulfonic acid 3-[1-(3-ethoxy-4-pyridin-3-yl-benzyl)-piperidin-4-ylcarbamoyl]-phenyl ester,
N-[1-(2-ethoxy-4-fluoro-biphenyl-4-ylmethyl)-piperidin-4-yl]-6-methylamino-nicotinamide,
6-amino-N-[1-(2-ethoxy-4'-fluoro-biphenyl-4-ylmethyl)-piperidin-4-yl]-5-methyl-nicotinamide,
6-amino-N-[1-(3-ethoxy-4-methyl-benzyl)-piperidin-4-yl]-5-methyl-nicotinamide,
6-amino-N-[1-(3-ethoxy-4-pyridin-3-yl-benzyl)-piperidin-4-yl]-nicotinamide,
N-[1-(3-ethoxy-4-pyridin-4-yl-benzyl)-piperidin-4-yl]-5-methyl-nicotinamide,
N-[1-(3-ethoxy-4-pyridin-4-yl-benzyl)-piperidin-4-yl]-3-methanesulfonyl-benzamide,
methanesulfonic acid 3-[1-(3-ethoxy-4-pyridin-4-yl-benzyl)-piperidin-4-ylcarbamoyl]-phenyl ester,
6-amino-N-[1-(4-chloro-3-ethoxy-benzyl)-piperidin-4-yl]-5-methyl-nicotinamide,
6-amino-N-[1-(3,5-diethoxy-4-fluoro-benzyl)-piperidin-4-yl]-5-methyl-nicotinamide,
6-amino-N-[1-(2-ethoxy-4'-trifluoromethyl-biphenyl-4-ylmethyl)-piperidin-4-yl]-5-methyl-nicotinamide,
6-amino-N-[1-(3-ethoxy-4-pyridin-4-yl-benzyl)-piperidin-4-yl]-nicotinamide,
N-[1-(4-chloro-3-ethoxy-benzyl)-piperidin-4-yl]-6-methylamino-nicotinamide, N-[1-(3-ethoxy-4-methyl-benzyl)-piperidin-4-yl]-6-methylamino-nicotinamide,
N-[1-(3-ethoxy-4-pyridin-3-yl-benzyl)-piperidin-4-yl]-6-methylamino-nicotinamide,
N-[1-(3,5-diethoxy-4-fluoro-benzyl)-piperidin-4-yl]-5-methyl-6-methylamino-nicotinamide,
N-[1-(3,5-diisopropoxy-benzyl)-piperidin-4-yl]-5-methyl-6-methylamino-nicotinamide,
N-[1-(2-ethoxy-4'-fluoro-biphenyl-4-ylmethyl)-piperidin-4-yl]-5-methyl-6-methylamino-nicotinamide,
N-[1-(3-ethoxy-4-imidazol-1-yl-benzyl)-piperidin-4-yl]-5-methyl-nicotinamide,
N-[1-(3,5-diethoxy-4-imidazol-1-yl-benzyl)-piperidin-4-yl]-5-methyl-nicotinamide,
N-[1-(3,5-diisopropoxy-benzyl)-piperidin-4-yl]-2,6-dimethyl-terephthalamic acid,
N-[1-(3,5-diethoxy-4-pyrrol-1-yl-benzyl)-piperidin-4-yl]-2,6-dimethyl-terephthalamic acid,
N-[1-(3,5-diethoxy-4-fluoro-benzyl)-piperidin-4-yl]-2,6-dimethyl-terephthalamic acid,
2-{4-[1-(3,5-diethoxy-4-[1,2,4]triazol-1-yl-benzyl)-piperidin-4-ylcarbamoyl]-phenyl}-2-methyl-propionic acid methyl ester,
2-{4-[1-(3,5-diethoxy-4-[1,2,4]triazol-1-yl-benzyl)-piperidin-4-ylcarbamoyl]-phenyl}-2-methyl-propionic acid,
N-[1-(3,5-diisopropoxy-benzyl)-piperidin-4-yl]-6-methylamino-nicotinamide,
N-[1-(3,5-diethoxy-4-fluoro-benzyl)-piperidin-4-yl]-6-dimethylamino-5-methyl-nicotinamide,
N-[1-(4-chloro-3-ethoxy-benzyl)-piperidin-4-yl]-6-dimethylamino-5-methyl-nicotinamide,
N-[1-(3,5-diisopropoxy-benzyl)-piperidin-4-yl]-6-dimethylamino-5-methyl-nicotinamide,
6-dimethylamino-N-[1-(3-ethoxy-4-methyl-benzyl)-piperidin-4-yl]-5-methyl-nicotinamide,
6-dimethylamino-N-[1-(2-ethoxy-4'-fluoro-biphenyl-4-ylmethyl)-piperidin-4-yl]-5-methyl-nicotinamide,
N-[1-(3-ethoxy-4-imidazol-1-yl-benzyl)-piperidin-4-yl]-3-methanesulfonyl-benzamide,
N-[1-(3,5-diethoxy-4-imidazol-1-yl-benzyl)-piperidin-4-yl]-3-methanesulfonyl-benzamide,
N-[1-(2,6-diethoxy-4'-trifluoromethyl-biphenyl-4-ylmethyl)-piperidin-4-yl]-6-methylamino-nicotinamide,
N-[1-(2,6-diethoxy-4'-fluoro-biphenyl-4-ylmethyl)-piperidin-4-yl]-6-methylamino-nicotinamide,
N-[1-(3,5-diethoxy-4-imidazol-1-yl-benzyl)-piperidin-4-yl]-6-methylamino-nicotinamide,
methanesulfonic acid 3-[1-(3-ethoxy-4-imidazol-1-yl-benzyl)-piperidin-4-ylcarbamoyl]-phenyl ester,
N-[1-(3,5-diethoxy-4-fluoro-benzyl)-piperidin-4-yl]-5-methoxy-isophthalamic acid methyl ester,
N-[1-(3,5-diethoxy-4-pyrrol-1-yl-benzyl)-piperidin-4-yl]-5-methoxy-isophthalamic acid methyl ester,
N-[1-(3,5-diisopropoxy-benzyl)-piperidin-4-yl]-5-methoxy-isophthalamic acid methyl ester,
N-[1-(3,5-diethoxy-4-fluoro-benzyl)-piperidin-4-yl]-5-methoxy-isophthalamic acid,
N-[1-(3,5-diethoxy-4-pyrrol-1-yl-benzyl)-piperidin-4-yl]-5-methoxy-isophthalamic acid,
N-[1-(3,5-diisopropoxy-benzyl)-piperidin-4-yl]-5-methoxy-isophthalamic acid,
N-[1-(3,5-diethoxy-4-imidazol-1-yl-benzyl)-piperidin-4-yl]-6-dimethylamino-5-methyl-nicotinamide,
6-chloro-N-[1-(3,5-diisopropoxy-benzyl)-piperidin-4-yl]-nicotinamide,
6-chloro-N-[1-(3-ethoxy-4-methyl-benzyl)-piperidin-4-yl]-nicotinamide,
N-[1-(2,6-diethoxy-biphenyl-4-ylmethyl)-piperidin-4-yl]-5-methyl-nicotinamide,
N-[1-(2,6-diethoxy-4'-fluoro-biphenyl-4-ylmethyl)-piperidin-4-yl]-5-methyl-nicotinamide,
6-chloro-N-[1-(2,6-diethoxy-4'-fluoro-biphenyl-4-ylmethyl)-piperidin-4-yl]-nicotinamide,
6-chloro-N-[1-(2-ethoxy-4'-fluoro-biphenyl-4-ylmethyl)-piperidin-4-yl]-nicotinamide,
N-[1-(2,6-diethoxy-biphenyl-4-ylmethyl)-piperidin-4-yl]-6-methylamino-nicotinamide,
6-amino-N-[1-(3,5-diethoxy-4-imidazol-1-yl-benzyl)-piperidin-4-yl]-5-methyl-nicotinamide,
N-[1-(4-cyclopropyl-3,5-diethoxy-benzyl)-piperidin-4-yl]-5-methyl-nicotinamide,
6-chloro-N-[1-(3,5-diethoxy-4-fluoro-benzyl)-piperidin-4-yl]-nicotinamide,
N-[1-(3,5-diethoxy-4-fluoro-benzyl)-piperidin-4-yl]-6-isopropylamino-nicotinamide,
N-[1-(3-ethoxy-4-methyl-benzyl)-piperidin-4-yl]-6-isopropylamino-nicotinamide,
N-[1-(3,5-diisopropoxy-benzyl)-piperidin-4-yl]-6-isopropylamino-nicotinamide,
N-[1 (2-ethoxy-4'-fluoro-biphenyl-4-ylmethyl)-piperidin-4-yl]-6-isopropylamino-nicotinamide,
N-[1-(4-cyclopropyl-3-ethoxy-benzyl)-piperidin-4-yl]-5-methyl-nicotinamide,
6-amino-N-[1-(4-cyclopropyl-3-ethoxy-benzyl)-piperidin-4-yl]-nicotinamide,
N-[1-(4-cyclopropyl-3-ethoxy-benzyl)-piperidin-4-yl]-6-methylamino-nicotinamide,
6-amino-N-[1-(2,6-diethoxy-4'-fluoro-biphenyl-4-ylmethyl)-piperidin-4-yl]-nicotinamide,
4-{3-[1-(3,5-diethoxy-4-fluoro-benzyl)-piperidin-4-ylcarbamoyl]-5-methoxy-phenoxy}-butyric acid methyl ester,
4-{3-[1-(3,5-diisopropoxy-benzyl)-piperidin-4-ylcarbamoyl]-5-methoxy-phenoxy}-butyric acid methyl ester,
N-[1-(3,5-diethoxy-4-fluoro-benzyl)-piperidin-4-yl]-3-methoxy-5-(1H-tetrazol-5-ylmethoxy)-benzamide,
N-[1-(3,5-diethoxy-4-pyrrol-1-yl-benzyl)-piperidin-4-yl]-3-methoxy-5-(1H-tetrazol-5-ylmethoxy)-benzamide,
N-[1-(3,5-diisopropoxy-benzyl)-piperidin-4-yl]-3-methoxy-5-(1H-tetrazol-5-ylmethoxy)-benzamide,
4-{3-[1-(3,5-diethoxy-4-fluoro-benzyl)-piperidin-4-ylcarbamoyl]-5-methoxy-phenoxy}-butyric acid,
4-{3-[1-(3,5-diisopropoxy-benzyl)-piperidin-4-ylcarbamoyl]-5-methoxy-phenoxy}-butyric acid,
rac-3-(2,3-dihydroxy-propoxy)-N-[1-(3,5-diisopropoxy-benzyl)-piperidin-4-yl]-5-methoxy-benzamide,
rac-N-[1-(3,5-diethoxy-4-pyrrol-1-yl-benzyl)-piperidin-4-yl]-3-(2,3-dihydroxy-propoxy)-5-methoxy-benzamide,
rac-N-[1-(3,5-diethoxy-4-fluoro-benzyl)-piperidin-4-yl]-3-(2,3-dihydroxy-propoxy)-5-methoxy-benzamide,
N-[1-(3,5-diethoxy-4-fluoro-benzyl)-piperidin-4-yl]-3-(2H-tetrazol-5-yl)-benzamide,
6-amino-N-[1-(3,5-diethoxy-4-imidazol-1-yl-benzyl)-piperidin-4-yl]-nicotinamide,
N-[1-(4-cyclopropyl-3,5-diethoxy-benzyl)-piperidin-4-yl]-6-methylamino-nicotinamide,
6-amino-N-[1-(4-cyclopropyl-3,5-diethoxy-benzyl)-piperidin-4-yl]-5-methyl-nicotinamide,
methanesulfonic acid 3-[1-(4-cyclopropyl-3,5-diethoxy-benzyl)-piperidin-4-ylcarbamoyl]-phenyl ester,
N-[1-(4-cyclopropyl-3-ethoxy-benzyl)-piperidin-4-yl]-3-methanesulfonyl-benzamide,
N-[1-(2,6-diethoxy-4'-fluoro-biphenyl-4-ylmethyl)-piperidin-4-yl]-6-isopropylamino-nicotinamide, 6-amino-N-[1-(2,6-diethoxy-biphenyl-4-ylmethyl)-piperidin-4-yl]-nicotinamide,
N-[1-(4-cyclopropyl-3-ethoxy-benzyl)-piperidin-4-yl]-6-isopropylamino-nicotinamide,
N-[1-(4-Cyclopropyl-3,5-diethoxy-benzyl)-piperidin-4-yl]-3-methanesulfonyl-benzamide
6-cyclopropylamino-N-[1-(3,5-diethoxy-4-fluoro-benzyl)-piperidin-4-yl]-nicotinamide,
6-cyclopropylamino-N-[1-(3,5-diisopropoxy-benzyl)-piperidin-4-yl]-nicotinamide,
6-cyclopropylamino-N-[1-(3-ethoxy-4-methyl-benzyl)-piperidin-4-yl]-nicotinamide,
6-cyclopropylamino-N-[1-(2-ethoxy-4'-fluoro-biphenyl-4-ylmethyl)-piperidin-4-yl]-nicotinamide,
N-[1-(4-cyclopropyl-3,5-diethoxy-benzyl)-piperidin-4-yl]-5-methyl-6-methylamino-nicotinamide,
N-[1-(2,6-diethoxy-biphenyl-4-ylmethyl)-piperidin-4-yl]-5-methyl-6-methylamino-nicotinamide,
6-cyclopropylamino-N-[1-(4-cyclopropyl-3-ethoxy-benzyl)-piperidin-4-yl]-nicotinamide,
N-[1-(2,6-diethoxy-4'-fluoro-biphenyl-4-ylmethyl)-piperidin-4-yl]-5-methyl-6-methylamino-nicotinamide,
N-[1-(4-cyclopropyl-3-ethoxy-benzyl)-piperidin-4-yl]-5-methyl-6-methylamino-nicotinamide,
6-cyclopropylamino-N-[1-(4-cyclopropyl-3,5-diethoxy-benzyl)-piperidin-4-yl]-nicotinamide,
N-[1-(3,5-diethoxy-4-[1,2,4]triazol-1-yl-benzyl)-piperidin-4-yl]-3-(2H-tetrazol-5-yl)-benzamide,
N-[1-(3,5-diisopropoxy-benzyl)-piperidin-4-yl]-3-(2H-tetrazol-5-yl)-benzamide,
N-[1-(3,5-diethoxy-4-pyrrol-1-yl-benzyl)-piperidin-4-yl]-3-(2H-tetrazol-5-yl)-benzamide,
6-cyclopropylamino-N-[1-(2,6-diethoxy-4'-fluoro-biphenyl-4-ylmethyl)-piperidin-4-yl]-nicotinamide,
N-[1-(4-cyclopropyl-3,5-diethoxy-benzyl)-piperidin-4-yl]-3,5-dimethoxy-benzamide,
N-[1-(2,6-diethoxy-4'-fluoro-biphenyl-4-ylmethyl)-piperidin-4-yl]-3,5-dimethoxy-benzamide,
N-[1-(3-ethoxy-4-methyl-benzyl)-piperidin-4-yl]-3,5-dimethoxy-benzamide,
N-[1-(4-cyclopropyl-3-ethoxy-benzyl)-piperidin-4-yl]-3,5-dimethoxy-benzamide,
N-[1-(2-ethoxy-4'-fluoro-biphenyl-4-ylmethyl)-piperidin-4-yl]-3,5-dimethoxy-benzamide,
N-[1-(3,5-diisopropoxy-benzyl)-piperidin-4-yl]-3,5-dimethoxy-benzamide,
N-[1-(3,5-diethoxy-4-fluoro-benzyl)-piperidin-4-yl]-3,5-dimethoxy-benzamide,
N-[1-(2,6-diethoxy-biphenyl-4-ylmethyl)-piperidin-4-yl]-3,5-bis-(2-fluoro-ethoxy)-benzamide,
N-[1-(3-ethoxy-4-methyl-benzyl)-piperidin-4-yl]-3,5-bis-(2-fluoro-ethoxy)-benzamide,
N-[1-(3,5-diethoxy-4-fluoro-benzyl)-piperidin-4-yl]-3,5-bis-(2-fluoro-ethoxy)-benzamide,
N-[1-(4-cyclopropyl-3,5-diethoxy-benzyl)-piperidin-4-yl]-3,5-bis-(2-fluoro-ethoxy)-benzamide,
N-[1-(4-chloro-3-ethoxy-benzyl)-piperidin-4-yl]-3,5-bis-(2-fluoro-ethoxy)-benzamide,
N-[1-(3,5-diisopropoxy-benzyl)-piperidin-4-yl]-3,5-bis-(2-fluoro-ethoxy)-benzamide,
N-[1-(2,6-diethoxy-4'-fluoro-biphenyl-4-ylmethyl)-piperidin-4-yl]-3,5-bis-(2-fluoro-ethoxy)-benzamide,
N-[1-(2-ethoxy-4'-fluoro-biphenyl-4-ylmethyl)-piperidin-4-yl]-3,5-bis-(2-fluoro-ethoxy)-benzamide,
N-[1-(3,5-diethoxy-4-fluoro-benzyl)-piperidin-4-yl]-3-hydroxymethyl-5-methoxy-benzamide,
N-[1-(3,5-diisopropoxy-benzoyl)-piperidin-4-yl]-3-hydroxymethyl-5-methoxy-benzamide,
N-[1-(4-chloro-3,5-diethoxy-benzyl)-piperidin-4-yl]-3-hydroxymethyl-5-methoxy-benzamide,
N-[1-(2,6-diethoxy-4'-fluoro-biphenyl-4-ylmethyl)-piperidin-4-yl]-3-hydroxymethyl-5-methoxy-benzamide,
6-chloro-N-[1-(4-chloro-3,5-diethoxy-benzyl)-piperidin-4-yl]-nicotinamide,
6-chloro-N-[1-(4-cyclopropyl-3,5-diethoxy-benzyl)-piperidin-4-yl]-nicotinamide,
3-cyclopropyl-N-[1-(3-ethoxy-4-pyridin-4-yl-benzyl)-piperidin-4-yl]-5-methoxy-benzamide,
3-cyclopropyl-N-[1-(4-cyclopropyl-3,5-diethoxy-benzyl)-piperidin-4-yl]-5-methoxy-benzamide,
3-cyclopropyl-N-[1-(3,5-diethoxy-4-fluoro-benzyl)-piperidin-4-yl]-5-methoxy-benzamide,
3-cyclopropyl-N-[1-(2,6-diethoxy-4'-fluoro-biphenyl-4-ylmethyl)-piperidin-4-yl]-5-methoxy-benzamide,
6-chloro-N-[1-(3,5-diethoxy-4-pyrrol-1-yl-benzyl)-piperidin-4-yl]-nicotinamide,
N-[1-(2,6-diethoxy-4'-fluoro-biphenyl-4-ylmethyl)-piperidin-4-yl]-3-methoxy-5-pyridin-4-yl-benzamide,
4'-fluoro-5-methoxy-biphenyl-3-carboxylic acid[1-(2,6-diethoxy-4'-fluoro-biphenyl-4-ylmethyl)-piperidin-4-yl]-amide,
4'-fluoro-5-methoxy-biphenyl-3-carboxylic acid[1-(3,5-diethoxy-4-fluoro-benzyl)-piperidin-4-yl]-amide,
4'-fluoro-5-methoxy-biphenyl-3-carboxylic acid[1-(2-ethoxy-4'-fluoro-biphenyl-4-ylmethyl)-piperidin-4-yl]-amide,
4'-fluoro-5-methoxy-biphenyl-3-carboxylic acid[1-(3-ethoxy-4-methyl-benzyl)-piperidin-4-yl]-amide,
4'-fluoro-5-methoxy-biphenyl-3-carboxylic acid[1-(4-cyclopropyl-3,5-diethoxy-benzyl)-piperidin-4-yl]-amide,
4'-fluoro-5-methoxy-biphenyl-3-carboxylic acid[1-(3,5-diisopropoxy-benzyl)-piperidin-4-yl]-amide,
N-[1-(4-chloro-3,5-diethoxy-benzyl)-piperidin-4-yl]-5-methoxy-isophthalamic acid methyl ester,
N-[1-(2,6-diethoxy-4'-fluoro-biphenyl-4-ylmethyl)-piperidin-4-yl]-5-methoxy-isophthalamic acid methyl ester,
N-[1-(4-chloro-3,5-diethoxy-benzyl)-piperidin-4-yl]-5-methoxy-isophthalamic acid,
N-[1-(2,6-diethoxy-4'-fluoro-biphenyl-4-ylmethyl)-piperidin-4-yl]-5-methoxy-isophthalamic acid,
N-[1-(4-chloro-3,5-diethoxy-benzyl)-piperidin-4-yl]-6-methylamino-nicotinamide,
N-[1-(2,6-diethoxy-3',5'-difluoro-biphenyl-4-ylmethyl)-piperidin-4-yl]-5-methyl-nicotinamide,
N-[1-(3,5-diisopropoxy-benzyl)-piperidin-4-yl]-3-methoxy-5-pyridin-3-yl-benzamide,
N-[1-(3,5-diethoxy-4-fluoro-benzyl)-piperidin-4-yl]-3-methoxy-5-pyridin-3-yl-benzamide,
N-[1-(2,6-diethoxy-4'-fluoro-biphenyl-4-ylmethyl)-piperidin-4-yl]-3-methoxy-5-pyridin-3-yl-benzamide,
N-[1-(2,6-diethoxy-4'-trifluoro-methoxy-biphenyl-4-ylmethyl)-piperidin-4-yl]-5-methyl-nicotinamide,
3-cyanomethoxy-N-[1-(3,5-diethoxy-4-fluoro-benzyl)-piperidin-4-yl]-5-methoxy-benzamide,
N-[1-(4-chloro-3,5-diethoxy-benzyl)-piperidin-4-yl]-3-cyanomethoxy-5-methoxy-benzamide,
3-cyanomethoxy-N-[1-(2,6-diethoxy-4'-fluoro-biphenyl-4-ylmethyl)-piperidin-4-yl]-5-methoxy-benzamide,
rac-N-[1-(4-chloro-3,5-diethoxy-benzyl)-piperidin-4-yl]-3-(2,3-dihydroxy-propoxy)-5-methoxy-benzamide,
rac-N-[1-(2,6-diethoxy-4'-fluoro-biphenyl-4-ylmethyl)-piperidin-4-yl]-3-(2,3-dihydroxy-propoxy)-5-methoxy-benzamide, 3-carbamoylmethoxy-N-[1-(3,5-diethoxy-4-fluoro-benzyl)-piperidin-4-yl]-5-methoxy-benzamide,
3-carbamoylmethoxy-N-[1-(4-chloro-3,5-diethoxy-benzyl)-piperidin-4-yl]-5-methoxy-benzamide,
3-carbamoylmethoxy-N-[1-(2,6-diethoxy-4'-fluoro-biphenyl-4-ylmethyl)-piperidin-4-yl]-5-methoxy-benzamide,
6-cyano-N-[1-(2,6-diethoxy-4'-fluoro-biphenyl-4-ylmethyl)-piperidin-4-yl]-5-methyl-nicotinamide,
N-[1-(4-chloro-3,5-diethoxy-benzyl)-piperidin-4-yl]-6-cyano-5-methyl-nicotinamide,
6-cyano-N-[1-(3,5-diethoxy-4-fluoro-benzyl)-piperidin-4-yl]-5-methyl-nicotinamide,
6-chloro-N-[1-(2,6-diethoxy-4'-trifluoromethoxy-biphenyl-4-ylmethyl)-piperidin-4-yl]-nicotinamide,
N-[1-(3,5-diethoxy-4-fluoro-benzyl)-piperidin-4-yl]-3-hydroxy-5-methoxy-benzamide,
N-[1-(4-chloro-3,5-diethoxy-benzyl)-piperidin-4-yl]-3-hydroxy-5-methoxy-benzamide,
N-[1-(2,6-diethoxy-4'-fluoro-biphenyl-4-ylmethyl)-piperidin-4-yl]-3-hydroxy-5-methoxy-benzamide,
methanesulfonic acid 3-[1-(3,5-diethoxy-4-fluoro-benzyl)-piperidin-4-ylcarbamoyl]-5-methoxy-phenyl ester,
methanesulfonic acid 3-[1-(4-chloro-3,5-diethoxy-benzyl)-piperidin-4-ylcarbamoyl]-5-methoxy-phenyl ester,
methanesulfonic acid 3-[1-(2,6-diethoxy-4'-fluoro-biphenyl-4-ylmethyl)-piperidin-4-ylcarbamoyl]-5-methoxy-phenyl ester,
{3-[1-(2,6-diethoxy-4'-fluoro-biphenyl-4-ylmethyl)-piperidin-4-ylcarbamoyl]-5-methoxy-phenoxy}-acetic acid ethyl ester,
{3-[1-(4-chloro-3,5-diethoxy-benzyl)-piperidin-4-ylcarbamoyl]-5-methoxy-phenoxy}-acetic acid ethyl ester,
{3-[1-(2,6-diethoxy-4'-fluoro-biphenyl-4-ylmethyl)-piperidin-4-ylcarbamoyl]-5-methoxy-phenoxy}-acetic acid,
{3-[1-(4-chloro-3,5-diethoxy-benzyl)-piperidin-4-ylcarbamoyl]-5-methoxy-phenoxy}-acetic acid, and pharmaceutically acceptable salts thereof.

Particularly preferred compounds of formula I of the present invention are the following:
N-[1-(4-chloro-3-ethoxy-benzyl)piperidin-4-yl]-3-methanesulfonylbenzamide,
N-[1-(4-chloro-3-ethoxy-benzyl)piperidin-4-yl]-3-methyl-benzamide,
N-[1-(4-chloro-3-ethoxy-benzyl)piperidin-4-yl]-6-methyl-nicotinamide,
6-amino-N-[1-(4-chloro-3-ethoxy-benzyl)piperidin-4-yl]-nicotinamide,
N-[1-(4-chloro-3-ethoxy-benzyl)piperidin-4-yl]-5-methyl-nicotinamide,
N-{1-[3-ethoxy-5-(tetrahydro-pyran-4-yl-oxy)-benzyl]piperidin-4-yl}-5-methyl-nicotinamide,
N-[1-(3-ethoxy-4-methyl-benzyl)piperidin-4-yl]-5-methyl-nicotinamide,
N-[1-(3-ethoxy-4-methoxy-benzyl)piperidin-4-yl]-5-methyl-nicotinamide,
N-[1-(3-ethoxy-4-methoxy-2-pyridine-4-yl-)piperidin-4-yl-benzyl]-5-methyl-nicotinamide N-[1-(3-ethoxy-4-methoxy-2-pyrimidin-5-yl-benzyl)piperidin-4-yl]-5-methyl-nicotinamide, and pharmaceutically acceptable salts thereof.

More preferred compounds of formula I of the present invention are the following:
N-[1-(2-ethoxy-4'-fluoro-biphenyl-4-ylmethyl)-piperidin-4-yl]-5-methyl-nicotinamide,
N-[1-(2-ethoxy-4'-fluoro-biphenyl-4-ylmethyl)-piperidin-4-yl]-6-methylamino-nicotinamide,
N-[1-(3,5-diethoxy-4-imidazol-1-yl-benzyl)-piperidin-4-yl]-5-methyl-nicotinamide,
N-[1-(3,5-diethoxy-4-pyrrol-1-yl-benzyl)-piperidin-4-yl]-2,6-dimethyl-terephthalamic acid,
N-[1-(2,6-diethoxy-4'-fluoro-biphenyl-4-ylmethyl)-piperidin-4-yl]-6-methylamino-nicotinamide,
N-[1-(2,6-diethoxy-4'-fluoro-biphenyl-4-ylmethyl)-piperidin-4-yl]-5-methyl-nicotinamide,
6-chloro-N-[1-(2,6-diethoxy-4'-fluoro-biphenyl-4-ylmethyl)-piperidin-4-yl]-nicotinamide,
6-amino-N-[1-(2,6-diethoxy-4'-fluoro-biphenyl-4-ylmethyl)-piperidin-4-yl]-nicotinamide,
N-[1-(2,6-diethoxy-4'-fluoro-biphenyl-4-ylmethyl)-piperidin-4-yl]-6-isopropylamino-nicotinamide,
N-[1-(2,6-diethoxy-4'-fluoro-biphenyl-4-ylmethyl)-piperidin-4-yl]-3-hydroxymethyl-5-methoxy-benzamide,
N-[1-(4-chloro-3,5-diethoxy-benzyl)-piperidin-4-yl]-5-methoxy-isophthalamic acid,
N-[1-(2,6-diethoxy-4'-fluoro-biphenyl-4-ylmethyl)-piperidin-4-yl]-5-methoxy-isophthalamic acid,
N-[1-(2,6-diethoxy-3',5'-difluoro-biphenyl-4-ylmethyl)-piperidin-4-yl]-5-methyl-nicotinamide,
3-cyanomethoxy-N-[1-(2,6-diethoxy-4'-fluoro-biphenyl-4-ylmethyl)-piperidin-4-yl]-5-methoxy-benzamide,
rac-N-[1-(2,6-diethoxy-4'-fluoro-biphenyl-4-ylmethyl)-piperidin-4-yl]-3-(2,3-dihydroxy-propoxy)-5-methoxy-benzamide,
3-carbamoylmethoxy-N-[1-(2,6-diethoxy-4'-fluoro-biphenyl-4-ylmethyl)-piperidin-4-yl]-5-methoxy-benzamide,
6-cyano-N-[1-(2,6-diethoxy-4'-fluoro-biphenyl-4-ylmethyl)-piperidin-4-yl]-5-methyl-nicotinamide,
{3-[1-(2,6-diethoxy-4'-fluoro-biphenyl-4-ylmethyl)-piperidin-4-ylcarbamoyl]-5-methoxy-phenoxy}-acetic acid,
and pharmaceutically acceptable salts thereof.

Furthermore, the pharmaceutically acceptable salts of the compounds of formula I individually constitute preferred embodiments of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula (I) as defined above, which process comprises reacting a compound of the general formula

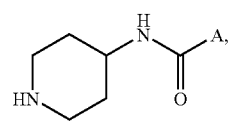

II wherein A is as defined herein before, with an aldehyde of the formula

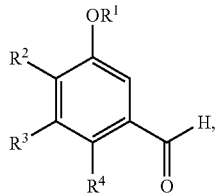
III wherein $R^1$, $R^2$, $R^3$ and $R^4$ are as defined herein before, by employing a reducing agent to obtain a compound of the formula

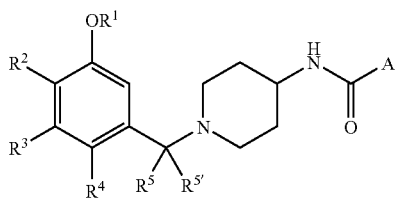
I-A wherein $R^5$ and $R^{5'}$ are hydrogen, and, if desired, converting the compound of formula I into a pharmaceutically acceptable salt, or, alternatively, reacting a compound of the general formula

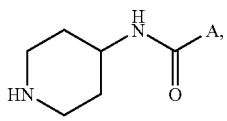
II wherein A is as defined herein before, with an alkyl halide of the formula

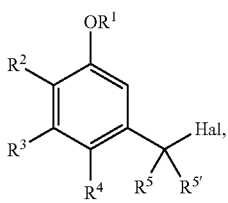
IV wherein $R^1$ to $R^5$ and $R^{5'}$ are as defined herein before and Hal is halogen, with the addition of a suitable base to obtain a compound of the formula

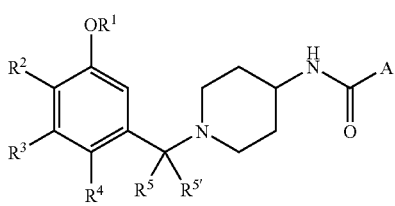
I and, if desired, converting the compound of formula I into a pharmaceutically acceptable salt, or, alternatively, coupling an amine of the general formula

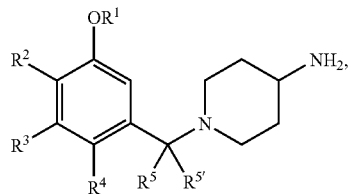
V wherein $R^1$ to $R^5$ and $R^{5'}$ are as defined herein before, with a carboxylic acid of the formula

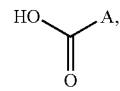
VI wherein A is as defined herein before, by employing a suitable coupling agent to obtain a compound of the formula

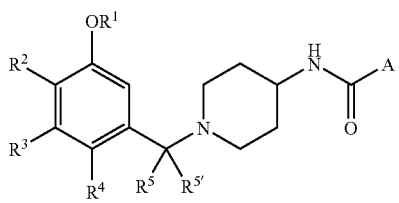
I and, if desired, converting the compound of formula I into a pharmaceutically acceptable salt, or, alternatively, coupling an amine of the general formula

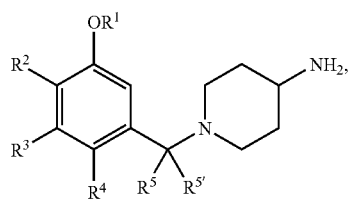
V wherein $R^1$ to $R^5$ and $R^{5'}$ are as defined herein before, with an acid chloride of the formula

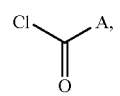
VII wherein A is as defined herein before, with the addition of a suitable base to obtain a compound of the formula

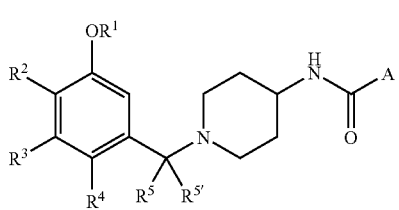
I and, if desired, converting the compound of formula I into a pharmaceutically acceptable salt.

The invention further relates to compounds of formula I as defined above, when manufactured according to a process as defined above.

Suitable reducing agents are preferably selected from the group consisting of pyridine-$BH_3$ complex, $NaBH(OAc)_3$ and $NaCNBH_3$. The reaction can be carried out under acidic conditions by using an acid such as acetic acid or formic acid or an Lewis acid (e.g. $Ti(iPrO)_4$, $ZnCl_2$) or under basic conditions (no additive) in a suitable solvent such as dichloromethane, dichloroethane, isopropanol or ethanol (or mixtures thereof) at ambient or elevated temperatures using conventional heating or heating by microwave irradiation.

Suitable bases are preferably selected from the group consisting of tertiary amine bases such as triethylamine ($Et_3N$), diethyl isopropylamine ($iPrNEt_2$) and diisopropyl ethyl amine (DIPEA) and inorganic bases such as potassium carbonate ($K_2CO_3$).

Suitable coupling agents for the reaction of carboxylic acids with amines are N,N'-carbonyldiimidazole (CDI), N,N'-dicyclohexylcarbodiimide (DCC), 1-(3-dimethyl-aminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyl-uronium tetrafluoroborate (TBTU), (benzotriazol-1-yloxy)-tris-(dimethylamino)-phosphonium-hexafluorophosphate (BOP) and the like. Preferred coupling agents are selected from the group consisting of 1-(3-dimethylaminopropyl)-3-ethylcarbodiimide hydrochloride (EDCI), N,N'-carbonyldiimidazole (CDI) and (benzotriazol-1-yloxy)-tris-(dimethylamino)-phosphonium-hexafluorophosphate (BOP).

As described above, the compounds of formula (I) of the present invention can be used as medicaments for the treatment and/or prevention of diseases which are associated with the modulation of SST receptors subtype 5.

"Diseases which are associated with the modulation of SST receptors subtype 5" are such diseases as diabetes mellitus, particularly type 2 diabetes mellitus, impaired fasting glucose, impaired glucose tolerance, micro- and macrovascular diabetic complications, posttransplantation diabetes mellitus in patients having type 1 diabetes mellitus, gestational diabetes, obesity, inflammatory bowel diseases such as Crohn's disease or ulcerative colitis, gastrointestinal motility disorders, malabsorption, autoimmune diseases such as rheumatoid arthritis, osteoarthritis, psoriasis and other skin disorders, and immunodeficiences. Microvascular diabetic complications include diabetic nephropathy, diabetic neuropathy and diabetic retinopathy, whereas macrovascular diabetes-associated complications lead to an increased risk for myocardial infarction, stroke and limb amputations. Gastrointestinal motility disorders include gastrointestinal motility disorders associated with reduced motility (e.g., gastroparesis, ileus, constipation).

The use as medicament for the treatment and/or prevention of diabetes mellitus, particularly type 2 diabetes mellitus, impaired fasting glucose or impaired glucose tolerance is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of SST receptors subtype 5.

In another embodiment, the invention relates to a method for the treatment and/or prevention of diseases which are associated with the modulation of SST receptors subtype 5, which method comprises administering a compound of formula I to a human or animal.

The invention further relates to the use of compounds as defined above for the treatment and/or prevention of diseases which are associated with the modulation of SST receptors subtype 5.

In addition, the invention relates to the use of compounds as defined above for the preparation of medicaments for the treatment and/or prevention of diseases which are associated with the modulation of SST receptors subtype 5.

The compounds of formula I can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

The synthesis of compounds of the general formula I, can be accomplished according to scheme 1, scheme 2 or scheme 3, respectively. Methods for the synthesis of the intermediate aldehydes are described in scheme 4 and scheme 5.

A suitably protected form of 4-amino-piperidine 1 (P means protecting group), e.g., protected by benzyl or as tert-butyl-, or ethyl carbamate (see Protective Groups in Organic Synthesis, T. W. Greene, Wiley-Interscience 1999) can be first coupled with a carboxylic acid of formula 2 (X=OH) by employing a suitable coupling agent such as for example 1-(3-dimethylaminopropyl)-3-ethylcarbodiimide hydrochloride (EDCI), N,N'-carbonyldiimidazole (CDI) or (benzotriazol-1-yloxy)-tris-(dimethylamino)-phosphonium-hexafluorophosphate (BOP) and a suitable base, e.g., N,N-diisopropyl-ethylamine (DIPEA), typically in a solvent such as dimethylformamide (DMF), dichloromethane (DCM), dichloroethane (DCE), or tetrahydrofuran (THF) at room or elevated temperature. Alternatively, the protected 4-amino-piperidine 1 can be coupled with an acid chloride of formula 2 (X=Cl) by employing a suitable tertiary amine base such as e.g., $Et_3N$, $iPrNEt_2$ or DIPEA in DCM, DCE or DMF at room or ice-bath temperature to afford the amide 3 (scheme 1, step a). The protecting group can then be removed (step b) by, depending on the group used, e.g., hydrogenation or acid treatment (see Protective Groups in Organic Synthesis above). The liberated amine II can then be alkylated (step c):

by reaction with an aldehydes III under reductive amination conditions (employing a suitable reducing agent such as py-$BH_3$ complex, $NaBH(OAc)_3$, $NaCNBH_3$ under acidic (e.g., acetic acid or $Ti(iPrO)_4$ or $ZnCl_2$ as additive) or under basic conditions (no additive) in a solvent such as dichloromethane (DCM), DCE, ethanol, isopropanol or mixtures thereof at ambient or elevated temperature, or by direct alkylation with alkyl halides IV in solvents such as DMF or DCE at ambient or elevated temperature in the presence of a suitable tertiary amine base (e.g. $Et_3N$, $iPrNEt_2$) or inorganic base (e.g. $K_2CO_3$).

In case the aromatic moiety A is substituted by an ester function, the latter can subsequently be saponified by methods well known in the art to liberate the free carboxylic acid which can form a zwitter ion together with the tertiary amino function present in the piperidine moiety.

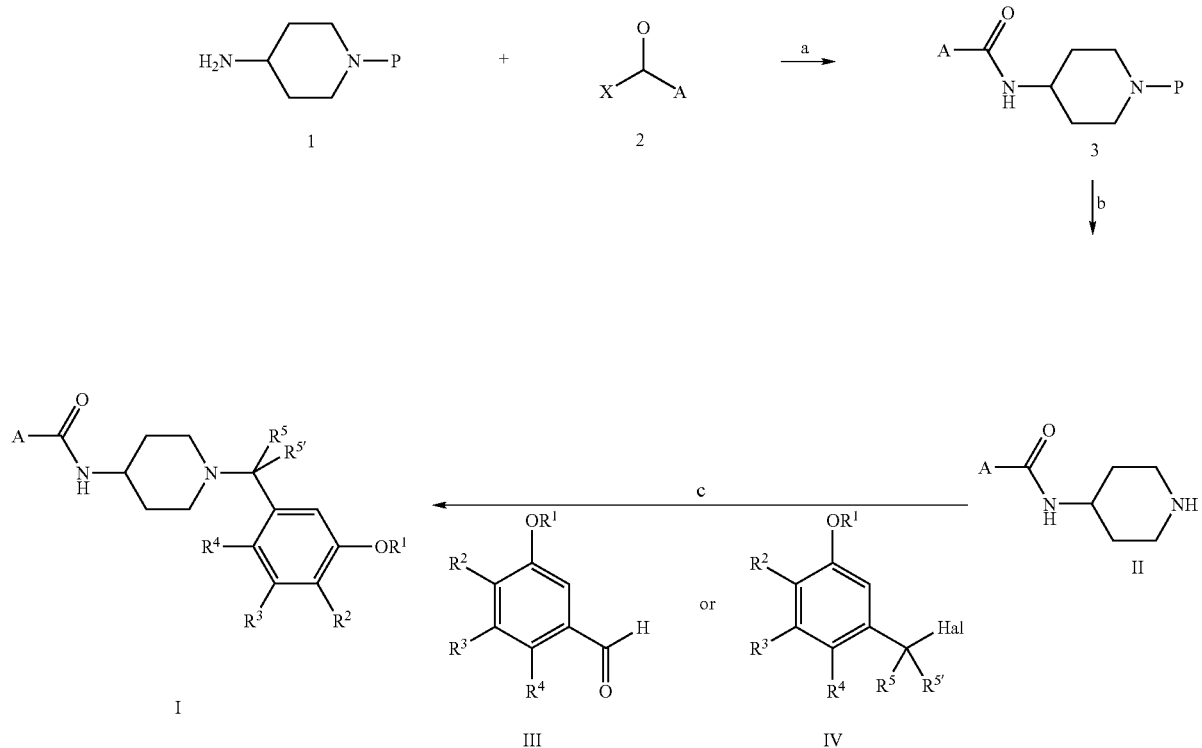

Alternatively, the reaction sequence can be performed in reverse order according to scheme 2, namely first performing the alkylation (as previously described) with the secondary amino group of a suitably protected 4-amino piperidine (step a), e.g., using a tert-butylcarbamate protective group (see Protective Groups in Organic Synthesis above). Subsequent removal of the protecting group (step b) and coupling of the liberated amine V with a carboxylic acid VI or an acid chloride VII as described before affords the desired compounds I (step c).

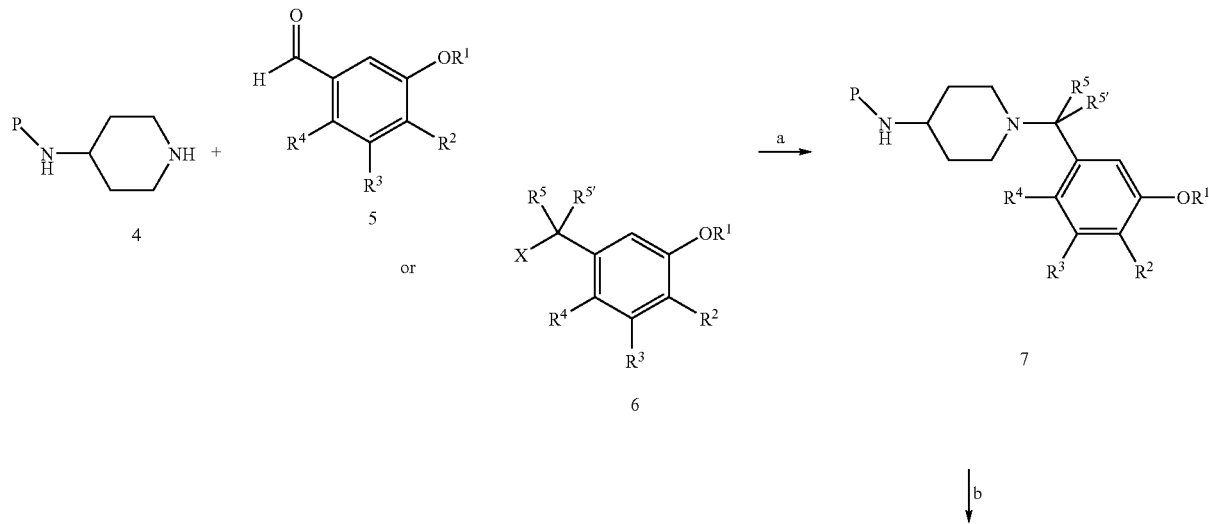

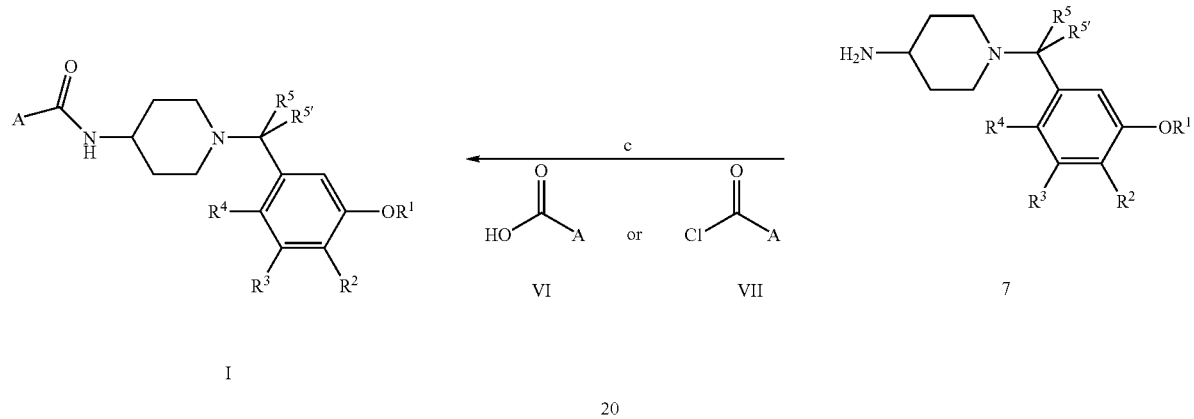

Hydroxy substituted amides 8 (scheme 3) react with suitable halides, mesylates, tosylates or alcohols transformed into any other suitable leaving group in a polar solvent such as N,N-dimethylformamide or acetone and a suitable base (e.g., $Cs_2CO_3$, $K_2CO_3$) at room or elevated temperature, by Mitsunobu reaction with alcohols activated by a mixture of triphenylphosphine and diethyl- or di-tert-butyl-azodicarboxylate, or by analogous alkylation reactions giving modified amide compounds 9 (step a). The transformation of compounds 9 (scheme 3) into compounds I-B can be performed in perfect analogy to that of compounds 3 (scheme 1) into compounds I. Compounds I-B (scheme 3) which contain an ester function in the ether substituent $R^{13}O$, can be used as such or can optionally be saponified, e.g., using lithium hydroxide in a solvent like tetrahydrofuran/water to give compounds I-C carrying an acid function in the ether substituent $R^{14}O$.

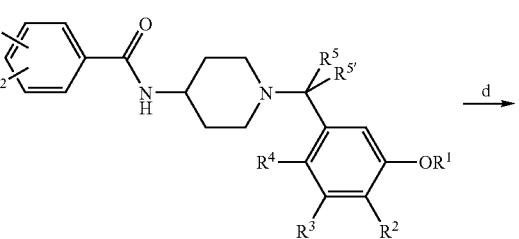

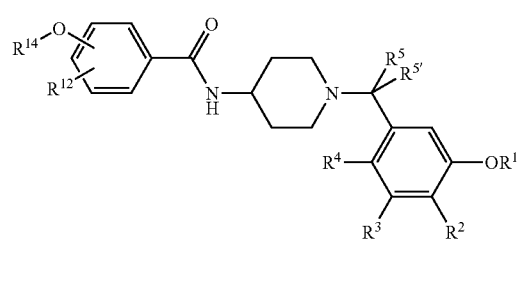

The requisite aldehyde partners III are either commercially available or can be obtained by alkylation (scheme 4, step a) of the phenolic aldehydes 11 with alkyl halides, alkyl mesylates or alkyl tosylates in a polar solvent, e.g., DMF, and a suitable base, e.g., $Cs_2CO_3$, $K_2CO_3$, at room or elevated temperature, or by Mitsonobu reaction with alcohols activated by a mixture of triphenylphosphine and diethyl- or di-tert-butyl-azodicarboxylate, or by analogous alkylation (step b) of the phenolic carboxylic esters (or acids) 12. In the latter case, reduction of the esters 13 by a suitable reducing agent, e.g., diisobutylaluminum hydride or $LiAlH_4$ at temperatures between −78° C. and ambient temperature in a solvent like THF will provide the alcohols 14 (step c). These can then be oxidized to the aldehydes III, preferably with $MnO_2$ as oxidant in DCM (step d).

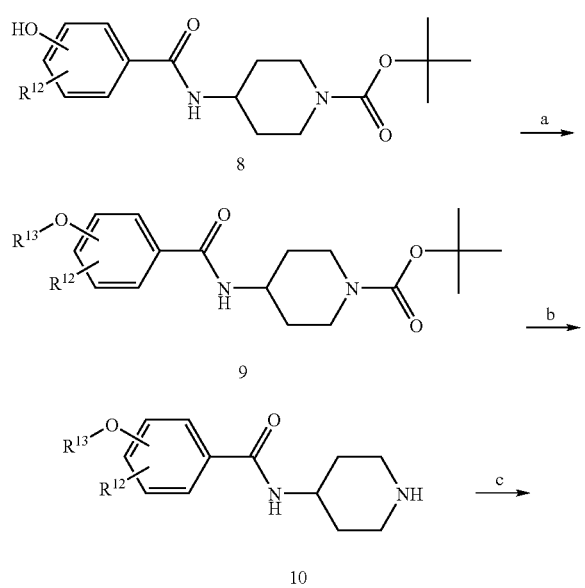

Scheme 4

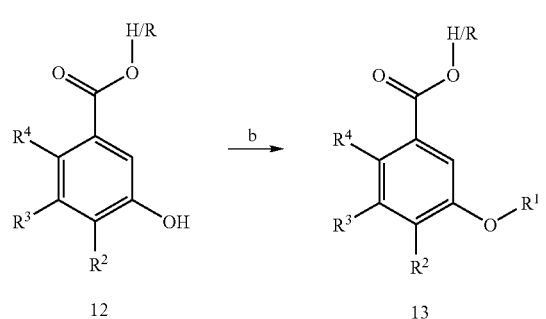

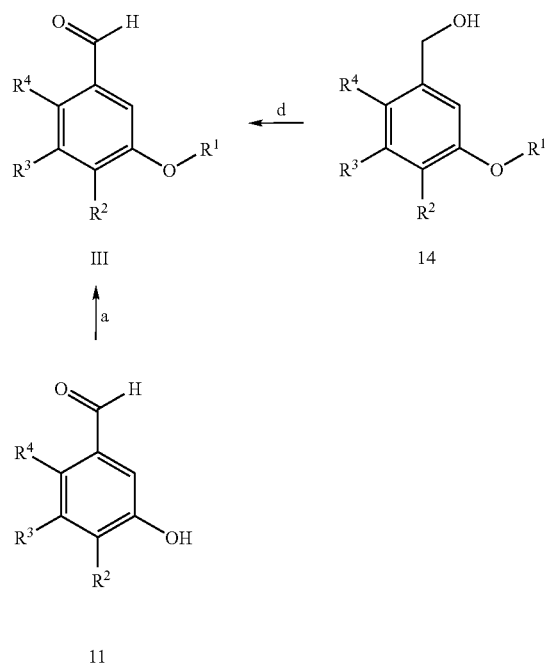

4-Halogen substituted acids 15 are known or can be prepared by methods well known in the art. Double alkylation, reduction and ensuing oxidation as described in scheme 4 provides 4-halogen substituted aldehydes 18 (scheme 5, steps a, b and c).

Scheme 5

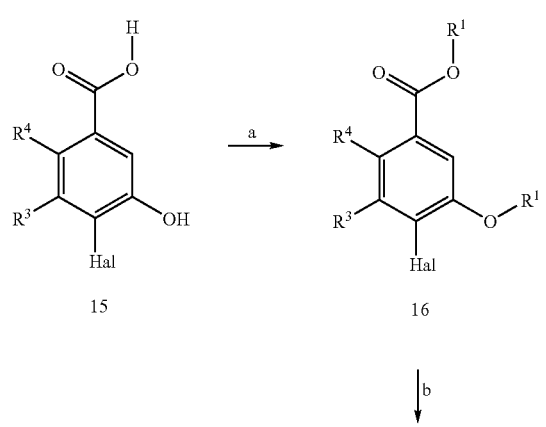

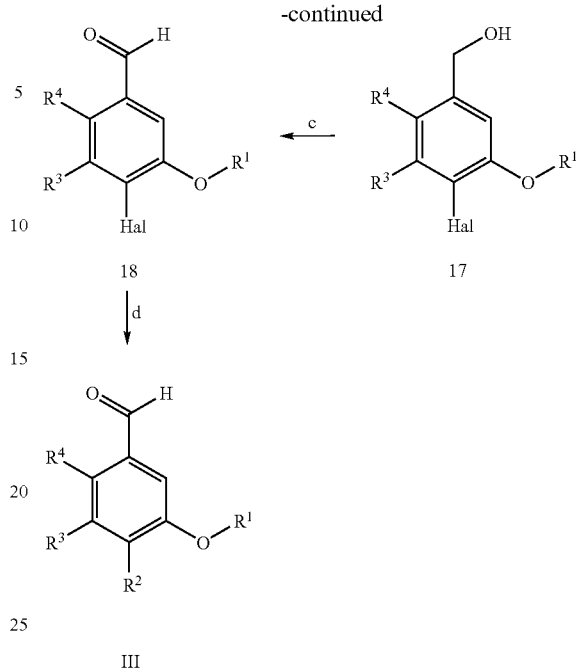

4-Fluoro aldehydes 18 (Hal=F) react with imidazole or triazole in solvents like dimethylsulfoxide (DMSO) or dimethylformamide (DMF) in the presence of a base like potassium or sodium carbonate at elevated temperatures to provide aldehydes III with $R^2$ representing a nitrogen linked imidazole or triazole moiety. 4-Iodo aldehydes 18 (Hal=I) react with cycloalkyl or aryl boronic acids in the presence of catalysts like $(Ph_3P)_4Pd$ or $Pd(OAc)_2$/tricyclohexylphosphine and a base like $K_3PO_4$ in solvents or solvent mixtures including toluene, water, tetrahydrofuran, 1,2-dimethoxyethane or DMF to give aldehydes III with $R^2$ representing aryl or cycloalkyl (step d).

Additional synthetic procedures are described in more detail in the experimental part.

The following tests were carried out in order to determine the activity of the compounds of formula (I).

A CHO cell line stably transfected with a plasmid encoding the human subtype 5 somatostatin receptor (GenBank accession number D16827) was obtained from Euroscreen. Cells were cultured and used for binding and functional assays.

Membranes of these cells were prepared by sonication in the presence of protease inhibitors and subsequent fractionating centrifugation. The protein concentration in the membrane preparation was determined using a commercial kit (BCA kit, Pierce, USA). Membranes were stored at −80° C. until use. After thawing, membranes were diluted in assay buffer (50 mM TRIS-HCl at pH 7.4, 5 mM $MgCl_2$ and 0.20% BSA (bovine serum albumine)) and subjected to dounce homogenization.

For binding studies, 0.1 ml membrane suspension, corresponding to app. $6 \times 10^{-15}$ mol receptor, was incubated for 1 hour at room temperature with 0.05 nM $^{125}$-I-labeled tracer (11-Tyr somatostatin-14, Perkin-Elmer) and either test compounds in varying concentrations or, for the determination of non-specific binding, 0.001 mM non-labeled somatostatin-14 (Sigma-Aldrich, Buchs, Switzerland). The incubation was stopped by filtration through GF/B glassfiber filters (Unifilter, Perkin-Elmer) and washing with ice-cold wash buffer (50 mM Tris-HCl at pH 7.4). The bound radioactivity was measured after application of a scintillation cocktail (Microscint 40, Perkin-Elmer) and expressed as disintegrations per minute (dpm).

The receptor concentration was determined in a prior saturation experiment where a fixed, arbitrary amount of membranes was incubated with a concentration range of radiolabeled tracer. This allows estimating the total number of specific binding sites per amount of protein (i.e. $B_{max}$), typically between 1 and 5 pmol/mg.

The concentration of the test compound required to result in half maximal inhibition of binding of the radio-labeled tracer ($IC_{50}$) was estimated from a concentration-versus-dpm graph. The binding affinity ($K_i$) was calculated from the $IC_{50}$ by applying the Cheng-Prussoff equation for single binding sites.

For functional experiments, 50'000 cells were incubated in Krebs Ringer HEPES buffer (115 mM NaCl, 4.7 mM KCl, 2.56 mM $CaCl_2$, 1.2 mM $KH_2PO_4$, 1.2 mM $MgSO_4$, 20 mM $NaHCO_3$ and 16 mM HEPES, adjusted to pH 7.4) supplemented with 1 mM IBMX (3-isobutyl-1-methyl-xanthin) and 0.1% BSA, then stimulated with 0.004 mM forskolin. Simultaneously with forskolin, test compounds in varying concentrations were applied. Cells were then incubated for 20 minutes at 37° C. and 5% $CO_2$. Subsequently, cells were lysed and cAMP (cyclic adenosine monophosphate) concentration measured using a fluorescence-based commercial kit according to the manufacturer (HitHunter cAMP, DiscoverX).

The concentration of the test compound to induce a half maximal effect (i.e. $EC_{50}$) as well as the efficacy as compared to 0.15 nM somatostatin-14 were determined from concentration-versus-fluorescence (arbitrary units) graphs. For the determination of potential antagonism, 0.15 nM somatostatin-14 was applied together with the test compounds and the concentration of the test compounds to half maximally reverse the effect of somatostatin-14 (i.e. $IC_{50}$) were deduced from concentration-versus-fluorescence graphs.

The compounds of the present invention exhibit $K_i$ values of 0.1 nM to 10 µM, preferably $K_i$ values of 1 nM to 500 nM and more preferably 0.1 nM to 100 nM for human subtype 5 somatostatin receptor. The following table shows measured values for selected compounds of the present invention that are antagonists as assessed in functional experiments.

| | SSTR5 $K_i$ (nM) |
|---|---|
| Example 6 | 126 |
| Example 30 | 38 |
| Example 35 | 19 |

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable salts, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula (I).

The present invention will be further explained by reference to the following illustrative examples. They are, however, not intended to limit its scope in any manner.

EXAMPLES

Abbreviations

Ar=Argon, Boc=tert-butyloxycarbonyl, CDI=1,2-carbonyldiimidazole, CI=chemical ionization, DCE=dichloroethane, DEAD=diazenedicarboxylic acid diethyl ester, DCM=dichloromethane, DME=dimethyl ether, DMF=dimethylformamide, DMSO=dimethylsulfoxide, EDCI=N-(3-dimethylaminopropyl)-N'-ethylcarbodiimide hydrochloride, EtOAc=ethyl acetate, EI=electron impact (ionization), Hyflo=infusorial earth, Kieselguhr (filter aid), ISP=ion spray positive (mode), ISN=ion spray negative (mode), MS=electrospray mass spectrum, NMR=nuclear magnetic resonance, P=protecting group, py=pyridine, THF=tetrahydrofuran, TFA=trifluoroacetic acid.

Example 1

N-[1-(4-Chloro-3-ethoxy-benzyl)piperidin-4-yl]-6-imidazol-1-yl-nicotinamide 4-Chloro-3-ethoxy-benzaldehyde The title compound was prepared from commercially available 4-chloro-3-hydroxy-benzoic acid as follows: 4-chloro-3-hydroxy-benzoic acid (3.0 g, 17 mmol) was dissolved in DMF (15 ml) and $K_2CO_3$ (4.7 g, 34.0 mmol) and EtI (6.0 g, 38 mmol) were added and the reaction stirred for 6 h.

The reaction was then diluted with water and extracted with EtOAc. The organic extracts were dried (Na$_2$SO$_4$) and concentrated to afford 3.6 g (91% yield) of 4-chloro-3-ethoxybenzoic acid ethyl ester. The crude ester was then dissolved in THF (20 mL) and cooled to −78° C. under Ar. Di-isobutylaluminium hydride (95 mL, 1M in THF, 95 mmol) was then slowly added (15 min), the cooling bath removed on completion of addition and the reaction allowed to reach 0° C. (1 h). The reaction was then cooled to −78° C., the excess hydride was quenched by cautious addition of 1N HCl. The mixture was brought to room temperature, the organic separated and the aqueous extracted with EtOAc. The combined organic were dried (Na$_2$SO$_4$) and concentrated to afford 2.9 g (100% yield) of 4-chloro-3-ethoxy-benzyl alcohol. 2.94 g (16 mmol) of the crude alcohol was dissolved in DCM (15 mL) and MnO$_2$ (5.5 g, 63 mmol) was added. The reaction was stirred for 16 h, after which time the reaction was filtered through Hyflo and concentrated. The residue was purified by flash column chromatography (EtOAc:Heptane 1:4) to yield 1.5 g (52% yield) of the title aldehyde.

$^1$H NMR (300 MHz, CDCl$_3$): δ1.51 (t, J=7.1 Hz, 3H), 4.19 (q, J=7.1 Hz, 2H), 7.37-7.42 (m, 2H), 7.55 (d, J=9.0 Hz, 1H), 9.94 (s, 1H).

1-(4-Chloro-3-ethoxy-benzyl)piperidin-4-ylamine

4-Chloro-3-ethoxy-benzaldehyde (1.4 g, 7 mmol) was mixed with boc-4-amino-piperidine (1.3 g, 7 mml) and acetic acid (0.4 ml, 7 mmol) in DCM (15 mL), and sodium triacetoxyborohydride (1.8 g, 8 mmol) was added. The reaction was stirred for 16 h after which time the reaction was diluted with DCM, washed with saturated NaHCO$_3$, dried (Na$_2$SO$_4$) and concentrated affording [1-(4-chloro-3-ethoxy-benzyl)piperidin-4-yl]-carbamic acid tert-butyl ester (2.5 g, 96%) which was used directly in the next step. The crude product was dissolved in TFA (25 ml) and stirred for 0.5 h after which time the TFA was removed under vacuum, the residue redissolved in DCM, washed with saturated NaHCO$_3$, dried (Na$_2$SO$_4$) and concentrated. This afforded the title product (1.8 g, quant.) as a yellow solid.

$^1$H NMR (300 MHz, CDCl$_3$): δ1.37-0.49 (m, 5H), 1.77-1.81(m, 2H), 2.02 (td, J=11.4, 2.2 Hz, 2H), 2.62-2.77 (m, 1H), 2.79-2.95 (m, 2H), 3.44 (s, 2H), 4.10 (q, J=6.9 Hz, 2H), 6.78-6.82 (m, 2H), 6.95 (d, J=9.0 Hz, 1H), 7.26 (d, J=8.1 Hz, 2H).

N-[1-(4-Chloro-3-ethoxy-benzyl)piperidin-4-yl]-6-imidazol-1-yl-nicotinamide 6-(1-Imidazoyl)nicotinic acid (21 mg, 0.11 mmol) and CDI (19 mg, 0.12 mmol) were dissolved in DMF (0.5 ml) and shaken for 1 h. Then 1-(4-chloro-3-ethoxy-benzyl)piperidin-4-ylamine (27 mg, 0.1 mmol) was added as a solution in DMF (0.5 ml) was added and the reaction stirred for 16 h, after which time the solvent was evaporated and the residue purified by reversed phase HPLC (MeCN:H$_2$O) affording the title compound (18 mg, 41%). MS: 440.4 (MH$^+$)

Example 2

N-[1-(4-Chloro-3-ethoxy-benzyl)piperidin-4-yl]-2-morpholin-4-yl-isonicotinamide

The title compound (16 mg, 34%) was prepared analogously to example 1 by coupling of 1-(4-chloro-3-ethoxy-benzyl)piperidin-4-ylamine with 2-(4-morpholinyl)-4-pyridinecarboxylic acid. MS: 459.4 (MH$^+$)

Example 3

1H-indole-4-carboxylic acid[1-(4-chloro-3-ethoxy-benzyl)piperidin-4-yl]-amide

The title compound (13 mg, 32%) was prepared analogously to example 1 by coupling of 1-(4-chloro-3-ethoxy-benzyl)piperidin-4-ylamine with indole-4-carboxylic acid. MS: 412.4 (MH$^+$)

Example 4

N-[1-(4-Chloro-3-ethoxy-benzyl)piperidin-4-yl]-3-methanesulfonylbenzamide

The title compound (22 mg, 49%) was prepared analogously to example 1 by coupling of 1-(4-chloro-3-ethoxy-benzyl)piperidin-4-ylamine with 3-methylsulfonyl benzoic acid. MS: 451.4 (MH$^+$)

Example 5

N-[1-(4-Chloro-3-ethoxy-benzyl)piperidin-4-yl]-6-dimethylamino-nicotinamide

The title compound (11 mg, 26%) was prepared analogously to example 1 by coupling of 1-(4-chloro-3-ethoxy-benzyl)piperidin-4-ylamine with 6-dimethylamino nicotinic acid (*J. Org. Chem.* 1999, 9, 2293). MS: 417.4 (MH$^+$)

Example 6

N-[1-(4-Chloro-3-ethoxy-benzyl)piperidin-4-yl]-isophthalimide

The title compound (20 mg, 48%) was prepared analogously to example 1 by coupling of 1-(4-chloro-3-ethoxy-benzyl)piperidin-4-ylamine with isophthalamic acid (*Chem. Ber.* 1910, 43, 3474). MS: 416.4 (MH$^+$)

Example 7

N-[1-(4-Chloro-3-ethoxy-benzyl)piperidin-4-yl]-benzamide

Benzoyl chloride (17 mg, 0.11 mmol), Et$_3$N (20 μL, 0.15 mmol) and 1-(4-chloro-3-ethoxy-benzyl)piperidin-4-ylamine (27 mg, 0.1 mmol) were shaken in DMF (0.5 ml) for 16 h, after which time the solvent was evaporated and the residue purified by reversed phase HPLC (MeCN:H$_2$O) affording the title compound (22 mg, 60%). MS: 373.4 (MH$^+$)

Example 8

1H-indole-7-carboxylic acid[1-(4-chloro-3-ethoxy-benzyl)piperidin-4-yl]-amide

Indole-7-carboxlic acid (19 mg, 0.12 mmol), Et$_3$N (20 μL, 0.15 mmol), EDCI (25 mg, 0.13 mmol) and 1-(4-chloro-3-ethoxy-benzyl)piperidin-4-ylamine (27 mg, 0.1 mmol) were shaken in DMF (1.0 ml) for 16 h, after which time the solvent was evaporated and the residue purified by reversed phase HPLC (MeCN:H$_2$O) affording the title compound (12 mg, 29%). MS: 412.4 (MH$^+$)

Example 9

N-[1-(4-Chloro-3-ethoxy-benzyl)piperidin-4-yl]-4-isopropyl-benzamide

The title compound (7 mg, 17%) was prepared analogously to example 8 by coupling of 1-(4-chloro-3-ethoxy-benzyl)piperidin-4-ylamine with 4-isopropylbenzoic acid. MS: 415.5 (MH$^+$)

Example 10

4-tert-Butyl-N-[1-(4-chloro-3-ethoxy-benzyl)piperidin-4-yl]-benzamide

The title compound (13 mg, 30%) was prepared analogously to example 8 by coupling of 1-(4-chloro-3-ethoxy-benzyl)piperidin-4-ylamine with 4-tert-butylbenzoic acid. MS: 429.5 (MH$^+$)

Example 11

N-[1-(4-Chloro-3-ethoxy-benzyl)piperidin-4-yl]-4-ethyl-benzamide

The title compound (25 mg, 63%) was prepared analogously to example 8 by coupling of 1-(4-chloro-3-ethoxy-benzyl)piperidin-4-ylamine with 4-ethyllbenzoic acid. MS: 401.4 (MH$^+$)

Example 12

N-[1-(4-Chloro-3-ethoxy-benzyl)piperidin-4-yl]-3-methyl-benzamide

The title compound (22 mg, 56%) was prepared analogously to example 7 by coupling of 1-(4-chloro-3-ethoxy-benzyl)piperidin-4-ylamine with 3-methylbenzoyl chloride. MS:387.4 (MH$^+$)

Example 13

N-[1-(4-Chloro-3-ethoxy-benzyl)piperidin-4-yl]-5-methoxy-nicotinamide

The title compound (9 mg, 23%) was prepared analogously to example 8 by coupling of 1-(4-chloro-3-ethoxy-benzyl)piperidin-4-ylamine with 3-methoxynicotinic acid (*J. Med. Chem.* 2000, 43 (16), 3168). MS: 404.4 (MH$^+$).

Example 14

N-[1-(4-Chloro-3-ethoxy-benzyl)piperidin-4-yl]-4-methyl-benzamide

The title compound (22 mg, 56%) was prepared analogously to example 7 by coupling of 1-(4-chloro-3-ethoxy-benzyl)piperidin-4-ylamine with 4-methylbenzoyl chloride. MS: 387.4 (MH$^+$).

Example 15

N-[1-(4-Chloro-3-ethoxy-benzyl)piperidin-4-yl]-4-chloro-benzamide

The title compound (27 mg, 66%) was prepared analogously to example 7 by coupling of 1-(4-chloro-3-ethoxy-benzyl)piperidin-4-ylamine with 4-chlorobenzoyl chloride. MS: 407.4 (MH$^+$).

Example 16

N-[1-(4-Chloro-3-ethoxy-benzyl)piperidin-4-yl]-3-methoxy-benzamide

The title compound (26 mg, 65%) was prepared analogously to example 7 by coupling of 1-(4-chloro-3-ethoxy-benzyl)piperidin-4-ylamine with 3-methoxybenzoyl chloride. MS: 403.4 (MH$^+$).

Example 17

N-[1-(4-Chloro-3-ethoxy-benzyl)piperidin-4-yl]-2-methyl-benzamide

The title compound (24 mg, 63%) was prepared analogously to example 7 by coupling of 1-(4-chloro-3-ethoxy-benzyl)piperidin-4-ylamine with 2-methylbenzoyl chloride. MS:387.4 (MH$^+$).

Example 18

N-[1-(4-Chloro-3-ethoxy-benzyl)piperidin-4-yl]-2,5-dimethyl-benzamide

The title compound (4 mg, 10%) was prepared analogously to example 8 by coupling of 1-(4-chloro-3-ethoxy-benzyl)piperidin-4-ylamine with 2,5-dimethylbenzoic acid. MS: 401.4 (MH$^+$).

Example 19

N-[1-(4-Chloro-3-ethoxy-benzyl)piperidin-4-yl]-4-methoxy-benzamide

The title compound (24 mg, 60%) was prepared analogously to example 7 by coupling of 1-(4-chloro-3-ethoxy-benzyl)piperidin-4-ylamine with 4-methoxybenzoyl chloride. MS: 403.4(MH$^+$).

Example 20

N-[1-(4-Chloro-3-ethoxy-benzyl)piperidin-4-yl]-2,4-dimethyl-benzamide

The title compound (3 mg, 8%) was prepared analogously to example 8 by coupling of 1-(4-chloro-3-ethoxy-benzyl)piperidin-4-ylamine with 2,4-dimethylbenzoic acid. MS: 401.4 (MH$^+$).

Example 21

Napthalene-1-carboxylic acid[1-(4-chloro-3-ethoxy-benzyl)piperidin-4-yl]-amide The title compound (26 mg, 62%) was prepared analogously to example 7 by coupling of 1-(4-chloro-3-ethoxy-benzyl)piperidin-4-ylamine with 1-napthoyl chloride. MS: 423.4 (MH$^+$).

Example 22

N-[1-(4-Chloro-3-ethoxy-benzyl)piperidin-4-yl]-3-dimethylamino-benzamide

The title compound (14 mg, 33%) was prepared analogously to example 8 by coupling of 1-(4-chloro-3-ethoxy-benzyl)piperidin-4-ylamine with 3-dimethylaminobenzoic acid. MS: 416.4 (MH$^+$).

Example 23

N-[1-(4-Chloro-3-ethoxy-benzyl)piperidin-4-yl]-6-methyl-nicotinamide

The title compound (3 mg, 8%) was prepared analogously to example 8 by coupling of 1-(4-chloro-3-ethoxy-benzyl)piperidin-4-ylamine with 6-methylnicotinic acid. MS: 388.4 (MH$^+$).

Example 24

N-[1-(4-Chloro-3-ethoxy-benzyl)piperidin-4-yl]-3,5-dimethoxy-benzamide

The title compound (24 mg, 56%) was prepared analogously to example 7 by coupling of 1-(4-chloro-3-ethoxy-benzyl)piperidin-4-ylamine with 3,5-dimethoxybenzoyl chloride. MS: 433.5 (MH$^+$).

Example 25

N-[1-(4-Chloro-3-ethoxy-benzyl)piperidin-4-yl]-3-methoxy-4-methyl-benzamide

The title compound (29 mg, 69%) was prepared analogously to example 8 by coupling of 1-(4-chloro-3-ethoxy-benzyl)piperidin-4-ylamine with 3-methoxy-4-methylbenzoic acid. MS: 417.4 (MH$^+$).

Example 26

Benzo[1,3]dioxole-5-carboxylic acid[1-(4-chloro-3-ethoxy-benzyl)piperidin-4-yl]-amide The title compound (24 mg, 56%) was prepared analogously to example 7 by coupling of 1-(4-chloro-3-ethoxy-benzyl)piperidin-4-ylamine with 3,4-dioxymethylene benzoyl chloride. MS: 417.4 (MH$^+$).

Example 27

N-[1-(4-Chloro-3-ethoxy-benzyl)piperidin-4-yl]-2,3-dimethoxy-benzamide

The title compound (6 mg, 14%) was prepared analogously to example 8 by coupling of 1-(4-chloro-3-ethoxy-benzyl)piperidin-4-ylamine with 2,3-dimethoxy-benzoic acid. MS: 433.5 (MH$^+$).

Example 28

6-Amino-N-[1-(4-chloro-3-ethoxy-benzyl)piperidin-4-yl]-nicotinamide 1-(4-Chloro-3-ethoxy-benzyl)piperidin-4-ylamine (0.33 g, 1.0 mmol), 6-amino-nicotinic acid (0.17 g, 1.0 mmol) and EDCI (0.28 g, 1.2 mmol) were mixed with DMF (5 ml) and heated to 60° C. for 24 h, after which time the reaction was allowed to cool, poured into dilute NaHCO$_3$ and extracted with EtOAc. The combined organic was dried (Na$_2$SO$_4$) and concentrated. The residue was purified by flash column chromatography (DCM:MeOH 9:1-4:1) affording the title product (0.12 g, 24%).

$^1$H NMR (300 MHz, MeOD): δ1.43 (t, J=6.9 Hz, 3H), 1.58-1.65 (m, 2H), 1.84-1.93 (m, 2H), 2.11-2.20 (m, 2H), 2.88-2.94 (m, 2H), 3.51 (s, 2H), 3.81-4.89 (m, 1H), 4.13 (q, J=6.9 Hz, 2H), 6.55 (d, J=8.7 Hz, 1H), 6.85-6.89 (m, 1H), 7.06 (s, 1H), 7.28 (d, J=7.8 Hz, 1H), 7.84-7.88 (m, 1H), 8.35 (s, 1H), 8.41 (s, 1H).

Example 29

5-Amino-N-[1-(4-chloro-3-ethoxy-benzyl)piperidin-4-yl]-nicotinamide

The title compound (0.18 g, 37%) was prepared analogously to example 28 from 1-(4-chloro-3-ethoxy-benzyl)piperidin-4-ylamine and 5-aminonicotinic acid.

$^1$H NMR (300 MHz, DMSO): δ1.29 (t, J=7.0 Hz, 3H), 1.42-1.49 (m, 2H), 1.62-1.67 (m, 2H), 1.91-1.99 (m, 2H), 2.71-2.76 (m, 2H), 3.25 (m, 2H), 3.60-3.77 (m, 1H), 4.04 (q, J=7.0 Hz, 2H), 6.80 (d, J=8.1 Hz, 1H), 6.98 (s, 1H), 7.19 (s, 1H), 7.27 (d, J=7.8 Hz, 1H), 7.94 (s, 1H), 8.07 (s, 1H), 8.15 (d, J=7.8 Hz, 1H).

Example 30

N-[1-(4-Chloro-3-ethoxy-benzyl)piperidin-4-yl]-5-methyl-nicotinamide N-(1-Benzyl-piperidin-4-yl)-5-methyl-nicotinamide 4-Amino-1-benylpiperidine (2.0 g, 11 mmol), 5-methyl-nicotinic acid (1.7 g, 13 mmol) and EDCI (2.6 g, 14 mmol) were dissolved in DMF (30 mL) and stirred for 16 h. The DMF was evaporated and the residue dissolved in DCM, washed with H$_2$O, dried (Na$_2$SO$_4$) and concentrated. The title product (1.3 g, 40%) was isolated by crystallization of the residue from EtOAc.

$^1$H NMR (300 MHz, CDCl$_3$): δ1.47-1.63 (m, 2H), 2.0-2.04 (m, 2H), 2.15-2.23 (m, 2H), 2.39 (s, 3H), 2.84-2.88 (m, 2H), 3.53 (s, 2H), 4.0-4.05 (m, 1H), 6.01 (d, I=7.5 Hz, 1H), 7.23-7.33 (m, 5H), 7.90 (s, 1H), 8.54 (s, 1H), 8.72 (s, 1H).

5-Methyl-N-(piperidin-4-yl)-nicotinamide

N-(1-Benzyl-piperidin-4-yl)-5-methyl-nicotinamide (1.3 g, 4 mmol), Pd(OH)$_2$/C (0.1 g) and cyclohexene (2 ml) were heated at reflux in EtOH (15 mL) for 2 h, after which time the reaction was filtered hot through a pad of Hyflo. The filtrate was concentrated to afford the title compound as a white powder (0.9 g, 98%).

$^1$H NMR (300 MHz, DMSO): δ1.33-1.46 (m, 2H), 1.71-1.75 (m, 2H), 2.35 (s, 3H), 2.49-2.53 (m, 2H) 2.93-2.96 (m, 2H), 3.75-3.87 (m, 1H), 7.99 (s, 1H), 8.37 (d, J=9.0 Hz, 1H), 8.52 (s, 1H), 8.78 (s, 1H).

N-[1-(4-Chloro-3-ethoxy-benzyl)piperidin-4-yl]-5-methyl-nicotinamide

To a solution of 5-methyl-N-(piperidin-4-yl)-nicotinamide (22 mg, 0.10 mmol), 4-chloro-3-ethoxy-benzaldehyde (22 mg, 0.12 mmol) in DCE:EtOH (1:11 mL) was added acetic acid (25 µL) and pyridine-borane complex (25 µL, 8M in pyridine, 0.2 mmol). The reaction was shaken for 16 h, after which time it was concentrated and purified by reversed phase HPLC (MeCN:H$_2$O) affording the title compound (22 mg, 57%). MS: 388.4 (MH$^+$)

Example 31

N-[1-(3,5-Diethoxy-benzyl)piperidin-4-yl]-5-methyl-nicotinamide 3,5-Diethoxy-benzaldehyde [CA 120355-79-5]

The title compound was prepared analogously to example 1 by reaction of 3,5-dihydroxybenzaldehyde with ethyliodide in DMF using K$_2$CO$_3$ as base.

N-[1-(3,5-Diethoxy-benzyl)piperidin-4-yl]-5-methyl-nicotinamide

The title compound (13 mg, 33%) was prepared analogously to example 30 from 5-methyl-N-(piperidin-4-yl)-nicotinamide and 3,5-diethoxybenzaldehyde. MS: 398.5 (MH$^+$).

Example 32

N-[1-(4-Amino-3,5-diethoxy-benzyl)piperidin-4-yl]-5-methyl-nicotinamide (4-Amino-3,5-diethoxy-phenyl)-methanol To a solution of 4-amino-3,5-diethoxy-benzoic acid ethyl ester (2.8 g, 11.05 mmol, prepared as described in *Helv. Chim. Acta* 1977, 60, 3025-3034) in dichloromethane (50 mL) at 0° C. under Ar was slowly added diisobutylaluminium hydride (27.6 mL, 27.64 mmol, 1 M solution in dichloromethane) over a time periode of 15 min, the cooling bath removed on completion of addition. After 18 h, the excess hydride was quenched by cautious addition of a sat. solution of potassium sodium tartrate (10 mL). The solidified mixture was extracted with dichloromethane (5×200 mL) and THF (2×150 mL), the combined organic phases washed with water (3×100 mL), dried over $MgSO_4$, concentrated by evaporation under reduced pressure and the crude material purified with column chromatography on silica eluting with a gradient of heptane/ethyl acetate (4:1→1:1) providing 1.10 g (47%) of the title compound.
$^1$H NMR (300 MHz, $CDCl_3$): δ1.42 (t, J=7.0 Hz, 3H), 3.82 (br s, 2H), 4.05 (q, J=7.0 Hz, 2H), 4.54 (s, 2H), 6.50 (s, 2H).

4-Amino-3,5-diethoxybenzaldehyde

To a solution of (4-amino-3,5-diethoxy-phenyl)-methanol (0.79 g, 3.74 mmol) in DMF (20 mL) was added $MnO_2$ (1.63 g, 18.70 mmol). The reaction mixture was stirred for 24 h at rt, filtered through Hyflo, the filtrate extracted with ethyl acetate (3×50 mL) and the combined organic phases dried over $MgSO_4$ providing 0.69 g (88%) of the title compound.
$^1$H NMR (300 MHz, DMSO): δ1.46 (t, J=7.0 Hz, 3H), 4.15 (q, J=7.0 Hz, 2H), 4.50 (br s, 2H), 7.04 (s, 2H), 9.70 (s, 1H).

N-[1-(4-Amino-3,5-diethoxy-benzyl)piperidin-4-yl]-5-methyl-nicotinamide

The title compound (14 mg, 34%) was prepared analogously to example 30 from 5-methyl-N-(piperidin-4-yl)-nicotinamide and 4-amino-3,5-diethoxybenzaldehyde. MS: 413.5 ($MH^+$)

Example 33

N-{1-[3-Ethoxy-5-(tetrahdro-pyran-4-yl-oxy)-benzyl]piperidin-4-yl}-5-methyl-nicotinamide 3-Ethoxy-5-(tetrahydro-pyran-4-yloxy)-benzaldehyde To a mixture of triphenylphosphine (1.18 g, 4.49 mmol) and DEAD (0.76 mL, 0.85 g, 4.89 mmol) in anhydrous THF (10 mL) was added 3-ethoxy-5-hydroxy-benzoic acid methyl ester (0.80 g, 4.08 mmol, prepared as described in WO 9905123 A1) and tetrahydro-pyran-4-ol (0.42 g, 4.08 mmol), dissolved in THF (10 mL), at 0° C. under Ar. After stirring for 6 h, the solvent was partially removed by evaporation under reduced pressure, water (50 mL) added and the reaction mixture extracted with ethyl acetate (3×50 mL). The combined organic phases were dried over $MgSO_4$, the solvent removed by evaporation under reduced pressure and the crude material ielding 0.64 g (56%) of 3-ethoxy-5-(tetrahydro-pyran-4-yloxy)-benzoic acid methyl ester which was directly used in the next step. To a solution of 3-ethoxy-5-(tetrahydro-pyran-4-yloxy)-benzoic acid methyl ester (0.64 g, 2.28 mmol) in anhydrous THF (20 mL) was added lithium aluminium hydride (0.217 g, 5.71 mmol) and the reaction mixture stirred at rt for 4 h. The crude reaction mixture was filtered over Hyflo, the filtrate extracted with diethyl ether (3×50 mL) and the combined organic phases dried over $MgSO_4$ providing 0.56 g (100%) of the benzyl alcohol. The crude reaction product (0.56 g, 2.22 mmol) was dissolved in THF (20 mL) and $MnO_2$ (1.93 g, 22.2 mmol) was added. After stirring at rt for 3 h, the reaction mixture was filtered over Hyflo and the solvent removed by evaporation under reduced pressure. A conc. solution of sodium chloride (100 mL) was added, the mixture extracted with ethyl acetate (3×100 mL) and the combined organic phases dried over $MgSO_4$ providing 0.46 g (83%) of the title compound.
$^1$H NMR (300 MHz, $CDCl_3$): δ1.34 (t, J=7.0 Hz, 3H), 1.66-1.76 (m, 2H), 1.91-1.98 (m, 2H), 3.46-3.53 (m, 2H), 3.85-3.92 (m, 2H), 3.98 (q, J=7.0 Hz, 2H), 4.41-4.47 (m, 1H), 6.62-6.63 (m, 1H), 6.89-6.91 (m, 2H), 9.79 (s, 1H).

N-{1-[3-Ethoxy-5-(tetrahdro-pyran-4-yl-oxy)-benzyl]piperidin-4-yl}-5-methyl-nicotinamide The title compound (16 mg, 34%) was prepared analogously to example 30 from 5-methyl-N-(piperidin-4-yl)-nicotinamide and 3-ethoxy-5-(tetrahydro-pyran-4-yl-oxy)-benzaldehyde. MS: 454.6 ($MH^+$)

Example 34

N-[1-(3-Ethoxy-4-methyl-benzyl)piperidin-4-yl]-5-methyl-nicotinamide Ethoxy-4-methyl-benzaldehyde [CA 157143-20-9]

The title compound was prepared in analogy to example 31 by reaction of commercially available 3,5-dihydroxybenzaldehyde with ethyliodide in DMF using $K_2CO_3$ as base.

N-[1-(3-Ethoxy-4-methyl-benzyl)piperidin-4-yl]-5-methyl-nicotinamide

The title compound (13 mg, 35%) was prepared analogously to example 30 from 5-methyl-N-(piperidin-4-yl)-nicotinamide and 3-ethoxy-4-methyl-benzaldehyde. MS: 368.5 ($MH^+$).

Example 35

N-[1-(3,5-Diethoxy-4-ethoxycarbonyl-benzyl)piperidin-4-yl]-5-methyl-nicotinamide 3,5-Diethoxy-4-ethoxycarbonyl-benzaldehyde The title compound was prepared as described in DE 2435934.

N-[1-(3,5-Diethoxy-4-ethoxycarbonyl-benzyl)piperidin-4-yl]-5-methyl-nicotinamide The title (15 mg, 32%) compound was prepared analogously to example 30 from 5-methyl-N-(piperidin-4-yl)-nicotinamide and 3,5-diethoxy-4-ethoxycarbonyl-benzaldehyde. MS: 470.5 ($MH^+$)

Example 36

N-[1-(3-Ethoxy-4-fluoro-benzyl)piperidin-4-yl]-5-methyl-nicotinamide 3-Ethoxy-4-fluoro-benzaldehyde The title compound was prepared as in example 1 starting from 4-fluoro-3-hydroxy-benzoic acid in 73% overall yield after final purification by flash column chromatography on silica eluting with hexane/ethyl acetate (10:1).

¹H NMR (300 MHz, DMSO): δ1.32 (t J=7.0 Hz, 3H), 4.12 (q, J=7.0 Hz, 2H), 7.34-7.41 (m, 1H), 7.47-7.56 (m, 2H), 9.87 (s, 1H).

N-[1-(3-Ethoxy-4-fluoro-benzyl)piperidin-4-yl]-5-methyl-nicotinamide

The title compound (11 mg, 30%) was prepared analogously to example 30 from 5-methyl-N-(piperidin-4-yl)-nicotinamide and 3-ethoxy-4-fluoro-benzaldehyde. MS: 372.5 (MH⁺)

Example 37

N-[1-[3-Ethoxy-4-(1-ethyl-propoxy)-benzyl]piperidin-4-yl]-5-methyl-nicotinamide 3-Ethoxy-4-(1-ethyl-propoxy)-benzaldehyde The title compound was prepared analogously to example 31 by reaction of 3-ethoxy-4-hydroxy-benzaldehyde with 3-bromo-pentane in DMF using $K_2CO_3$ as base. MS: 237.1 (MH⁺).

N-[1-[3-Ethoxy-4-(1-ethyl-propoxy)-benzyl]piperidin-4-yl]-5-methyl-nicotinamide The title compound (14 mg, 36%) was prepared analogously to example 30 from 5-methyl-N-(piperidin-4-yl)-nicotinamide and 3-ethoxy-4-(1-ethyl-propoxy)-benzaldehyde. MS: 440.6 (MH⁺)

Example 38

N-[1-(5-Amino-3-ethoxy-4-iodo-benzyl)piperidin-4-yl]-5-methyl-nicotinamide 3-Amino-5-hydroxy-4-iodo-benzoic acid To a solution of 3-amino-5-hydroxy-benzoic acid (0.33 g, 2.16 mmol, [CA 76045-71-1]) in methanol (18 mL) at 0° C. was added within 10 min N-iodo succinimide (0.58 g, 2.59 mmol), dissolved in methanol (3 mL). After stirring for 15 min, the reaction mixture was poured on ice and partly decolorized by addition of a 5% solution of sodium thiosulfate. The solution was extracted with ethyl acetate (3×50 mL), the combined organic phases dried over $MgSO_4$, concentrated by evaporation under reduced pressure and the crude material purified with column chromatography on silica eluting with ethyl acetate/methanol (9:1) providing 0.21 g (35%) of the title compound.

¹H NMR (300 MHz, DMSO): δ5.25 (br s, 2H), 6.61 (d, 1=1.9 Hz, 1H), 6.78 (d, J=1.9 Hz, 1H), 10.16 (br s, 1H), 12.58 (br s, 1H).

3-Amino-5-hydroxy-4-iodo-benzoic acid methyl ester

To a solution of 3-amino-5-hydroxy-4-iodo-benzoic acid (0.20 g, 0.72 mmol) in methanol (5 mL) was added conc. sulfuric acid (0.20 mL, 0.035 g, 0.36 mmol) and the reaction mixture heated to reflux. After 2 h, the reaction mixture was poured on ice, the pH adjusted to 9 by addition of a sat. solution of sodium hydrogencarbonate and extracted with ethyl acetate (2×50 mL). The combined organic phases were dried over $MgSO_4$, concentrated by evaporation under reduced pressure and the crude material purified with column chromatography on silica eluting with hexane/ethyl acetate (1:1) providing 0.07 g (33%) of the title compound.

¹H NMR (250 MHz, DMSO): δ3.78 (s, 3H), 5.45 (br s, 2H), 6.68 (s, 1H), 6.85 (s, 1H), 10.32 (br s, 1H).

3-Amino-5-ethoxy-4-iodo-benzoic acid methyl ester

To a solution of 3-amino-5-hydroxy-4-iodo-benzoic acid methyl ester (0.25 g, 0.85 mmol) in DMF (3 mL) and ethyl iodide (0.10 mL, 0.146 g, 0.94 mmol) at 0° C. was added sodium tert-butoxide (0.11 g, 0.94 mmol) in small portions over a time period of 10 min. After stirring for 1 h, the cooling bath was removed and the reaction mixture stirred at rt for an additional 18 h. The solution was concentrated by evaporation under reduced pressure and extracted with ethyl acetate (3×50 mL). The combined organic phases were dried over $MgSO_4$, concentrated by evaporation under reduced pressure and the crude material purified with column chromatography on silica eluting with hexane/ethyl acetate (2:1) yielding 0.19 g (69%) of the title compound.

¹H NMR (250 MHz, $CDCl_3$): δ1.49 (t, J=7.0 Hz, 3H), 3.89 (s, 3H), 4.11 (q, J=7.0 Hz, 2H), 4.33 (br s, 2H), 6.82 (d, J=2.7 Hz, 1H), 7.07 (d, J=2.7 Hz, 1H).

(3-Amino-5-ethoxy-4-iodo-phenyl)-methanol

To a solution of 3-amino-5-ethoxy-4-iodo-benzoic acid methyl ester (0.18 g, 0.56 mmol) in THF (5 mL) at 0° C. under Ar was slowly added diisobutylaluminium hydride (2.8 mL, 2.80 mmol, 1 M solution in THF) over a time period of 30 min, the cooling bath removed on completion of addition and the reaction allowed to reach rt. After 2 h, the excess hydride was quenched by cautious addition of a sat. solution of potassium sodium tartrate (50 mL). The solidified mixture was extracted with hot THF, the combined organic phases concentrated by evaporation under reduced pressure and the crude material purified with column chromatography on silica eluting with hexane/ethyl acetate (2:1) providing 0.056 g (34%) of the title compound.

¹H NMR (250 MHz, $CDCl_3$): δ1.47 (t, J=7.0 Hz, 3H), 4.08 (q, J=7.0 Hz, 2H), 4.23 (br s, 2H), 4.58 (d, J=6.0 Hz, 2H), 6.23 (s, 1H), 6.42 (s, 1H).

5-Amino-3-ethoxy-4-iodo-benzaldehyde

To a solution of (3-amino-5-ethoxy-4-iodo-phenyl)-methanol (4.9 g, 16.72 mmol) in dichloromethane (100 mL) was added $MnO_2$ (7.27 g, 83.59 mmol) and the reaction mixture heated to reflux for 3 h. Filtration through Hyflo, concentration by evaporation under reduced pressure and purification with column chromatography on silica eluting with hexane/ethyl acetate (3:1) yielded 3.14 g (60%) of the title compound.

¹H NMR (300 MHz, DMSO): δ1.37 (t, J=7.0 Hz, 3H), 4.15 (q, J=7.0 Hz, 2H), 4.49 (d, J=5.6 Hz, 2H), 5.21 (t, J=5.6 Hz, 1H), 6.82 (s, 1H), 6.85 (s, 1H), 11.64 (br s, 1H).

N-[1-(5-Amino-3-ethoxy-4-iodo-benzyl)piperidin-4-yl]-5-methyl-nicotinamide

The title compound (4 mg, 8%) was prepared analogously to example 30 from 5-methyl-N-(piperidin-4-yl)-nicotinamide and 5-amino-3-ethoxy-4-iodo-benzaldehyde. MS: 495.4 (MH⁺).

Example 39

N-[1-(3-Ethoxy-4-hydroxy-benzyl)piperidin-4-yl]-5-methyl-nicotinamide

The title compound (37 mg, 100%) was prepared analogously to example 30 from 5-methyl-N-(piperidin-4-yl)-nicotinamide and 3-ethoxy-4-hydroxy-benzaldehyde. MS: 370.5 (MH⁺).

Example 40

N-[1-(3,5-Diethoxy-4-pyrrol-1-yl-benzyl)piperidin-4-yl]-5-methyl-nicotinamide 3,5-Diethoxy-4-pyrrol-1-yl-benzoic acid ethyl ester To a solution of 4-amino-3,5-diethoxy-benzoic acid ethyl ester (3.0 g, 11.84 mmol, prepared as described in Helv. Chim. Acta 1977, 60, 3025-3034) in heptane (10 mL) and conc. acetic acid (0.2 mL) was added 2,5-dimethoxy-tetrahydrofuran (1.88 g, 14.21 mmol). After heating to reflux for 5 h, a Dean-Stark apparatus was attached and the reaction mixture heated for an additional time period of 5 h. Filtration of the crude reaction mixture and crystallisation at 0° C. from heptane provided 2.94 g (82%) of the title compound.
$^1$H NMR (300 MHz, DMSO): δ1.15 (t, J=7.0 Hz, 6H), 1.27 (t, J=7.1 Hz, 3H), 3.98 (q, J=7.0 Hz, 4H), 4.28 (q, J=7.1 Hz, 2H), 6.07-6.08 (m, 2H), 6.73-6.74 (m, 2H), 7.22 (s, 2H).

3,5-diethoxy-4-pyrrol-1-yl-benzaldehyde

To a solution of 3,5-diethoxy-4-pyrrol-1-yl-benzoic acid ethyl ester (1.51 g, 4.98 mmol) in toluene (5 mL) was added slowly over a time period of 15 min under slight cooling to 20° C. a solution of diisobutylaluminium hydride (8.9 mL, 12.45 mmol, 20% solution in toluene). After 1 h, the excess hydride was quenched by cautious addition of water (10 mL) and a 28% solution of sodium hydoxide (2 mL). The mixture was stirred for 30 min and the organic phase filtered over Hyflo. The aqueous layer was extracted with toluene (2×50 mL), the combined organic phases washed with a sat. solution of sodium chloride (2×50 mL) and concentrated by evaporation under reduced pressure to afford 1.30 g (100%) of (3,5-diethoxy-4-pyrrol-1-yl-phenyl)-methanol. The crude alcohol (1.30 g, 4.98 mmol, 1.0 equiv) was dissolved in toluene (20 mL) and MnO$_2$ (7.79 g, 89.5 mmol, 18.0 equiv) was added. The reaction mixture was heated to reflux for 7 h, after which time the reaction was filtered through Hyflo and concentrated yielding 1.15 g (89% yield) of the title compound.
$^1$H NMR (300 MHz, DMSO): δ1.17 (t, J=7.0 Hz, 6H), 4.02 (q, J=7.0 Hz, 4H), 6.08-6.09 (m, 2H), 6.75-6.76 (m, 2H), 7.25 (s, 2H), 9.89 (s, 1H).

[1-(3,5-Diethoxy-4-pyrrol-1-yl-benzyl)piperidin-4-yl]-5-methyl-nicotinamide

The title compound (10 mg, 22%) was prepared analogously to example 30 from 5-methyl-N-(piperidin-4-yl)-nicotinamide and 3,5-diethoxy-4-pyrrol-1-yl-benzaldehyde. MS: 463.5 (MH+)

Example 41

N-[1-(3-Ethoxy-4-methoxy-benzyl)piperidin-4-yl]-5-methyl-nicotinamide

The title compound (10 mg, 26%) was prepared analogously to example 30 from 5-methyl-N-(piperidin-4-yl)-nicotinamide and 3-ethoxy-4-ethoxy-benzaldehyde. MS: 384.5 (MH$^+$).

Example 42

N-[1-(4-Chloro-3-ethoxy-benzyl)piperidin-4-yl]-6-(cyclopropanecarbonyl-amino)-nicotinamide The title compound (12 mg, 26%) was prepared analogously to example 7 by coupling of 6-amino-N-[1-(4-chloro-3-ethoxy-benzyl)piperidin-4-yl]-nicotinamide with cyclopropanecarbonyl chloride. MS: 457.4 (MH$^+$).

Example 43

N-[1-(4-Chloro-3-ethoxy-benzyl)piperidin-4-yl]-5-(cyclopropanecarbonyl-amino)-nicotinamide The title compound (12 mg, 26%) was prepared analogously to example 7 by coupling of 5-amino-N-[1-(4-chloro-3-ethoxy-benzyl)piperidin-4-yl]-nicotinamide with cyclopropanecarbonyl chloride. MS: 457.4 (MH$^+$).

Example 44

5-Acetylamino-N-[1-(4-chloro-3-ethoxy-benzyl)piperidin-4-yl]-nicotinamide

The title compound (12 mg, 26%) was prepared analogously to example 7 by coupling of 5-amino-N-[1-(4-chloro-3-ethoxy-benzyl)piperidin-4-yl]-nicotinamide with acetyl chloride. MS: 431.4 (MH$^+$).

Example 45

N-[1-(3-Ethoxy-4-methoxy-2-pyridine-4-yl-)piperidin-4-yl-benzyl]-5-methyl-nicotinamide 2-Carbonyl-4-ethoxy 5-methoxy-phenylboronic acid To a solution of of 2-(2-bromo-5-ethoxy-4-methoxy-phenyl)-[1,3-dioxolane] (3.15 g, 10 mmol) (prepared from 2-bromo-5-ethoxy-4-methoxy-benzaldehyde (CA 56517-30-7, J. Med. Chem. 1975, 18(7), 708) and ethylene glycol under Dean-Stark conditions) in anhydrous THF (30 mL) under Ar cooled to −78° C. was added n-BuLi (9.1 mL, 1.6 M in hexanes, 15 mmol), and the reaction stirred for 0.5 h. Trimethyl borate (3.48 mL, 31 mmol) was then added rapidly and the reaction allowed to slowly reach room temperature (4 h). 1 M HCl (aq) was then added to the reaction to bring the pH to 1. The reaction was stirred for a further 1 h. The reaction was then extracted with DCM, and the combined organic washed with water, dried (Na$_2$SO$_4$) and concentrated. The residue was crystallised from EtOAc:Heptane 1:1 affording the title compound (0.56 g, 24% yield) as a off-white powder.
$^1$H NMR (300 MHz, CDCl$_3$): δ1.53 (t, J=7.0 Hz, 3H), 4.03 (s, 3H), 4.22 (q, J=7.0 Hz, 2H), 7.38-7.39 (m, 1H), 7.79 (s, 1H), 9.75 (s, 1H).

N-[1-(3-Ethoxy-2-dihydroxyboronyl-4-methoxy-benzyl)piperidin-4-yl]-5-methyl-nicotinamide To a solution of 5-methyl-N-(piperidin-4-yl)-nicotinamide (0.33 g, 2 mmol) and 2-carbonyl-4-ethoxy 5-methoxy-phenylboronic acid (0.35 g, 2 mmol) in DCM (20 mL) was added acetic acid (0.09 mL, 2 mmol) and sodium triacetoxyborohydride (0.7 g, 3 mmol). The reaction was stirred for 3 h after which time it was diluted with DCM, washed with saturated NaHCO$_3$, dried (Na$_2$SO$_4$) and concentrated to afford the title compound (0.57 g, 89%) without need for further purification.
$^1$H NMR (300 MHz, CDCl$_3$): δ1.41 (t, J=6.9 Hz, 3H), 1.52-1.60 (m, 2H), 2.04-2.07 (m, 2H), 2.19-2.24 (m, 2H), 2.38 (s, 3H), 2.85-3.05 (m, 2H), 3.59 (s, 2H), 4.08-4.17 (m, 3H), 6.13 (d, J=8.7 Hz, 1H), 6.68 (s, 1H), 7.45 (s, 1H), 7.90 (s, 1H), 8.54 (s, 1H), 8.75 (s, 1H).

N-[1-(3-Ethoxy-4-methoxy-2-pyridine-4-yl-)piperidin-4-yl-benzyl]-5-methyl-nicotinamide To a degassed solution of N-[1-(3-ethoxy-2-dihydroxyboronyl-4-methoxy-benzyl)piperidin-4-yl]-5-methyl-nicotinamide (43 mg, 0.1 mmol,) in a mixture of dimethoxyethane: water (2:11 ml) was added 4-bromopyridine hydrochloride (23 mg, 0.12 mmol), potassium tert-butylate (89 mg, 0.8 mmol) and tetrakis(triphenylphosphine) palladium(0) (7 mg, 0.06 mmol) and the reaction mixture stirred at 85° C. for 16 h under Ar. Removal of the solvent under reduced pressure and purification by reversed phase HPLC (MeCN:H$_2$O) provided the title compound (2 mg, 4%). MS: 461.5 (MH$^+$).

Example 46

N-[1-(3-Ethoxy-4-methoxy-2-pyrimidin-5-yl-benzyl) piperidin-4-yl]-5-methyl-nicotinamide The title compound (6 mg, 13%) was prepared analogously to example 45 by coupling of N-[1-(3-ethoxy-2-dihydroxy-boronyl-4-methoxy-benzyl)piperidin-4-yl]-5-methyl-nicotinamide with 5-bromopyrimidine. MS: 462.5 (MH$^+$).

Example 47 rac-N-1-[1-(4-Chloro-3-ethoxy-phenyl)piperidin-4-yl]-ethyl)-5-methyl-nicotinamide 1-(4-Chloro-3-ethoxy-phenyl)-ethanone 4-Chloro-3-ethoxy-benzaldehyde (0.3 g, 2 mmol) was dissolved in THF (5 ml) under Ar and cooled in an ice bath. A solution of MeMgBr (0.8 ml, 3 M in Et$_2$O, 3 mmol) was added dropwise and the reaction stirred for 1 h. After which time the reaction was queched by addition of saturated NH$_4$Cl, and the reaction extracted with DCM. The organic phase was dried (Na$_2$SO$_4$) and concentrated affording 0.3 g of crude product. This was then redissolved in DCM, MnO$_2$ (0.6 mg, 7 mmol) was added and the reaction stirred for 16 h. The reaction was then filtered through a pad of Hyflo and concentrated affording the title compound (0.3 g, 96%) as a yellow solid. $^1$H NMR (300 MHz, CDCl$_3$): δ1.47 (t, J=7.1 Hz, 3H), 2.59 (s, 3H), 4.17 (q, J=7.1 Hz, 2H), 7.45 (4, 2H), 7.53 (s, 1H).

rac-N-{1-[1-(4-Chloro-3-ethoxy-phenyl)piperidin-4-yl]-ethyl}-5-methyl-nicotinamide To a solution of 1-(4-chloro-3-ethoxy-phenyl)-ethanone (20 mg, 0.1 mmol) and 5-methyl-N-(piperidin-4-yl)-nicotinamide (21 mg, 0.1 mmol) in a mixture of EtOH:DCE 1:1 (1 ml) was added Ti(i-PrO)$_4$ (65 μL, 0.2 mmol) and the reaction heated at 70° C. allowing the solvent to evaporate to dryness. The reaction was further dried under high vacuum before redissolving in DCE (1 ml) and adding sodium triacetoxy-borohydride (25 mg, 0.1 mmol). After stirring for 2 days, the reaction was diluted with DCM, washed with saturated NaHCO$_3$, dried (Na$_2$SO$_4$) and concentrated. The residue was purified by flash column chromatography (DCM:MeOH 95:5) to afford the title product (21 mg, 54%).

$^1$H NMR (300 MHz, CDCl$_3$): δ1.49 (t, J=6.9 Hz, 3H) 1.69-1.73 (m, 2H), 2.00-2.04 (m, 5H), 2.19-2.22 (m, 2H), 2.38 (s, 3H), 2.88-2.92 (m, 1H), 3.14-3.18 (m, 2H), 3.95-4.05 (m, 1H), 4.13 (q, J=6.9 Hz, 2H), 6.47 (d, J=7.8 Hz, 1H), 6.82-6.84 (m, 1H), 6.98 (s, 1H), 7.30 (d, J=8.1 Hz, 1H), 7.94 (s, 1H), 8.53 (s, 1H), 8.76 (s, 1H).

Example 48

N-[1-(4-Chloro-3-ethoxy-benzyl)-piperidin-4-yl]-isophthalamic acid methyl ester

The title compound (80 mg, 92%) was prepared analogously to example 8 by coupling of 1-(4-chloro-3-ethoxy-benzyl)piperidin-4-ylamine with isophthalic acid monomethyl ester. MS: 431.6 (MH$^+$).

Example 49

N-[1-(4-Chloro-3-ethoxy-benzyl)-piperidin-4-yl]-isophthalamic acid

The title compound (40 mg, 68%) was prepared by heating example 48 (60 mg, 0.1 mmol) with aqueous NaOH (0.05 mL, 0.2 mmol, 6 N) in MeOH (2 mL) at 60° C. for 24 h. The reaction was acidified with Amberlite IR120 plus resin, filtered and concentrated to afford the title compound. MS: 417.4 (MH$^+$).

Example 50

2-{3-[1-(3,5-Diethoxy-4-fluoro-benzyl)-piperidin-4-ylcarbamoyl]-phenoxy}-2-methyl-propionic acid ethyl ester tert-Butyl-(4-fluoro-benzyloxy)-dimethyl-silane To a solution of (4-fluoro-phenyl)-methanol (12.16 g, 96.4 mmol, 1.0 eq.) in anhydrous DMF (50 mL) at 0° C. under Ar was added imidazole (7.22 g, 106.1 mmol, 1.1 eq.) and tert-butyl-chloro-dimethyl-silane (15.99 g, 106.1 mmol, 1.1 eq.). After the addition was completed the cooling bath was removed and the reaction stirred for 18 h at rt. The reaction mixture was poured on ice, extracted with ethyl acetate (2×100 mL) and the combined organic phases washed with a sat. solution of sodium carbonate (2×100 mL) and sodium chloride (2×100 mL). The organic phase was dried over Na$_2$SO$_4$, concentrated by evaporation under reduced pressure yielding a brown oil that was purified by high vacuum destillation (bp 32-35° C. at 0.1 mbar) to give 23.0 g (99%) of the title compound. $^1$H NMR (400 MHz, CDCl$_3$): δ0.00 (s, 6H), 0.84 (s, 9H), 4.60 (s, 2H), 6.89-6.94 (m, 2H), 7.16-7.20 (m, 2H). MS: 183.1 [M-tert-Bu]$^+$.

5-(tert-Butyl-dimethyl-silanyloxymethyl)-2-fluorophenol

To a solution of tert-butyl-(4-fluoro-benzyloxy)-dimethyl-silane (5.00 g, 20.8 mmol, 1.0 eq.) in anhydrous THF (20 mL) was added at −78° C. under Ar a solution of sec-BuLi (17.6 mL, 22.8 mmol, 1.1 eq., 1.3 M solution in hexane) within 30 min. Then a solution of trimethyl borate (2.37 mL, 2.20 g, 20.8 mmol, 1.0 eq.) in anhydrous THF (7.5 mL) was added slowly within 30 min and the cooling bath removed. A solution of conc. acetic acid (2.78 mL, 1.87 g, 31.2 mmol, 1.5 eq.) was slowly added followed by addition of 35% hydrogen peroxide (2.22 mL, 0.78 g, 22.9 mmol, 1.1 eq.) and the reaction mixture kept at 0° C. for 30 min. After stirring at rt for an additional 4 h, the reaction was extracted with diethyl ether (2×100 mL) and the combined organic phases washed with a solution of 10% sodium hydroxide (2×100 mL) and a sat. solution of sodium chloride (2×100 mL). The organic phase was dried over Na$_2$SO$_4$, concentrated by evaporation under reduced pressure and the crude material purified with column chromatography on silica eluting with hexane/ethyl acetate (19:1) providing 4.80 g (90%) of the title compound. $^1$H NMR (400 MHz, CDCl$_3$): δ0.00 (s, 6H), 0.84 (s, 9H), 4.56 (s, 2H), 4.97 (br s, 1H), 6.68-6.72 (m, 1H), 6.87-6.94 (m, 2H). MS: 256.2 (M$^+$).

2-(tert-Butyl-dimethyl-silanyloxy)-4-(tert-butyl-dimethyl-silanyloxymethyl)-1-fluoro-benzene To a solution of 5-(tert-butyl-dimethyl-silanyloxymethyl)-2-fluoro-phenol (4.60 g, 17.9 mmol, 1.0 eq.) in anhydrous DMF (20 mL) at 0° C. under Ar was added imidazole (1.34 g, 19.7 mmol, 1.1 eq.) and tert-butyl-chloro-dimethyl-silane (2.97 g, 19.7 mmol, 1.1 eq.). After the addition was completed the cooling bath was removed and the reaction stirred for 18 h at rt. The reaction mixture was poured on ice, extracted with ethyl acetate (2×100 mL) and the combined organic phases washed with a sat. solution of sodium carbonate (2×100 mL) and sodium chloride (2×100 mL). The organic phase was dried over $Na_2SO_4$ and concentrated by evaporation under reduced pressure yielding 4.50 g (68%) of the title compound. $^1$H NMR (400 MHz, CDCl$_3$): δ(0.00 (s, 6H), 0.10 (s, 6H), 0.85 (s, 9H), 0.92 (s, 9H), 4.55 (s, 2H), 6.71-6.74 (m, 1H), 6.80-6.83 (m, 1H), 6.87-6.92 (m, 1H). MS: 370.2 (M$^+$).

3-(tert-Butyl-dimethyl-silanyloxy)-5-(tert-butyl-dimethyl-silanyloxymethyl)-2-fluoro-phenol To a solution of 2-(tert-butyl-dimethyl-silanyloxy)-4-(tert-butyl-dimethyl-silanyloxymethyl)-1-fluoro-benzene (23.70 g, 63.9 mmol, 1.0 eq.) in anhydrous THF (130 mL) was added at −78° C. under Ar a solution of sec-BuLi (54.5 mL, 71.6 mmol, 1.1 eq., 1.3 M solution in hexane) within 30 min. Then a solution of trimethyl borate (7.13 mL, 6.64 g, 63.9 mmol, 1.0 eq.) in anhydrous THF (30 mL) was added slowly within 30 min and the cooling bath removed. A solution of conc. acetic acid (5.49 mL, 5.76 g, 95.9 mmol, 1.5 eq.) was slowly added followed by addition of 35% hydrogen peroxide (6.28 mL, 2.39 g, 70.3 mmol, 1.1 eq.) and the reaction mixture kept at 0° C. for 30 min. After stirring at rt for an additional 4 h, the reaction was extracted with diethyl ether (2×100 mL) and the combined organic phases washed with a solution of 10% sodium hydroxide (2×100 mL) and a sat. solution of sodium chloride (2×100 mL). The organic phase was dried over $Na_2SO_4$, concentrated by evaporation under reduced pressure and the crude material purified with column chromatography on silica eluting with hexane/ethyl acetate (19:1) providing 15.80 g (64%) of the title compound. $^1$H NMR (400 MHz, CDCl$_3$): δ0.00 (s, 6H), 0.10 (s, 6H), 0.85 (s, 9H), 0.91 (s, 9H), 4.50 (s, 2H), 4.93 (br s, 1H), 6.37 (d, J=5.6 Hz, 1H), 6.47 (d, J=5.6 Hz, 1H). MS: 329.2 [M-tert-Bu]$^+$.

tert-Butyl-(3,5-diethoxy-4-fluoro-benzyloxy)-dimethyl-silane

To a solution of 3-(tert-butyl-dimethyl-silanyloxy)-5-(tert-butyl-dimethyl-silanyloxymethyl)-2-fluoro-phenol (5.80 g, 15.0 mmol, 1.0 eq.) in DMF (60 mL) was added potassium carbonate (4.56 g, 33.0 mmol, 2.2 eq.) and ethyl bromide (2.46 mL, 3.60 g, 33.0 mmol, 2.2 eq.) and the reaction mixture stirred under Ar at 60° C. for 5 h. The potassium carbonate was removed by filtration, the crude reaction mixture concentrated by evaporation under reduced pressure, the residue extracted with ethyl acetate (3×100 mL), the combined organic phases washed with water (2×100 mL) and dried over $Na_2SO_4$. The solvent was removed by evaporation under reduced pressure and the crude material purified with column chromatography on silica eluting with hexane/ethyl acetate (99:1) providing 3.10 g (63%) of the title compound. $^1$H NMR (400 MHz, CDCl$_3$): δ0.00 (s, 6H), 0.85 (s, 9H), 1.33 (t, J=7.0 Hz, 6H), 4.00 (q, J=7.0 Hz, 4H), 4.55 (s, 2H), 6.47 (d, J=6.8 Hz, 2H). MS: 329.3 (MH$^+$).

(3,5-Diethoxy-4-fluoro-phenyl)-methanol

To a solution of tert-butyl-(3,5-diethoxy-4-fluoro-benzyloxy)-dimethyl-silane (1.20 g, 3.65 mmol, 1.0 eq.) in methanol (8 mL) was added Dowex 50W-X8 (0.33 g) and the reaction mixture stirred under Ar at rt for 22 h. The resin was removed by filtration and the reaction mixture concentrated by evaporation under reduced pressure yielding the title compound in quantitative yield (0.78 g). $^1$H NMR (400 MHz, CDCl$_3$): δ1.34 (t, J=7.0 Hz, 6H), 1.57 (t, J=5.4 Hz, 1H), 4.01 (q, J=7.0 Hz, 4H), 4.51 (d, J=5.4 Hz, 2H), 6.51 (d, J=6.8 Hz, 2H). MS: 214.2 (M$^+$).

3,5-Diethoxy-4-fluoro-benzaldehyde

To a solution of (3,5-diethoxy-4-fluoro-phenyl)-methanol (2.30 g, 10.7 mmol, 1.0 eq.) in 1,2-dichloroethane (50 mL) was added MnO$_2$ (2.89 g, 33.3 mmol, 3.1 eq.). The reaction mixture was stirred for 21 h at 50° C. and filtered through Hyflo providing 1.90 g (83%) of the title compound. $^1$H NMR (400 MHz, CDCl$_3$): δ1.38 (t, J=7.0 Hz, 6H), 4.09 (q, J=7.0 Hz, 4H), 7.04 (d, J=7.2 Hz, 2H), 9.75 (s, 1H). MS: 212.1 (M$^+$).

4-[3-(1-Ethoxycarbonyl-1-methyl-ethoxy)-benzoylamino]-piperidine-1-carboxylic acid tert-butyl ester 1.30 g (5.0 mmol) of 3-(1-ethoxycarbonyl-1-methylethoxy)-benzoic acid [U.S. Pat. Appl. Publ. (2005), 89 pp. US 2005096337 A1] and 0.969 g (5.25 mmol) of 2-chloro-4,6-dimethoxy-1,3,5-triazine were dissolved under argon in 5 mL of MeCN and cooled down to 0° C.; then, 1.10 mL (1.064 g=2.0 eq.) of N-methylmorpholine was added and the mixture was stirred at 0° C. for 2 h. To this mixture was added 1.277 g (6.0 mmol) 4-amino-piperidine-carboxylic acid tert-butyl ester in small portions; afterwards the reaction was then warmed up to rt. After stirring for 16 h, it was poured into crashed ice and extracted twice with MeCl$_2$; the organic phases were washed with water, dried over MgSO$_4$, filtered and evaporated i.V. to yield 2.18 g of the crude title compound as off-white solid. MS: 435.2 (MH$^+$).

2-Methyl-2-[3-(piperidin-4-ylcarbamoyl)-phenoxy]-propionic acid ethyl ester 2.08 g (5.0 mmol) of 4-[3-(1-ethoxycarbonyl-1-methylethoxy)-benzoylamino]-piperidine-1-carboxylic acid tert-butyl ester was dissolved under argon in 80 mL of MeCl$_2$; to the stirred solution, 3.66 mL (5.46 g=10 eq.) of TFA was added drop by drop and stirring continued at rt for 5 h. Then, the reaction mixture was evaporated i.V., the residue was dissolved in MeCl$_2$ and water, the pH was adjusted to ~10 with sodium carbonate solution and the mixture was extracted twice with MeCl$_2$; the organic phases were washed with water, dried over MgSO$_4$, filtered and evaporated i.V. The crude product was purified by chromatography (silicagel, eluent:gradient of MeCl$_2$/MeOH) to yield 1.20 g of the title compound as colorless oil. MS: 335.2 (MH$^+$).

2-{3-[1-(3,5-Diethoxy-4-fluoro-benzyl)-piperidin-4-ylcarbamoyl]-phenoxy}-2-methyl-propionic acid ethyl ester 0.33 g (1.0 mmol) of 2-methyl-2-[3-(piperidin-4-ylcarbamoyl)-phenoxy]-propionic acid ethyl ester and 0.23 g (1.10 eq.) of 3,5-diethoxy-4-fluoro-benzaldehyde (example 50 g), were dissolved under argon in 6 mL of MeOH; 0.39 mL (0.29 g=2.25 eq.) of N-ethyl-diisopropylamine and 0.11 mL (0.12 g=2.0 eq.) of glacial acetic acid were added and the mixture then heated for 2 h at 50° C. After cooling down to rt, 0.16 g (2.5 eq.) of sodium cyanoborohydride was added and the reaction mixture heated again for 1.5 h at 50° C. It was then poured into crashed ice, the pH was adjusted to ~10 with sodium carbonate solution and the mixture was extracted twice with MeCl$_2$; the organic phases were washed with water, dried over MgSO$_4$, filtered and evaporated i.V. The crude product was purified by chromatography (silicagel, eluent:gradient of MeCl$_2$/MeOH) to yield 0.50 g of the title compound as colorless oil. MS: 531.2 (MH$^+$).

Example 51

2-{3-[1-(3,5-Diethoxy-4-pyrrol-1-yl-benzyl)-piperidin-4-ylcarbamoyl]-phenoxy}-2-methyl-propionic acid ethyl ester In analogy to the procedure described in example 50k), 2-methyl-2-[3-(piperidin-4-ylcarbamoyl)-phenoxy]-propionic acid ethyl ester (example 50i) was reacted with 3,5-diethoxy-4-pyrrol-1-yl-benzaldehyde (example 40b), sodium cyanoborohydride, N-ethyl-diisopropylamine and acetic acid in ethanol at 50° C. to yield the title compound as colorless foam. MS: 578.3 (MH$^+$).

Example 52

2-{3-[1-(3-Ethoxy-4-methoxy-benzyl)-piperidin-4-ylcarbamoyl]-phenoxy}-2-methyl-propionic acid ethyl ester In analogy to the procedure described in example 50k), 2-methyl-2-[3-(piperidin-4-ylcarbamoyl)-phenoxy]-propionic acid ethyl ester (example 50i) was reacted with 3-ethoxy-4-methoxybenzaldehyde, sodium cyanoborohydride, N-ethyl-diisopropylamine and acetic acid in ethanol at 50° C. to yield the title compound as colorless foam. MS: 499.2 (MH$^+$).

Example 53

2-{3-[1-(3,5-Diethoxy-4-fluoro-benzyl)-piperidin-4-ylcarbamoyl]-phenoxy}-2-methyl-propionic acid 0.54 g (1.0 mmol) of 2-{3-[1-(3,5-diethoxy-4-fluoro-benzyl)-piperidin-4-ylcarbamoyl]-phenoxy}-2-methyl-propionic acid ethyl ester (example 50k) was reacted with 1.0 mL of LiOH/water (1.0 molar) in 15 mL of THF/MeOH (2:1) at 0° C. and subsequent temperature increase to rt. After 5 h, the reaction mixture was poured into crashed ice, the pH was adjusted to ~7.0 with aq. HCl (1N) and the reaction mixture was extracted twice with MeCl$_2$; the organic phases were washed with water, dried over MgSO$_4$, filtered and evaporated i.V. The crude product was purified by chromatography (silicagel, eluent:gradient of MeCl$_2$/MeOH) to yield 0.135 g of the title compound as colorless solid. MS: 503.1 (MH$^+$).

Example 54

2-{3-[1-(3,5-Diethoxy-4-pyrrol-1-yl-benzyl)-piperidin-4-ylcarbamoyl]-phenoxy}-2-methyl-propionic acid In analogy to the procedure described in example 53, 2-{3-[1-(3,5-diethoxy-4-pyrrol-1-yl-benzyl)-piperidin-4-ylcarbamoyl]-phenoxy}-2-methyl-propionic acid ethyl ester (example 51) was saponified to yield the title compound as colorless solid. MS: 550.3 (MH$^+$).

Example 55

2-{3-[1-(3-Ethoxy-4-methoxy-benzyl)-piperidin-4-ylcarbamoyl]-phenoxy}-2-methyl-propionic acid In analogy to the procedure described in example 53, 2-{3-[1-(3-ethoxy-4-methoxy-benzyl)-piperidin-4-ylcarbamoyl]-phenoxy}-2-methyl-propionic acid ethyl ester (example 52) was saponified to yield the title compound as colorless solid. MS: 471.1 (MH$^+$).

Example 56

Pyrimidine-5-carboxylic acid[1-(3,5-diethoxy-4-fluoro-benzyl)-piperidin-4-yl]-amide In analogy to the procedure described in example 50k), pyrimidine-5-carboxylic acid piperidin-4-ylamide [prepared in analogy to the procedures described in examples 50 h) and 50i) by condensation of pyrimidine-5-carboxylic acid with 4-amino-piperidine-carboxylic acid tert-butyl ester to give 4-[(pyrimidine-5-carbonyl)-amino]-piperidine-1-carboxylic acid tert-butyl ester followed by Boc cleavage with trifluoro-acetic acid] was reacted with 3,5-diethoxy-4-fluoro-benzaldehyde (example 50 g), sodium cyano-borohydride, N-ethyl-diisopropylamine and acetic acid in ethanol at 50° C. to yield the title compound as light yellow solid. MS: 403.3 (MH$^+$).

Example 57

Pyrimidine-5-carboxylic acid[1-(3,5-diethoxy-4-pyrrol-1-yl-benzyl)-piperidin-4-yl]-amide In analogy to the procedure described in example 50k), pyrimidine-5-carboxylic acid piperidin-4-ylamide (example 56) was reacted with 3,5-diethoxy-4-pyrrol-1-yl-benzaldehyde (example 40b), sodium cyanoborohydride, N-ethyl-diisopropylamine and acetic acid in ethanol at 50° C. to yield the title compound as light yellow solid. MS: 450.2 (MH$^+$).

Example 58

Pyrimidine-5-carboxylic acid[1-(3-ethoxy-4-methoxy-benzyl)-piperidin-4-yl]-amide In analogy to the procedure described in example 50k), pyrimidine-5-carboxylic acid piperidin-4-ylamide (example 56) was reacted with 3-ethoxy-4-methoxy-benzaldehyde, sodium cyanoborohydride, N-ethyl-diisopropylamine and acetic acid in ethanol at 50° C. to yield the title compound as colorless solid. MS: 371.1 (MH$^+$).

Example 59

Pyrimidine-5-carboxylic acid[1-(3-ethoxy-4-fluoro-benzyl)-piperidin-4-yl]-amide

In analogy to the procedure described in example 50k), pyrimidine-5-carboxylic acid piperidin-4-ylamide (example 56) was reacted with 3-ethoxy-4-fluoro-benzaldehyde [prepared from 3-hydroxy-4-fluoro-benzoic acid in analogy to the procedure described for the synthesis of 4-chloro-3-ethoxy-benzaldehyde in example 1a)], sodium cyano-borohydride, N-ethyl-diisopropylamine and acetic acid in ethanol at 50° C. to yield the title compound as light yellow solid. MS: 359.1 (MH$^+$).

Example 60

2-{4-[1-(3-Ethoxy-4-methoxy-benzyl)-piperidin-4-ylcarbamoyl]-phenyl}-2-methyl-propionic acid methyl ester

2-Methyl-2-phenyl-propionic acid methyl ester 9.00 g (55 mmol) 2-methyl-2-phenyl-propionic acid was dissolved in 90 ml N,N-dimethylformamide, 11.51 g (2.5 eq.) of sodium hydrogencarbonate was added followed by 6.89 mL (15.72 g 2 eq.) of methyl iodide. The mixture was stirred at rt for 40 hours, then poured into ice water, the pH was adjusted to ~3.0 with aq. HCl (1N) and the mixture extracted 3 times with ether; the organic phases were washed with water, dried over MgSO$_4$, filtered and evaporated to give 7.34 g of the crude title compound as yellow oil. MS: 178.1 (M$^+$).

2-(4-Formyl-phenyl)-2-methyl-propionic acid methyl ester 6.80 g (38 mmol) of 2-methyl-2-phenyl-propionic acid methyl ester was dissolved at rt in 200 mL MeCl$_2$ and 7.01 ml (90.4 g=76 mmol) of dichloromethylmethylether was added and the mixture cooled down to 0° C.; 21.47 mL (36.93 g=191 mmol) TiCl$_4$ was added over 15 min and the reaction warmed up to ambient temperature; stirring was continued for 16 hours. The reaction mixture was then treated at 0° C. with 20 ml of HCl (37% in water) and extracted twice with MeCl$_2$; the organic phases were washed with water, dried over MgSO$_4$, filtered and evaporated. The crude product was purified by chromatography (silicagel, eluent:gradient of n-heptane/EtOAc) to yield 5.00 g of the title compound as yellow oil. MS: 206.1 (M$^+$).

4-(1-Methoxycarbonyl-1-methyl-ethyl)-benzoic acid 5.60 g (27 mmol) of 2-(4-formyl-phenyl)-2-methyl-propionic acid methyl ester was dissolved in 112 mL of tert-butanol; 16.97 mL (11.20 g=136 mmol) of 2-methyl-2-butene was added, followed by a solution of 7.98 g (71 mmol) of sodium chlorite and 6.35 g (41 mmol) of sodium dihydrogen phosphate in 56 mL of water. After 20 hours, the reaction mixture was poured into crashed ice/EtOAc, the pH was adjusted to ~3.0 with aq. HCl (1N) and it was extracted twice with EtOAc; the organic phases were washed with water, dried (MgSO$_4$), filtered and evaporated. The crude product was purified by recrystallisation from EtOAc/heptane to give 3.00 g of the title compound as colorless solid. MS: 221.2 [(M−H)$^-$].

4-[4-(1-Methoxycarbonyl-1-methyl-ethyl)-benzoylamino]-piperidine-1-carboxylic acid tert-butyl ester 0.780 g (3.78 mMol) of 4-amino-piperidine-carboxylic acid tert-butyl ester was suspended in 10 mL of MeCl$_2$ at rt under argon; then, 0.80 g (3.60 mmol) of 4-(1-methoxycarbonyl-1-methyl-ethyl)-benzoic acid, 0.845 g (1.20 eq.) of N-(3-dimethylaminopropyl)-N'-ethyl-carbodiimide hydrochloride and 0.583 g (1.30 eq.) of N,N-dimethyl-4-aminopyridine were added. The reaction mixture became a clear solution after stirring for 1 h at rt. After 5 hours, the solution was evaporated i.V. and the residue was purified by chromatography (silicagel, eluent:MeCl$_2$) to yield 1.28 g of the title compound as colorless foam. MS: 405.3 (MH$^+$).

2-{4-[1-(3-Ethoxy-4-methoxy-benzyl)-piperidin-4-ylcarbamoyl]-phenyl}-2-methyl-propionic acid methyl ester In analogy to the procedure described in example 50k), 2-methyl-2-[4-(piperidin-4-ylcarbamoyl)-phenyl]-propionic acid methyl ester [prepared from 4-[4-(1-methoxycarbonyl-1-methyl-ethyl)-benzoylamino]-piperidine-1-carboxylic acid tert-butyl ester by treatment with TFA in dichloromethane in analogy to the preparation described in example 50i)] was reacted with 3-ethoxy-4-methoxybenzaldehyde, sodium cyanoborohydride, N-ethyl-diisopropylamine and acetic acid in ethanol at 50° C. to yield the title compound as colorless foam. MS: 469.3 (MH$^+$).

Example 61

2-{4-[1-(3,5-Diethoxy-4-fluoro-benzyl)-piperidin-4-ylcarbamoyl]-phenyl}-2-methyl-propionic acid methyl ester In analogy to the procedure described in example 50k), 2-methyl-2-[4-(piperidin-4-ylcarbamoyl)-phenyl]-propionic acid methyl ester (example 60e) was reacted with 3,5-diethoxy-4-fluoro-benzaldehyde (example 50 g), sodium cyanoborohydride, N-ethyl-diisopropylamine and acetic acid in ethanol at 50° C. to yield the title compound as colorless solid. MS: 501.2 (MH$^+$).

Example 62

2-{4-[1-(3,5-Diethoxy-4-pyrrol-1-yl-benzyl)-piperidin-4-ylcarbamoyl]-phenyl}-2-methyl-propionic acid methyl ester In analogy to the procedure described in example 50k), 2-methyl-2-[4-(piperidin-4-ylcarbamoyl)-phenyl]-propionic acid methyl ester (example 60e) was reacted with 3,5-diethoxy-4-pyrrol-1-yl-benzaldehyde (example 40b), sodium cyanoborohydride, N-ethyl-diisopropylamine and acetic acid in ethanol at 50° C. to yield the title compound as light yellow foam. MS: 548.4 (MH$^+$).

Example 63

2-{4-[1-(3-Ethoxy-4-methoxy-benzyl)-piperidin-4-ylcarbamoyl]-phenyl}-2-methyl-propionic acid In analogy to the procedure described in example 53, 2-{4-[1-(3-ethoxy-4-methoxy-benzyl)-piperidin-4-ylcarbamoyl]-phenyl}-2-methyl-propionic acid methyl ester (example 60e) was saponified to yield the title compound as colorless solid. MS: 453.4 [(M−H)$^-$].

Example 64

2-{4-[1-(3,5-Diethoxy-4-fluoro-benzyl)-piperidin-4-ylcarbamoyl]-phenyl}-2-methyl-propionic acid In analogy to the procedure described in example 53, 2-{4-[1-(3,5-diethoxy-4-fluoro-benzyl)-piperidin-4-ylcarbamoyl]-phenyl}-2-methyl-propionic acid methyl ester (example 61) was saponified to yield the title compound as colorless solid. MS: 485.4 [(M−H)$^-$].

Example 65

2-{4-[1-(3,5-Diethoxy-4-pyrrol-1-yl-benzyl)-piperidin-4-ylcarbamoyl]-phenyl}-2-methyl-propionic acid In analogy to the procedure described in example 53, 2-{4-[1-(3,5-diethoxy-4-pyrrol-1-yl-benzyl)-piperidin-4-ylcarbamoyl]-phenyl}-2-methyl-propionic acid methyl ester (example 62) was saponified to yield the title compound as light yellow solid. MS: 532.4 [(M−H)⁻].

Example 66

2-{3-[1-(3,5-Diethoxy-4-fluoro-benzyl)-piperidin-4-ylcarbamoyl]-5-methoxy-phenoxy}-2-methyl-propionic acid ethyl ester 2-(3-Formyl-5-methoxy-phenoxy)-2-methyl-propionic acid ethyl ester 9.40 g (61.8 mmol) of 3-hydroxy-5-methoxy-benzaldehyde [Journal of Organic Chemistry (1985), 50(13), 2236-40], and 23.92 mL=31.33 g (160.6 mmol) of ethyl-bromoisobutyrate were dissolved in 130 mL acetonitrile; then, 25.62 g (185.4 mmol) of potassium carbonate were added and the reaction mixture stirred for 16 hours at 80° C. (reflux). It was then cooled down to ambient temperature and the solvent was evaporated. The residue was partitioned between water and ether and extracted twice with ether; the organic phases were washed with water, dried (MgSO₄), filtered and evaporated. The crude product was purified by flash chromatography (SiO₂, heptane/AcOEt) to finally give 16.4 g of the title compound as yellow oil. MS: 266 (M⁺).

2-{3-[1-(3,5-Diethoxy-4-fluoro-benzyl)-piperidin-4-ylcarbamoyl]-5-methoxy-phenoxy}-2-methyl-propionic acid ethyl ester In analogy to the procedure described in example 50k), 2-[3-methoxy-5-(piperidin-4-ylcarbamoyl)-phenoxy]-2-methyl-propionic acid ethyl ester [prepared by i) oxidation of 2-(3-formyl-5-methoxy-phenoxy)-2-methyl-propionic acid ethyl ester with sodium chlorite in analogy to example 60c) to give 3-(1-ethoxycarbonyl-1-methyl-ethoxy)-5-methoxy-benzoic acid; ii) subsequent condensation with 4-amino-piperidine-carboxylic acid tert-butyl ester, using acid activation with 2-chloro-4,6-dimethoxy-1,3,5-triazine in analogy to the procedure described in example 50 h) followed by Boc cleavage with TFA in analogy to the procedure described in example 50i)] was reacted with 3,5-diethoxy-4-fluoro-benzaldehyde (example 50 g), sodium cyanoborohydride, N-ethyl-diisopropylamine and acetic acid in ethanol at 50° C. to yield the title compound as colorless foam. MS: 561.6 (MH⁺).

Example 67

2-{3-[1-(3,5-Diethoxy-4-pyrrol-1-yl-benzyl)-piperidin-4-ylcarbamoyl]-5-methoxy-phenoxy}-2-methyl-propionic acid ethyl ester In analogy to the procedure described in example 50k), 2-[3-methoxy-5-(piperidin-4-ylcarbamoyl)-phenoxy]-2-methyl-propionic acid ethyl ester [example 66b)] was reacted with 3,5-diethoxy-4-pyrrol-1-yl-benzaldehyde (example 40b), sodium cyanoborohydride, N-ethyl-diisopropylamine and acetic acid in ethanol at 50° C. to yield the title compound yellow oil. MS: 608.4 (MH⁺).

Example 68

2-{3-[1-(3-Ethoxy-4-methoxy-benzyl)-piperidin-4-ylcarbamoyl]-5-methoxy-phenoxy}-2-methyl-propionic acid ethyl ester In analogy to the procedure described in example 50k), 2-[3-methoxy-5-(piperidin-4-ylcarbamoyl)-phenoxy]-2-methyl-propionic acid ethyl ester (example 66b) was reacted with 3-ethoxy-4-methoxybenzaldehyde, sodium cyanoborohydride, N-ethyl-diisopropylamine and acetic acid in ethanol at 50° C. to yield the title compound as off-white amorphous solid. MS: 529.3 (MH⁺).

Example 69

2-{3-[1-(3,5-Diethoxy-4-fluoro-benzyl)-piperidin-4-ylcarbamoyl]-5-methoxy-phenoxy}-2-methyl-propionic acid In analogy to the procedure described in example 53, 2-{3-[1-(3,5-diethoxy-4-fluoro-benzyl)-piperidin-4-ylcarbamoyl]-5-methoxy-phenoxy}-2-methyl-propionic acid ethyl ester (example 66b) was saponified to yield the title compound as colorless solid. MS: 533.4 (MH⁺).

Example 70

2-{3-[1-(3,5-Diethoxy-4-pyrrol-1-yl-benzyl)-piperidin-4-ylcarbamoyl]-5-methoxy-phenoxy}-2-methyl-propionic acid In analogy to the procedure described in example 53, 2-{3-[1-(3,5-diethoxy-4-pyrrol-1-yl-benzyl)-piperidin-4-ylcarbamoyl]-5-methoxy-phenoxy}-2-methyl-propionic acid ethyl ester (example 67) was saponified to yield the title compound as off-white solid. MS: 578.2 [(M−H)⁻].

Example 71

2-{3-[1-(3-Ethoxy-4-methoxy-benzyl)-piperidin-4-ylcarbamoyl]-5-methoxy-phenoxy}-2-methyl-propionic acid In analogy to the procedure described in example 53, 2-{3-[1-(3-ethoxy-4-methoxy-benzyl)-piperidin-4-ylcarbamoyl]-5-methoxy-phenoxy}-2-methyl-propionic acid ethyl ester (example 68) was saponified to yield the title compound as off-white solid. MS: 499.2 [(M−H)⁻].

Example 72

Methanesulfonic acid 3-[1-(3-ethoxy-4-methyl-benzyl)-piperidin-4-ylcarbamoyl]-phenyl ester 3-Methanesulfonyloxy-benzoic acid methyl ester To a solution of methyl 3-hydroxybenzoate (2.50 g, 16 mmol) in 33 ml of CH₂Cl₂ was added at 0° C. 1.2 eq. of methanesulfonyl chloride (1.53 ml) and 2 eq. of triethylamine (4.58 ml) and the mixture kept for another 3 h at ambient temperature. Pouring onto crashed ice/NH₄Cl, twofold extraction with AcOEt, washing with brine, drying over sodium sulfate, and evaporation of the solvents, followed by flash chromatography (SiO₂, hexane/AcOEt=6/4) left finally 3.81 g of the title compound as colorless oil.

MS (ISP): 231.1 [M+H]⁺, 248.1 [M+NH₄]⁺.

3-Methanesulfonyloxy-benzoic acid

The above prepared 3-methanesulfonyloxy-benzoic acid methyl ester (3.81 g, 16 mmol) was dissolved in 100 ml of THF/ethanol=1/1 and treated with 50 ml of aq. NaOH (1M, 3 eq.). The mixture was stirred for 2 h at ambient temperature and was then poured onto crashed ice/AcOEt/HCl dil.; the organic layer was washed with water, dried over sodium sulfate, and evaporated to dryness to leave 3.38 g of the title compound as white solid.

MS (ISN): 215.3 [M−H]−.

4-(3-Methanesulfonyloxy-benzoylamino)-piperidine-1-carboxylic acid tert-butyl ester The above prepared 3-methanesulfonyloxy-benzoic acid (0.400 g, 1.85 mmol) was condensed with 4-amino-1-BOC-piperidine (0.370 g, 1 eq.) in the presence of 1.1 eq. of (benzotriazol-1-yloxy)-tris-(dimethylamino)phosphonium hexafluorophosphate (0.899 g) and 1.2 eq. of N-ethyl-diisopropylamine (0.38 ml) in 9 ml of abs. THF during one night at ambient temperature. Pouring onto crashed ice/AcOEt, twofold extraction with AcOEt, washing with water, drying over sodium sulfate, and evaporation of the solvents, followed by flash chromatography ($SiO_2$, hexane/AcOEt=7/3), yielded 0.920 g of the title compound as white foam, contaminated with some reagent derived impurities, but sufficiently pure for the next steps.

Methanesulfonic acid 3-(piperidin-4-ylcarbamoyl)-phenyl ester

The above prepared 4-(3-methanesulfonyloxy-benzoylamino)-piperidine-1-carboxylic acid tert-butyl ester (0.920 g, 1.85 mmol) was dissolved in 9.5 ml of $CH_2Cl_2$ and treated with 2.4 ml of trifluoroacetic acid. After stirring for 4 h at ambient temperature, TLC indicated the absence of starting material. Evaporation of all volatiles left 1.47 g of the title compound as trifluoroacetate as off-white viscous oil.

MS (ISP): 299.3 [M+H]+.

Methanesulfonic acid 3-[1-(3-ethoxy-4-methyl-benzyl)-piperidin-4-ylcarbamoyl]-phenyl ester The above prepared methanesulfonic acid 3-(piperidin-4-ylcarbamoyl)-phenyl ester (0.120 g, 0.150 mmol) was dissolved in 1.9 ml of iPrOH and treated successively with 3-ethoxy-4-methyl-benzaldehyde (example 34, 0.025 g, 1 eq.), titanium tetra-isopropoxide (0.13 ml, 3 eq.), and NaCNBH$_3$ (0.019 g, 2 eq.). The reaction mixture was allowed to react over night and then poured directly onto a flash column ($SiO_2$). Eluting with AcOEt/5% NEt$_3$ delivered 0.030 g of the title compound as white solid.

MS (ISP): 447.0 [M+H]+.

Example 73

Methanesulfonic acid 3-[1-(4-chloro-3-ethoxy-benzyl)-piperidin-4-ylcarbamoyl]-phenyl ester The title compound was prepared in analogy to example 72, but using in the reductive amination step 4-chloro-3-ethoxy-benzaldehyde (example 1) instead of ethoxy-4-methyl-benzaldehyde, as white solid.

MS (ISP): 467.1 (M+H)+.

Example 74

Methanesulfonic acid 3-[1-(3,5-diethoxy-4-pyrrol-1-yl-benzyl)-piperidin-4-ylcarbamoyl]-phenyl ester The title compound was prepared in analogy to example 72, but using in the reductive amination step 3,5-diethoxy-4-pyrrol-1-yl-benzaldehyde (example 40b) instead of ethoxy-4-methyl-benzaldehyde, as light yellow solid,

MS (ISP): 542.2 (M+H)+.

Example 75

Methanesulfonic acid 3-[1-(2-ethoxy-4'-trifluoromethyl-biphenyl-4-ylmethyl)-piperidin-4-ylcarbamoyl]-phenyl ester This compound was prepared in analogy to example 72, but using in the reductive amination step 2-ethoxy-4'-trifluoromethyl-biphenyl-4-carbaldehyde instead of ethoxy-4-methyl-benzaldehyde, as white solid.

MS (ISP): 577.2 (M+H)+.

The necessary intermediate 2-ethoxy-4'-trifluoromethyl-biphenyl-4-carbaldehyde was prepared as follows:

2-Ethoxy-4'-trifluoromethyl-biphenyl-4-carboxylic acid ethyl ester

3-Ethoxy-4-iodo-benzoic acid ethyl ester (0.500 g, 1.56 mmol, CAS No. 741699-04-7) was dissolved under Ar in 12 ml of abs. DMF and treated successively with 4-(trifluoromethyl)phenyl boronic acid (0.356 g, 1.2 eq.), $K_3PO_4$ (0.564 g, 1.7 eq.), and Pd(PPh$_3$)$_4$ (0.054 g, 0.03 eq.). The mixture was allowed to react for 16 h at 80° C. Pouring onto crashed ice/NH$_4$Cl, twofold extraction with AcOEt, washing with brine, drying over sodium sulfate, and evaporation of the solvents, followed by flash chromatography (silica gel, hexane/AcOEt=95/5) afforded finally 0.515 g of the title compound as white solid.

MS (EI): 338.2 [M]+.

(2-Ethoxy-4'-trifluoromethyl-biphenyl-4-yl)-methanol

To the above synthesized 2-ethoxy-4'-trifluoromethyl-biphenyl-4-carboxylic acid ethyl ester (0.515 g, 1.52 mmol), dissolved in 6 ml of abs. THF, was added drop wise at −10° C. DIBAL-H solution in toluene (3.81 ml 1M, 2.5 eq.). After additional 60 Min. at ambient temperature, the reaction mixture was carefully poured onto crashed ice/dil. HCl-solution, twofold extracted with AcOEt, washed with water, dried over sodium sulfate, and evaporated to dryness. Thereby, 0.359 g of the title alcohol was isolated as white solid, sufficiently pure for the next step.

MS (EI): 296.1 [M]+.

2-Ethoxy-4'-trifluoromethyl-biphenyl-4-carbaldehyde

The above prepared (2-ethoxy-4'-trifluoromethyl-biphenyl-4-yl)-methanol (0.359 g, 1.21 mmol) was dissolved in 12 ml of dichloromethane and treated with MnO$_2$ (2.11 g, 20 eq.). After vigorous stirring for 8 h at ambient temperature, the reaction mixture was filtered over a pad of Celite, rinsed generously with dichloromethane, and evaporated to dryness to leave, after flash chromatography (silica gel, hexane/AcOEt=9/1) 0.372 g of the title aldehyde as yellow solid.

MS (EI): 294.2 [M]+.

Example 76

Methanesulfonic acid 3-{1-[4-fluoro-3-(2-fluoro-ethoxy)-benzyl]-piperidin-4-ylcarbamoyl}-phenyl ester The title compound was prepared in analogy to example 72, but using in the reductive amination step 4-fluoro-3-(2-fluoro-ethoxy)-benzaldehyde instead of ethoxy-4-methyl-benzaldehyde, as white solid.
MS (ISP): 469.1 (M+H)+.

The necessary intermediate 4-Fluoro-3-(2-fluoro-ethoxy)-benzaldehyde was prepared as described above in example 75 b)-c), but starting the whole reaction sequence with 4-fluoro-3-(2-fluoro-ethoxy)-benzoic acid 2-fluoro-ethyl ester instead of 2-ethoxy-4'-trifluoromethyl-biphenyl-4-carboxylic acid ethyl ester.

The former ester 4-Fluoro-3-(2-fluoro-ethoxy)-benzoic acid 2-fluoro-ethyl ester was prepared as follows Commercially available 4-fluoro-3-hydroxy-benzoic acid (1.19 g, 7.62 mmol) was dissolved in 15 ml of DMF, treated with 1-iodo-2-fluoroethane (4.641 g, 3.5 eq.) and potassium carbonate (2.634 g, 2.5 eq.) and stirred over night at 50° C. The reaction mixture was then poured onto crashed ice/AcOEt, the aqueous phase extracted again with AcOEt; the combined organic layers were washed with water, dried over sodium sulfate, and evaporated to dryness. Flash chromatography (SiO$_2$, hexane/AcOEt=7/3) of the residue yielded 1.88 g of the title compound as white solid.
MS (EI): 248.1 [M]+.

Example 77

Methanesulfonic acid 3-[1-(3-ethoxy-4-fluoro-benzyl)-piperidin-4-ylcarbamoyl]-phenyl ester The title compound was prepared in analogy to example 72, but using in the reductive amination step 3-ethoxy-4-fluoro-benzaldehyde (example 36) instead of ethoxy-4-methyl-benzaldehyde, as white solid.
MS (ISP): 451.1 (M+H)+.

Example 78

Methanesulfonic acid 3-[1-(2-ethoxy-4'-fluoro-biphenyl-4-ylmethyl)-piperidin-4-ylcarbamoyl]-phenyl ester The title compound was prepared in analogy to example 72, but using in the reductive amination step 2-ethoxy-4'-fluoro-biphenyl-4-carbaldehyde instead of ethoxy-4-methyl-benzaldehyde, as white crystals.
MS (ISP): 527.3 (M+H)+.

The necessary intermediate 2-Ethoxy-4'-fluoro-biphenyl-4-carbaldehyde was prepared as described in example 75a)-c), but using for the Suzuki—coupling 4-fluorophenyl boronic acid instead of 4-(trifluoromethyl)phenyl boronic acid, as white solid.
MS (ISP): 245.3 (M+H)+.

Example 79

6-Amino-N-[1-(2-ethoxy-4'-fluoro-biphenyl-4-ylmethyl)-piperidin-4-yl]-nicotinamide The title compound was prepared in analogy to example 72, but starting the whole reaction sequence with 6-aminonicotinic acid instead of 3-methanesulfonyloxy-benzoic acid and using in the reductive amination step 2-ethoxy-4'-fluoro-biphenyl-4-carbaldehyde instead of ethoxy-4-methyl-benzaldehyde, as white solid.
MS (ISP): 449.2 (M+H)+.

Example 80

6-Amino-N-[1-(3-ethoxy-4-fluoro-benzyl)-piperidin-4-yl]-nicotinamide

The title compound was prepared in analogy to example 79, but using in the reductive amination step 3-ethoxy-4-fluoro-benzaldehyde (example 36) instead of 2-ethoxy-4'-fluoro-biphenyl-4-carbaldehyde, as white crystals.
MS (ISP): 373.3 (M+H)+.

Example 81

N-[1-(3-Ethoxy-4-methyl-benzyl)-piperidin-4-yl]-3-methanesulfonyl-benzamide

The title compound was prepared in analogy to example 72, but starting the whole reaction sequence with 3-methylsulfonylbenzoic acid instead of 3-methanesulfonyloxy-benzoic acid, as white crystals.
MS (ISP): 431.4 (M+H)+.

Example 82

N-[1-(2-Ethoxy-4'-fluoro-biphenyl-4-ylmethyl)-piperidin-4-yl]-3-methanesulfonyl-benzamide The title compound was prepared in analogy to example 81, but using in the reductive amination step 2-ethoxy-4'-fluoro-biphenyl-4-carbaldehyde instead of ethoxy-4-methyl-benzaldehyde, as white crystals.
MS (ISP): 511.3 (M+H)+.

Example 83

N-[1-(3-Ethoxy-4-fluoro-benzyl)-piperidin-4-yl]-3-methanesulfonyl-benzamide

The title compound was prepared in analogy to example 81, but using in the reductive amination step 3-ethoxy-4-fluoro-benzaldehyde instead of ethoxy-4-methyl-benzaldehyde, as white crystals.
MS (ISP): 435.1 (M+H)+.

Example 84

6-Amino-N-[1-(3,5-diethoxy-4-fluoro-benzyl)-piperidin-4-yl]-nicotinamide

The title compound was prepared in analogy to example 80, but using in the reductive amination step 3,5-diethoxy-4-fluoro-benzaldehyde (example 50 g) instead of 3-ethoxy-4-fluoro-benzaldehyde, as off-white solid.
MS (ISP): 417.1 (M+H)+.

Example 85

6-Amino-N-[1-(3-ethoxy-4-methyl-benzyl)-piperidin-4-yl]-nicotinamide

The title compound was prepared in analogy to example 80, but using in the reductive amination step 3-ethoxy-4-methyl-benzaldehyde instead of 3-ethoxy-4-fluoro-benzaldehyde, as white crystals.
MS (ISP): 369.2 (M+H)$^+$.

Example 86

N-[1-(3,5-Diethoxy-4-fluoro-benzyl)-piperidin-4-yl]-5-methyl-nicotinamide

The title compound was prepared in analogy to example 84, but starting the whole reaction sequence with 5-methylnicotinic acid instead of 6-aminonicotinic acid, as white crystals.
MS (ISP): 416.1 (M+H)$^+$.

Example 87

6-Amino-N-{1-[4-fluoro-3-(2-fluoro-ethoxy)-benzyl]-piperidin-4-yl}-nicotinamide

The title compound was prepared in analogy to example 85, but using in the reductive amination step 4-fluoro-3-(2-fluoro-ethoxy)-benzaldehyde (example 76) instead of 3-ethoxy-4-methyl-benzaldehyde, as white powder.
MS (ISP): 391.1 (M+H)$^+$.

Example 88

N-[1-(2-Ethoxy-4'-fluoro-biphenyl-4-ylmethyl)-piperidin-4-yl]-5-methyl-nicotinamide The title compound was prepared in analogy to example 86, but using in the reductive amination step 2-ethoxy-4'-fluoro-biphenyl-4-carbaldehyde instead of 3,5-diethoxy-4-fluoro-benzaldehyde, as white crystals.
MS (ISP): 448.2 (M+H)$^+$.

Example 89

6-Amino-N-[1-(2-ethoxy-4'-trifluoromethyl-biphenyl-4-ylmethyl)-piperidin-4-yl]-nicotinamide The title compound was prepared in analogy to example 79, but using in the reductive amination step 2-ethoxy-4'-trifluoromethyl-biphenyl-4-carbaldehyde instead of 2-ethoxy-4'-fluoro-biphenyl-4-carbaldehyde, as white crystals.
MS (ISP): 499.2 (M+H)$^+$.

Example 90

N-[1-(2-Ethoxy-biphenyl-4-ylmethyl)-piperidin-4-yl]-5-methyl-nicotinamide

The title compound was prepared in analogy to example 88, but using in the reductive amination step 2-ethoxy-biphenyl-4-carbaldehyde instead of 2-ethoxy-4'-fluoro-biphenyl-4-carbaldehyde, as white solid.
MS (ISP): 430.4 (M+H)$^+$.

The necessary intermediate 2-Ethoxy-biphenyl-4-carbaldehyde was prepared as described in example 75a)-c), but using for the Suzuki—coupling phenyl boronic acid instead of 4-(trifluoromethyl)phenyl boronic acid, as yellow viscous oil.
MS (EI): 226.2 (M)$^+$.

Example 91

N-[1-(2-Ethoxy-4'-trifluoromethyl-biphenyl-4-ylmethyl)-piperidin-4-yl]-5-methyl-nicotinamide The title compound was prepared in analogy to example 90, but using in the reductive amination step 2-ethoxy-4'-trifluoromethyl-biphenyl-4-carbaldehyde instead of 2-ethoxy-biphenyl-4-carbaldehyde, as white crystals.
MS (ISP): 498.1 (M+H)$^+$.

Example 92

6-Amino-N-[1-(2-ethoxy-biphenyl-4-ylmethyl)-piperidin-4-yl]-nicotinamide

The title compound was prepared in analogy to example 79, but using in the reductive amination step 2-ethoxy-biphenyl-4-carbaldehyde instead of 2-ethoxy-4'-fluoro-biphenyl-4-carbaldehyde, as white crystals.
MS (ISP): 431.2 (M+H)$^+$.

Example 93

6-Amino-N-{1-[3-(2-fluoro-ethoxy)-4-methyl-benzyl]-piperidin-4-yl}-nicotinamide

The title compound was prepared in analogy to example 87, but using in the reductive amination step 3-(2-fluoro-ethoxy)-4-methyl-benzaldehyde instead of 4-fluoro-3-(2-fluoro-ethoxy)-benzaldehyde, as white crystals.
MS (ISP): 387.2 (M+H)$^+$.

The necessary intermediate 3-(2-Fluoro-ethoxy)-4-methyl-benzaldehyde was prepared as described in example 76 and 75b)-c), but starting the reaction sequence with commercially available 3-hydroxy-4-methylbenzoic acid, as white crystals.
MS (EI): 182.0 (M)$^+$.

Example 94

6-Amino-N-[1-(2-benzyloxy-6-ethoxy-4'-fluoro-biphenyl-4-ylmethyl)-2-piperidin-4-yl]-nicotinamide This compound was prepared in analogy to example 79, but using in the reductive amination step 2-benzyloxy-6-ethoxy-4'-fluoro-biphenyl-4-carbaldehyde instead of 2-ethoxy-4'-fluoro-biphenyl-4-carbaldehyde, as light yellow crystals.
MS (ISP): 555.3 (M+H)$^+$.

The necessary intermediate 2-Benzyloxy-6-ethoxy-4'-fluoro-biphenyl-4-carbaldehyde was prepared as follows:

3-Benzyloxy-5-ethoxy-4-iodo-benzaldehyde (0.100 g, 0.262 mmol, CAS NO. 338455-15-5) was dissolved under Ar in 1.5 ml of abs. DMF and treated successively with 4-fluorophenyl boronic acid (0.046 g, 1.25 eq.), $K_3PO_4$ (0.100 g, 1.8 eq.), and Pd(PPh$_3$)$_4$ (0.060 g, 0.2 eq.). The mixture was allowed to react for 16 h at 90-95° C. Pouring onto crashed ice, twofold extraction with AcOEt, washing with water, drying over sodium sulfate, and evaporation of the solvents, followed by flash chromatography (silica gel, hexane/AcOEt=8/2) afforded 0.089 g of the title compound as white solid.

MS (EI): 350.1 [M]+.

Example 95

6-Amino-N-[1-(3,5-diisopropoxy-benzyl)-piperidin-4-yl]-nicotinamide

The title compound was prepared in analogy to example 79, but using in the reductive amination step 3,5-diisopropoxy-benzaldehyde (CAS NO. 94169-64-9) instead of 2-ethoxy-4'-fluoro-biphenyl-4-carbaldehyde, as white foam.

MS (ISP): 427.3 (M+H)+.

Example 96

Methanesulfonic acid 3-[1-(4-ethoxy-1H-indol-6-ylmethyl)-piperidin-4-ylcarbamoyl]-phenyl ester This compound was prepared in analogy to example 72, but using in the reductive amination step 4-ethoxy-1H-indole-6-carbaldehyde instead of 3-ethoxy-4-methyl-benzaldehyd, as white foam.

MS (ISP): 472.0 (M+H)+.

The necessary intermediate 4-Ethoxy-1H-indole-6-carbaldehyde was synthesized following the procedure described in J. Org. Chem. 2004, 69, 6945 and ensuing DIBAL-H—reduction and MnO$_2$—oxidation of the resultant 4-ethoxy-1H-indole-6-carboxylic acid methyl ester, as yellow solid.

MS (ISP): 190.3 (M+H)+.

Example 97

N-[1-(4-Ethoxy-1H-indol-6-ylmethyl)-piperidin-4-yl]-5-methyl-nicotinamide

The title compound was prepared in analogy to example 96, but starting the whole reaction sequence with 5-methylnicotinic acid instead of 3-methanesulfonyloxy-benzoic acid, as yellow foam.

MS (ISP): 393.0 (M+H)+.

Example 98

N-[1-(3,5-Diisopropoxy-benzyl)-piperidin-4-yl]-5-methyl-nicotinamide

The title compound was prepared in analogy to example 95, but starting the whole reaction sequence with 5-methylnicotinic acid instead of 6-aminonicotinic acid, as colorless oil.

MS (ISP): 426.2 (M+H)+.

Example 99

N-[1-(3,5-Diisopropoxy-benzyl)-piperidin-4-yl]-3-methanesulfonyl-benzamide

The title compound was prepared in analogy to example 95, but starting the whole reaction sequence with 3-methylsulfonylbenzoic acid instead of 6-aminonicotinic acid, as white foam.

MS (ISP): 489.4 (M+H)+.

Example 100

N-[1-(4-Ethoxy-1H-indol-6-ylmethyl)-piperidin-4-yl]-3-methanesulfonyl-benzamide

The title compound was prepared in analogy to example 96, but starting the whole reaction sequence with 3-methylsulfonylbenzoic acid instead of 3-methanesulfonyloxy-benzoic acid, as light red solid.

MS (ISP): 456.3 (M+H)+.

Example 101

Methanesulfonic acid 3-[1-(3,5-diisopropoxy-benzyl)-piperidin-4-ylcarbamoyl]-phenyl ester The title compound was prepared in analogy to example 99, but starting the whole reaction sequence with 3-methanesulfonyloxy-benzoic acid instead of 3-methylsulfonylbenzoic acid, as colorless oil.

MS (ISP): 505.2 (M+H)+.

Example 102

Methanesulfonic acid 3-[1-(2,6-diethoxy-4'-fluoro-biphenyl-4-ylmethyl)-piperidin-4-ylcarbamoyl]-phenyl ester The title compound was prepared in analogy to example 101, but using in the reductive amination step 2,6-diethoxy-4'-fluoro-biphenyl-4-carbaldehyde instead of 3,5-diisopropoxy-benzaldehyde, as white solid.

MS (ISP): 571.3 (M+H)+.

The necessary intermediate 2,6-Diethoxy-4'-fluoro-biphenyl-4-carbaldehyde was prepared as described in example 94, but reacting in the Suzuki coupling 3,5-diethoxy-4-iodo-benzaldehyde (CAS NO. 338454-05-0) instead of 3-benzyloxy-5-ethoxy-4-iodo-benzaldehyde with 4-fluorophenyl boronic acid, as light yellow solid.

MS (EI): 288.2 [M]+.

Example 103

N-[1-(3,5-Diethoxy-4-fluoro-benzyl)-piperidin-4-yl]-6-methylamino-nicotinamide

This compound was prepared as described in example 84, but using for the reductive amination step 6-methylamino-N-piperidin-4-yl-nicotinamide as amine component instead of 6-amino-N-piperidin-4-yl-nicotinamide, as white solid.

MS (ISP): 431.1 (M+H)+.

The former was prepared as follows:

4-[(6-tert-Butoxncarbonylamino-pyridine-3-carbonyl)-amino]-piperidine-1-carboxylic acid tert-butyl ester 6-Aminonicotinic acid was condensed with commercially available 4-aminol-BOC-piperidine according to standard procedures ((benzotriazol-1-yloxy)-tris-(dimethylamino)phosphonium hexafluorophosphate/N-ethyl-diisopropylamine in abs. THF). 1.40 g thereof (4.37 mmol) was dissolved in abs. THF (22 ml) and treated with 2.2 eq. of sodium hexamethyldisilazide-solution (1M in THF) and 2.3 eq. of BOC$_2$O (2.193 g). The mixture was kept over night at 40° C. Pouring onto crashed ice/NH$_4$Cl, twofold extraction with AcOEt, washing with water and brine, drying over magnesium sulfate, and evaporation of the solvents, followed by flash chromatography (silica gel, hexane/AcOEt=0.1/1) yielded 1.37 g of the tri-BOC-intermediate which was selectively hydrolyzed as follows:

It was dissolved in MeOH (25 ml) and treated with K$_2$CO$_3$ (1.091 g, 3 eq.). After refluxing for 4 h, TLC indicated the absence of starting material. Pouring onto crashed ice/NH$_4$Cl, twofold extraction with AcOEt, washing with water and brine, drying over magnesium sulfate, and evaporation of the solvents, followed by direct crystallization from hexane/AcOEt delivered 0.723 g of the title compound as white crystals.

MS (ISP): 421.3 [M+H]+.

4-{[6-(tert-Butoxycarbonyl-methyl-amino)-pyridine-3-carbonyl]-amino}-piperidine-1-carboxylic acid tert-butyl ester The above prepared 4-[(6-tert-butoxycarbonylamino-pyridine-3-carbonyl)-amino]-piperidine-1-carboxylic acid tert-butyl ester (0.720 g, 1.71 mmol) was dissolved in 30 ml of abs. THF and treated at 0° C. with sodium hexamethyldisilazide-solution (1M in THF, 1.05 eq.) and, after 15 Min., 50 eq. of methyl iodide (5.33 ml). The mixture was allowed to react for six days! Pouring onto crashed ice/$NH_4Cl$, twofold extraction with AcOEt, washing with water and brine, drying over magnesium sulfate, and evaporation of the solvents, followed by flash chromatography (silica gel, hexane/AcOEt=55/45) yielded eventually 0.497 g of the title compound as white foam.
MS (ISP): 435.1 [M+H]$^+$.

6-Methylamino-N-piperidin-4-yl-nicotinamide

The above prepared 4-{[6-(tert-butoxycarbonyl-methyl-amino)-pyridine-3-carbonyl]-amino}-piperidine-1-carboxylic acid tert-butyl ester (0.495 g, 1.14 mmol) was dissolved in 14 ml of $CH_2Cl_2$ and treated with 2.8 ml of trifluoroacetic acid. After stirring for 3 h at ambient temperature, TLC indicated the absence of starting material. Evaporation of all volatiles left 0.704 g of the title compound as trifluoroacetate as light brown amorphous solid.
MS (ISP): 235.3 [M+H]$^+$.

Example 104

N-[1-(3-Ethoxy-4-pyridin-3-yl-benzyl)-piperidin-4-yl]-3-methanesulfonyl-benzamide The title compound was prepared in analogy to example 82, but using in the reductive amination step 3-ethoxy-4-pyridin-3-yl-benzaldehyde instead of 2-ethoxy-4'-fluoro-biphenyl-4-carbaldehyde, as white solid.
MS (ISP): 494.2 (M+H)$^+$.
The necessary intermediate 3-Ethoxy-4-pyridin-3-yl-benzaldehyde was prepared as described in example 75a)-c), but using for the Suzuki—coupling 3-pyridylboronic acid instead of 4-(trifluoromethyl)phenyl boronic acid, as white crystals.
MS (EI): 227.2 (M)$^+$.

Example 105

N-[1-(3-Ethoxy-4-pyridin-3-yl-benzyl)-piperidin-4-yl]-5-methyl-nicotinamide The title compound was prepared in analogy to example 104, but starting the whole reaction sequence with 5-methylnicotinic acid instead of 3-methylsulfonylbenzoic acid, as light yellow gum.
MS (ISP): 431.3 (M+H)$^+$.

Example 106

Methanesulfonic acid 3-[1-(3-ethoxy-pyridin-3-yl-benzyl)-piperidin-4-ylcarbamoyl]-phenyl ester The title compound was prepared in analogy to example 104, but starting the whole reaction sequence with 3-methanesulfonyloxy-benzoic acid instead of 3-methyl-sulfonyl-benzoic acid, as colorless gum.
MS (ISP): 410.3 (M+H)$^+$.

Example 107

N-[1-(2-Ethoxy-4'-fluoro-biphenyl-4-ylmethyl)-piperidin-4-yl]-6-methylamino-nicotinamide The title compound was prepared in analogy to example 103, but using in the reductive amination step 2-ethoxy-4'-fluoro-biphenyl-4-carbaldehyde instead of 3,5-diethoxy-4-fluoro-benzaldehyde, as white solid.
MS (ISP): 463.5 (M+H)$^+$.

Example 108

6-Amino-N-[1-(2-ethoxy-4'-fluoro-biphenyl-4-ylmethyl)-piperidin-4-yl]-5-methyl-nicotinamide The title compound was prepared in analogy to example 79, but starting the whole reaction sequence with 6-amino-5-methyl-nicotinic acid (CAS No. 167626-78-0) instead of 6-amino-nicotinic acid, as of white solid.
MS (ISP): 463.2 (M+H)$^+$.

Example 109

6-Amino-N-[1-(3-ethoxy-4-methyl-benzyl)-piperidin-4-yl]-5-methyl-nicotinamide The title compound was prepared in analogy to example 108, but using in the reductive amination step 3-ethoxy-4-methyl-benzaldehyde instead of 2-ethoxy-4'-fluoro-biphenyl-4-carbaldehyde, as off-white solid.
MS (ISP): 383.2 (M+H)$^+$.

Example 110

6-Amino-N-[1-(3-ethoxy-4-pyridin-3-yl-benzyl)-piperidin-4-yl]-nicotinamide

The title compound was prepared in analogy to example 79, but using in the reductive amination step 3-ethoxy-4-pyridin-3-yl-benzaldehyde (example 104) instead of 2-ethoxy-4'-fluoro-biphenyl-4-carbaldehyde, as white crystals.
MS (ISP): 432.2 (M+H)$^+$.

Example 111

N-[1-(3-Ethoxy-4-pyridin-4-yl-benzyl)-piperidin-4-yl]-5-methyl-nicotinamide The title compound was prepared in analogy to example 105, but using in the reductive amination step 3-ethoxy-4-pyridin-4-yl-benzaldehyde instead of 3-ethoxy-4-pyridin-3-yl-benzaldehyde, as off-white crystals.
MS (ISP): 431.3 (M+H)$^+$.
The necessary intermediate 3-Ethoxy-4-pyridin-4-yl-benzaldehyde was prepared as described in example 75a)-c), but using for the Suzuki—coupling 4-pyridylboronic acid instead of 4-(trifluoromethyl)phenyl boronic acid, as colorless crystals.
MS (EI): 227.1 (M)$^+$.

Example 112

N-[1-(3-Ethoxy-4-pyridin-4-yl-benzyl)-piperidin-4-yl]-3-methanesulfonyl-benzamide The title compound was prepared in analogy to example 111, but starting the whole reaction sequence with 3-methylsulfonylbenzoic acid instead of 5-methylnicotinic acid, as white crystals.
MS (ISP): 494.2 (M+H)$^+$.

Example 113

Methanesulfonic acid 3-[1-(3-ethoxy-4-pyridin-4-yl-benzyl)-piperidin-4-ylcarbamoyl]-phenyl ester The title compound was prepared in analogy to example 111, but starting the whole reaction sequence with 3-methanesulfonyloxy-benzoic acid instead of 5-methylnicotinic acid, as white solid.
MS (ISP): 510.4 (M+H)$^+$.

Example 114

6-Amino-N-[1-(4-chloro-3-ethoxy-benzyl)-piperidin-4-yl]-5-methyl-nicotinamide

The title compound was prepared in analogy to example 108, but using in the reductive amination step 4-chloro-3-ethoxy-benzaldehyde instead of 2-ethoxy-4'-fluoro-biphenyl-4-carbaldehyde, as white solid.
MS (ISP): 403.4 (M+H)$^+$.

Example 115

6-Amino-N-[1-(3,5-diethoxy-4-fluoro-benzyl)-piperidin-4-yl]-5-methyl-nicotinamide The title compound was prepared in analogy to example 108, but using in the reductive amination step 3,5-diethoxy-4-fluoro-benzaldehyde instead of 2-ethoxy-4'-fluoro-biphenyl-4-carbaldehyde, as light yellow solid.
MS (ISP): 431.3 (M+H)$^+$.

Example 116

6-Amino-N-[1-(2-ethoxy-4'-trifluoromethyl-biphenyl-4-ylmethyl)-piperidin-4-yl]-5-methyl-nicotinamide The title compound was prepared in analogy to example 108, but using in the reductive amination step 2-ethoxy-4'-trifluoromethyl-biphenyl-4-carbaldehyde instead of 2-ethoxy-4'-fluoro-biphenyl-4-carbaldehyde, as off-white solid.
MS (ISP): 513.4 (M+H)$^+$.

Example 117

6-Amino-N-[1-(3-ethoxy-4-pyridin-4-yl-benzyl)-piperidin-4-yl]-nicotinamide

The title compound was prepared in analogy to example 79, but using in the reductive amination step 3-ethoxy-4-pyridin-4-yl-benzaldehyde instead of 2-ethoxy-4'-fluoro-biphenyl-4-carbaldehyde, as off-white crystals.
MS (ISP): 432.2 (M+H)$^+$.

Example 118

N-[1-(4-Chloro-3-ethoxy-benzyl)-piperidin-4-yl]-6-methylamino-nicotinamide

The title compound was prepared in analogy to example 103, but using in the reductive amination step 4-chloro-3-ethoxy-benzaldehyde instead of 3,5-diethoxy-4-fluoro-benzaldehyde, as white crystals.
MS (ISP): 403.3 (M+H)$^+$.

Example 119

N-[1-(3-Ethoxy-4-methyl-benzyl)-piperidin-4-yl]-6-methylamino-nicotinamide

The title compound was prepared in analogy to example 103, but using in the reductive amination step 3-ethoxy-4-methyl-benzaldehyde instead of 3,5-diethoxy-4-fluoro-benzaldehyde, as white crystals.
MS (ISP): 383.4 (M+H)$^+$.

Example 120

N-[1-(3-Ethoxy-4-pyridin-3-yl-benzyl)-piperidin-4-yl]-6-methylamino-nicotinamide The title compound was prepared in analogy to example 103, but using in the reductive amination step 3-ethoxy-4-pyridin-3-yl-benzaldehyde instead of 3,5-diethoxy-4-fluoro-benzaldehyde, as off-white crystals.
MS (ISP): 446.1 (M+H)$^+$.

Example 121

N-[1-(3,5-Diethoxy-4-fluoro-benzyl)-piperidin-4-yl]-5-methyl-6-methylamino-nicotinamide The title compound was prepared in analogy to example 84, but starting the whole reaction sequence with 5-methyl-6-methylamino-nicotinic acid instead of 6-amino-nicotinic acid, as light brown gum.
MS (ISP): 445.2 (M+H)$^+$.

The necessary starting material was prepared as follows:

5-Methyl-6-methylamino-nicotinonitrile

6-Amino-5-methyl-nicotinonitrile (0.250 g, 1.88 mmol) was dissolved in 2.5 ml of abs. THF and treated at 0° C. with sodium hexamethyldisilazide-solution (1M in THF, 2.07 ml, 1.1 eq.) and, after 5 Min., 3 eq. of methyl iodide (0.35 ml). The mixture was allowed to react for 3 h at ambient temperature. Pouring onto crashed ice/NH$_4$Cl, twofold extraction with AcOEt, washing with water, drying over sodium sulfate, and evaporation of the solvents, followed by flash chromatography (silica gel, hexane/AcOEt=6/4) produced 0.225 g of the title compound as off-white solid.
MS (ISP): 148.3 [M+H]$^+$.

5-Methyl-6-methylamino-nicotinic acid

The above prepared 5-methyl-6-methylamino-nicotinonitrile (0.311 g, 2.11 mmol) was dissolved in 10.6 ml of THF/ethanol=1/1 and treated with 0.676 g of NaOH pellets (8 eq.). The mixture was refluxed over night, cooled to room temperature, and neutralized with NH$_4$Cl. Ten times extraction with AcOEt, drying of the combined organic layers over sodium sulfate, and evaporation left 0.159 g of the title acid as reddish solid.

Example 122

N-[1-(3,5-Diisopropoxy-benzyl)-piperidin-4-yl]-5-methyl-6-methylamino-nicotinamide The title compound was prepared in analogy to example 121, but using in the reductive amination step 3,5-diisopropoxy-benzaldehyde (CAS No. 94169-64-9) instead of 3,5-diethoxy-4-fluoro-benzaldehyde, as colorless gum.
MS (ISP): 455.5 (M+H)+.

Example 123

N-[1-(2-Ethoxy-4'-fluoro-biphenyl-4-ylmethyl)-piperidin-4-yl]-5-methyl-6-methylamino-nicotinamide The title compound was prepared in analogy to example 121, but using in the reductive amination step 2-ethoxy-4'-fluoro-biphenyl-4-carbaldehyde instead of 3,5-diethoxy-4-fluoro-benzaldehyde, as white solid.
MS (ISP): 477.2 (M+H)+.

Example 124

N-[1-(3-Ethoxy-4-imidazol-1-yl-benzyl)-piperidin-4-yl]-5-methyl-nicotinamide

This compound was prepared in analogy to example 105, but using in the reductive amination step 3-ethoxy-4-imidazol-1-yl-benzaldehyde instead of 3-ethoxy-4-pyridin-3-yl-benzaldehyde, as white crystals.
MS (ISP): 420.2 (M+H)+.
The necessary aldehyde was prepared as follows:

3-Ethoxy-4-imidazol-1-yl-benzaldehyde

3-Ethoxy-4-fluoro-benzaldehyde (0.081 g, 0.482 mmol) was dissolved in 1 ml of DMSO and treated with potassium carbonate (0.166 g, 2.5 eq.) and imidazole (0.066 g, 2 eq.), and the mixture was allowed to react under a balloon of argon for 2 h at 105° C. Pouring onto crashed ice/NH$_4$Cl, twofold extraction with AcOEt, washing with water, drying over sodium sulfate, and evaporation of the solvents, followed by flash chromatography (silica gel, AcOEt) produced 0.087 g of the title compound as off-white crystals.
MS (ISP): 217.4 [M+H]+.

Example 125

N-[1-(3,5-Diethoxy-4-imidazol-1-yl-benzyl)-piperidin-4-yl]-5-methyl-nicotinamide The title compound was prepared in analogy to example 124, but using in the reductive amination step 3,5-diethoxy-4-imidazol-1-yl-benzaldehyde instead of 3-ethoxy-4-imidazol-1-yl-benzaldehyde, as white crystals.
MS (ISP): 464.5 (M+H)+.
The necessary aldehyde 3,5-Diethoxy-4-imidazol-1-yl-benzaldehyde was prepared by nucleophilic aromatic substitution of 3,5-diethoxy-4-fluoro-benzaldehyde with imidazole as described in example 124 as white crystals.
MS (ISP): 261.0 (M+H)+.

Example 126

N-[1-(3,5-Diisopropoxy-benzyl)-piperidin-4-yl]-2,6-dimethyl-terephthalamic acid 4-(4-tert-Butoxycarbonyl-3,5-dimethyl-benzoylamino)-piperidine-1-carboxylic acid tert-butyl ester 1.48 g (7.1 mMol) of 4-amino-piperidine-carboxylic acid tert-butyl ester was suspended in 45 mL of MeCl$_2$ at rt under Ar; then, 1.50 g (6.75 mmol) of 2,6-dimethyl-terephthalic acid mono-tert-butyl ester [PCT Int. Appl. (2000) WO 2000/066558 A1], 1.58 g (1.20 eq.) of N-(3-dimethylaminopropyl)-N'-ethyl-carbodiimide hydrochloride and 1.09 g (1.30 eq.) of N,N-dimethyl-4-aminopyridine were added. The reaction mixture became a clear solution after stirring for 1 h at rt. After 3 hours, the solution was evaporated i.V. and the residue was purified by chromatography (silicagel, eluent:gradient of MeCl$_2$/MeOH) to yield 1.68 g of the title compound as colorless solid. MS: 433.3 (MH+).

N-[1-(3,5-Diisopropoxy-benzyl)-piperidin-4-yl]-2,6-dimethyl-terephthalamic acid

In analogy to the procedure described in example 50k), 2,6-dimethyl-N-piperidin-4-yl-terephthalamic acid [prepared from 4-(4-tert-butoxycarbonyl-3,5-dimethyl-benzoylamino)-piperidine-1-carboxylic acid tert-butyl ester and trifluoroacetic acid in dichloromethane in analogy to the procedure described in example 50i)] was reacted with 3,5-diisopropoxy-benzaldehyde [prepared from 3,5-dihydroxy-benzaldehyde and 2-bromopropane, potassium carbonate in DMF at 60° C. in analogy to the procedure described in example 50e)], sodium cyanoborohydride, N-ethyl-diisopropylamine and acetic acid in ethanol at 50° C. to yield the title compound as light yellow solid. MS: 483.3 (MH+).

Example 127

N-[1-(3,5-Diethoxy-4-pyrrol-1-yl-benzyl)-piperidin-4-yl]-2,6-dimethyl-terephthalamic acid In analogy to the procedure described in example 50k), 2,6-dimethyl-N-piperidin-4-yl-terephthalamic acid (example 126b) was reacted with 3,5-diethoxy-4-pyrrol-1-yl-benzaldehyde (example 40b), sodium cyanoborohydride, N-ethyl-diisopropylamine and acetic acid in ethanol at 50° C. to yield the title compound as light yellow solid. MS: 520.3 (MH+).

Example 128

N-[1-(3,5-Diethoxy-4-fluoro-benzyl)-piperidin-4-yl]-2,6-dimethyl-terephthalamic acid In analogy to the procedure described in example 50k), 2,6-dimethyl-N-piperidin-4-yl-terephthalamic acid (example 126b) was reacted with 3,5-diethoxy-4-fluoro-benzaldehyde (example 50 g), sodium cyanoborohydride, N-ethyl-diisopropylamine and acetic acid in ethanol at 50° C. to yield the title compound as colorless solid. MS: 472.9 (MH+).

Example 129

2-{4-[1-(3,5-Diethoxy-4-[1,2,4]triazol-1-yl-benzyl)-piperidin-4-ylcarbamoyl]-phenyl}-2-methyl-propionic acid methyl ester 3,5-Diethoxy-4-[1,2,4]triazol-1-yl-benzaldehyde 5.00 g (23.6 mMol) of 3,5-diethoxy-4-fluoro-benzaldehyde (example 50 g), 3.25 g (=2.0 eq.) of 1,2,4-triazole and 6.51 g (=2.0 eq.) of potassium carbonate was dissolved under argon in 50 mL of DMSO; the reaction mixture was stirred for 1 hour at 110° C. Then, it was cooled down to ambient temperature, poured into crashed ice and extracted twice with ethyl acetate. The organic phases were washed with water, dried over MgSO$_4$, filtered and evaporated i.V. The crude product was purified by chromatography (silicagel, eluent:

gradient of n-heptane/ethyl acetate) to yield 5.28 g of the title compound as colorless solid. MS: 261.9 (MH$^+$).

2-{4-[1-(3,5-Diethoxy-4-[1,2,4]triazol-1-yl-benzyl)-piperidin-4-ylcarbamoyl]-phenyl}-2-methyl-propionic acid methyl ester In analogy to the procedure described in example 50k), 2-methyl-2-[4-(piperidin-4-ylcarbamoyl)-phenyl]-propionic acid methyl ester (example 60e) was reacted with 3,5-diethoxy-4-[1,2,4]triazol-1-yl-benzaldehyde, sodium cyanoborohydride, N-ethyl-diisopropylamine and acetic acid in ethanol at 50° C. to yield the title compound as colorless oil. MS: 550.2 (MH$^+$).

Example 130

2-{4-[1-(3,5-Diethoxy-4-[1,2,4]triazol-1-yl-benzyl)-piperidin-4-ylcarbamoyl]-phenyl}-2-methyl-propionic acid In analogy to the procedure described in example 53, 2-{4-[1-(3,5-diethoxy-4-[1,2,4]triazol-1-yl-benzyl)-piperidin-4-ylcarbamoyl]-phenyl}-2-methyl-propionic acid methyl ester (example 129b) was saponified to yield the title compound as colorless solid. MS: 534.4 [(M–H)$^-$].

Example 131

N-[1-(3,5-Diisopropoxy-benzyl)-piperidin-4-yl]-6-methylamino-nicotinamide

The compound was prepared in analogy to example 103, but using in the reductive amination step 3,5-diisopropoxy-benzaldehyde (CAS NO. 94169-64-9) instead of 3,5-diethoxy-4-fluoro-benzaldehyde, as white crystals.
MS (ISP): 441.3 (M+H)$^+$.

Example 132

N-[1-(3,5-Diethoxy-4-fluoro-benzyl)-piperidin-4-yl]-6-dimethylamino-5-methyl-nicotinamide The title compound was prepared in analogy to example 121, but starting the reaction sequence with 6-dimethylamino-5-methyl-nicotinic acid instead of 5-methyl-6-methylamino-nicotinic acid. The former was prepared as follows:

6-Dimethylamino-5-methyl-nicotinonitrile

5-Methyl-6-methylamino-nicotinonitrile (example 121, 0.345 g, 2.34 mmol) was dissolved in 3.2 ml of abs. THF and treated at 0° C. with sodium hexamethyldisilazide-solution (1M in THF, 7.03 ml, 3.0 eq.) and, after 5 Min., 4 eq. of methyl iodide (0.58 ml). The mixture was allowed to react for 1 h at room temperature. Pouring onto crashed ice/NH$_4$Cl, twofold extraction with AcOEt, washing with water, drying over sodium sulfate, and evaporation of the solvents, followed by flash chromatography (silica gel, hexane/AcOEt=7/3) yielded 0.330 g of the title compound as off-white solid.
MS (ISP): 162.3 [M+H]$^+$.

6-Dimethylamino-5-methyl-nicotinic acid

The above prepared 6-dimethylamino-5-methyl-nicotinonitrile (0.435 g, 2.70 mmol) was dissolved in 13.6 ml of THF/ethanol=1/1 and treated with 6.75 ml of 2N NaOH (5 eq.). The mixture was refluxed for 30 h; aliquots were taken from time to time and analyzed by MS to follow the disappearance of the amide intermediate. After cooling down to room temperature, the pH was adjusted with HCl to 3. Careful evaporation of the solvents and drying under HV left 1.45 g of the title acid as white solid, contaminated with NaCl, which was used as such for the next step.
MS (ISP): 181.1 [M+H]$^+$.

Example 133

N-[1-(4-Chloro-3-ethoxy-benzyl)-piperidin-4-yl]-6-dimethylamino-5-methyl-nicotinamide The title compound was prepared in analogy to example 132, but using in the reductive amination step 4-chloro-3-ethoxy-benzaldehyde instead of 3,5-diethoxy-4-fluoro-benzaldehyde, as colorless oil.
MS (ISP): 431.3 (M+H)$^+$.

Example 134

N-[1-(3,5-Diisopropoxy-benzyl)-piperidin-4-yl]-6-dimethylamino-5-methyl-nicotinamide The title compound was prepared in analogy to example 132, but using in the reductive amination step 3,5-diisopropoxy-benzaldehyde (CAS NO. 94169-64-9) instead of 3,5-diethoxy-4-fluoro-benzaldehyde, as colorless oil.
MS (ISP): 469.3 (M+H)$^+$.

Example 135

6-Dimethylamino-N-[1-(3-ethoxy-4-methyl-benzyl)-piperidin-4-yl]-5-methyl-nicotinamide The title compound was prepared in analogy to example 132, but using in the reductive amination step 3-ethoxy-4-methyl-benzaldehyde instead of 3,5-diethoxy-4-fluoro-benzaldehyde, as colorless oil.
MS (ISP): 411.2 (M+H)$^+$.

Example 136

6-Dimethylamino-N-[1-(2-ethoxy-4'-fluoro-biphenyl-4-ylmethyl)-piperidin-4-yl]-5-methyl-nicotinamide The title compound was prepared in analogy to example 132, but using in the reductive amination step 2-ethoxy-4'-fluoro-biphenyl-4-carbaldehyde instead of 3,5-diethoxy-4-fluoro-benzaldehyde, as white solid.
MS (ISP): 491.3 (M+H)$^+$.

Example 137

N-[1-(3-Ethoxy-4-imidazol-1-yl-benzyl)-piperidin-4-yl]-3-methanesulfonyl-benzamide The title compound was prepared in analogy to example 124, but starting the whole reaction sequence with 3-methylsulfonylbenzoic acid instead of 5-methylnicotinic acid, as light yellow gum.
MS (ISP): 483.3 (M+H)$^+$.

Example 138

N-[1-(3,5-Diethoxy-4-imidazol-1-yl-benzyl)-piperidin-4-yl]-3-methanesulfonyl-benzamide The compound was prepared in analogy to example 125, but starting the whole reaction sequence with 3-methylsulfonylbenzoic acid instead of 5-methylnicotinic acid, as yellow solid.
MS (ISP): 527.3 (M+H)$^+$.

Example 139

N-[1-(2,6-Diethoxy-4'-trifluoromethyl-biphenyl-4-ylmethyl)-piperidin-4-yl]-6-methylamino-nicotinamide The title compound was prepared in analogy to example 131, but using in the reductive amination step 2,6-diethoxy-4'-trifluoromethyl-biphenyl-4-carbaldehyde instead of 2,6-diethoxy-4'-fluoro-biphenyl-4-carbaldehyde, as white crystals.
MS (ISP): 557.3 (M+H)$^+$.

The necessary intermediate 2,6-Diethoxy-4'-trifluoromethyl-biphenyl-4-carbaldehyde was prepared as described in example 94, but coupling in the Suzuki reaction 3,5-diethoxy-4-iodo-benzaldehyde instead of 3-benzyloxy-5-ethoxy-4-iodo-benzaldehyde with 4-trifluoromethyl-phenyl boronic acid instead of 4-fluorophenyl boronic acid, as white crystals.
MS (EI): 338.1 [M]$^+$.

Example 140

N-[1-(2,6-Diethoxy-4'-fluoro-biphenyl-4-ylmethyl)-piperidin-4-yl]-6-methylamino-nicotinamide The title compound was prepared in analogy to example 139, but using in the reductive amination step 2,6-diethoxy-4'-fluoro-biphenyl-4-carbaldehyde (example 102) instead of 2,6-diethoxy-4'-trifluoromethyl-biphenyl-4-carbaldehyde, as white crystals.
MS (ISP): 507.4 (M+H)$^+$.

Example 141

N-[1-(3,5-Diethoxy-4-imidazol-1-yl-benzyl)-piperidin-4-yl]-6-methylamino-nicotinamide The compound was prepared in analogy to example 125, but using in the reductive amination step 6-methylamino-N-piperidin-4-yl-nicotinamide as amine component instead of 5-methyl-N-piperidin-4-yl-nicotinamide, as light yellow gum.
MS (ISP): 479.3 (M+H)$^+$.

Example 142

Methanesulfonic acid 3-[1-(3-ethoxy-4-imidazol-1-yl-benzyl)-piperidin-4-ylcarbamoyl]-phenyl ester The title compound was prepared in analogy to example 137, but starting the whole reaction sequence with 3-methanesulfonyloxy-benzoic acid instead of 3-methylsulfonyl-benzoic acid, as colorless gum.
MS (ISP): 499.1 (M+H)$^+$.

Example 143

N-[1-(3,5-Diethoxy-4-fluoro-benzyl)-piperidin-4-yl]-5-methoxy-isophthalamic acid methyl ester In analogy to the procedure described in example 50k), 5-methoxy-N-piperidin-4-yl-isophthalamic acid methyl ester [prepared from 5-methoxy-isophthalic acid monomethyl ester (Synthetic Communications, 31(12), 1921-1926; 2001) by condensation with 4-amino-piperidine-carboxylic acid tert-butyl ester, using acid activation with 2-chloro-4,6-dimethoxy-1,3,5-triazine in analogy to the procedure described in example 50 h) followed by Boc cleavage with TFA in analogy to the procedure described in example 50i)] was reacted with 3,5-diethoxy-4-fluoro-benzaldehyde (example 50 g), sodium cyanoborohydride, N-ethyl-diisopropylamine and acetic acid in ethanol at 50° C. to yield the title compound as colorless solid. MS: 489.3 (MH$^+$).

Example 144

N-[1-(3,5-Diethoxy-4-pyrrol-1-yl-benzyl)-piperidin-4-yl]-5-methoxy-isophthalamic acid methyl ester In analogy to the procedure described in example 50k), 5-methoxy-N-piperidin-4-yl-isophthalamic acid methyl ester (example 143) was reacted with 3,5-diethoxy-4-pyrrol-1-yl-benzaldehyde (example 40b), sodium cyanoborohydride, N-ethyl-diisopropylamine and acetic acid in ethanol at 50° C. to yield the title compound as light yellow solid. MS: 536.5 (MH$^+$).

Example 145

N-[1-(3,5-Diisopropoxy-benzyl)-piperidin-4-yl]-5-methoxy-isophthalamic acid methyl ester In analogy to the procedure described in example 50k), 5-methoxy-N-piperidin-4-yl-isophthalamic acid methyl ester (example 143) was reacted with 3,5-diisopropoxy-benzaldehyde (example 126b), sodium cyanoborohydride, N-ethyl-diisopropylamine and acetic acid in ethanol at 50-C to yield the title compound as colorless oil. MS: 499.3 (MH$^+$).

Example 146

N-[1-(3,5-Diethoxy-4-fluoro-benzyl)-piperidin-4-yl]-5-methoxy-isophthalamic acid In analogy to the procedure described in example 53, N-[1-(3,5-diethoxy-4-fluoro-benzyl)-piperidin-4-yl]-5-methoxy-isophthalamic acid methyl ester (example 143) was saponified to yield the title compound as colorless solid. MS: 475.1 (MH$^+$).

Example 147

N-[1-(3,5-Diethoxy-4-pyrrol-1-yl-benzyl)-piperidin-4-yl]-5-methoxy-isophthalamic acid In analogy to the procedure described in example 53, N-[1-(3,5-diethoxy-4-pyrrol-1-yl-benzyl)-piperidin-4-yl]-5- methoxy-isophthalamic acid methyl ester (example 144) was saponified to yield the title compound as colorless solid. MS: 522.3 (MH+).

Example 148

N-[1-(3,5-Diisopropoxy-benzyl)-piperidin-4-yl]-5-methoxy-isophthalamic acid

In analogy to the procedure described in example 53, N-[1-(3,5-diisopropoxy-benzyl)-piperidin-4-yl]-5-methoxy-isophthalamic acid methyl ester (example 145) was saponified to yield the title compound as off-white solid. MS: 485.3 (MH+).

Example 149

N-[1-(3,5-Diethoxy-4-imidazol-1-yl-benzyl)$_g$-piperidin-4-yl]-6-dimethylamino-5-methyl-nicotinamide The title compound was prepared in analogy to example 132, but using in the reductive amination step 3,5-diethoxy-4-imidazol-1-yl-benzaldehyde instead of 3,5-diethoxy-4-fluoro-benzaldehyde, as yellow oil.
MS (ISP): 507.4 (M+H)+.

Example 150

6-Chloro-N-[1-(3,5-diisopropoxy-benzyl)-piperidin-4-yl]-nicotinamide

The title compound was prepared in analogy to example 131, but starting the whole reaction sequence with 6-chloronicotinic acid instead of 6-methylaminonicotinic acid, as white solid.
MS (ISP): 446.3 (M+H)+.

Example 151

6-Chloro-N-[1-(3-ethoxy-4-methyl-benzyl)-piperidin-4-yl]-nicotinamide

The title compound was prepared in analogy to example 150, but using in the reductive amination step 3-ethoxy-4-methyl-benzaldehyde instead of 3,5-diisopropoxy-benzaldehyde, as white crystals.
MS (ISP): 388.3 (M+H)+.

Example 152

N-[1-(2,6-Diethoxy-biphenyl-4-ylmethyl)-piperidin-4-yl]-5-methyl-nicotinamide

The title compound was prepared in analogy to example 102, but starting the whole reaction sequence with 5-methylnicotinic acid instead of 3-methanesulfonyloxy-benzoic acid, and using in the reductive amination step 2,6-diethoxy-biphenyl-4-carbaldehyde instead of 2-benzyloxy-6-ethoxy-4'-fluoro-biphenyl-4-carbaldehyde, as white crystals.
MS (ISP): 474.3 (M+H)+.
The necessary intermediate 2,6-Diethoxy-biphenyl-4-carbaldehyde was prepared as described in example 94, but reacting in the Suzuki coupling 3,5-diethoxy-4-iodo-benzaldehyde (CAS No. 338454-05-0) instead of 3-benzyloxy-5-ethoxy-4-iodo-benzaldehyde with phenyl boronic acid instead of 4-fluorophenyl boronic acid, as white solid.
MS (EI): 270.2 [M]+.

Example 153

N-[1-(2,6-Diethoxy-4'-fluoro-biphenyl-4-ylmethyl)-piperidin-4-yl]-5-methyl-nicotinamide The title compound was prepared in analogy to example 152, but using in the reductive amination step 2,6-diethoxy-4'-fluoro-biphenyl-4-carbaldehyde instead of 2,6-diethoxy-biphenyl-4-carbaldehyde, as light yellow solid.
MS (ISP): 492.5 (M+H)+.

Example 154

6-Chloro-N-[1-(2,6-diethoxy-4'-fluoro-biphenyl-4-ylmethyl)-piperidin-4-yl]-nicotinamide The title compound was prepared in analogy to example 151, but using in the reductive amination step 2,6-diethoxy-4'-fluoro-biphenyl-4-carbaldehyde (example 102) instead of 3-ethoxy-4-methyl-benzaldehyde, as white crystals.
MS (ISP): 512.3 (M+H)+.

Example 155

6-Chloro-N-[1-(2-ethoxy-4'-fluoro-biphenyl-4-ylmethyl)-piperidin-4-yl]-nicotinamide The title compound was prepared in analogy to example 151, but using in the reductive amination step 2-ethoxy-4'-fluoro-biphenyl-4-carbaldehyde instead of 3-ethoxy-4-methyl-benzaldehyde, as white crystals.
MS (ISP): 468.3 (M+H)+.

Example 156

N-[1-(2,6-Diethoxy-biphenyl-4-ylmethyl)-piperidin-4-yl]-6-methylamino-nicotinamide The title compound was prepared in analogy to example 140, but using in the reductive amination step 2,6-diethoxy-biphenyl-4-carbaldehyde instead of 2,6-diethoxy-4'-fluoro-biphenyl-4-carbaldehyde, as white solid.
MS (ISP): 489.3 (M+H)+.

Example 157

6-Amino-N-[1-(3,5-diethoxy-4-imidazol-1-yl-benzyl)-piperidin-4-yl]-5-methyl-nicotinamide The compound was prepared in analogy to example 108, but using in the reductive amination step 3,5-diethoxy-4-imidazol-1-yl-benzaldehyde (example 125) instead of 2-ethoxy-4'-fluoro-biphenyl-4-carbaldehyde, as white solid.
MS (ISP): 479.3 (M+H)+.

Example 158

N-[1-(4-Cyclopropyl-3,5-diethoxy-benzyl)-piperidin-4-yl]-5-methyl-nicotinamide

The title compound was prepared in analogy to example 152, but using in the reductive amination step 4-cyclopropyl-3,5-diethoxy-benzaldehyde instead of 2,6-diethoxy-biphenyl-4-carbaldehyde, as white solid.
MS (ISP): 438.2 (M+H)+.
The necessary intermediate 4-Cyclopropyl-3,5-diethoxy-benzaldehyde was prepared as follows:

3,5-Diethoxy-4-iodo-benzaldehyde (CAS No. 338454-05-0, 0.500 g, 1.56 mmol) was dissolved under Ar in 6.25 ml of abs. toluene and 0.69 ml of water and treated successively with cyclopropyl boronic acid (0.268 g, 2 eq.), $K_3PO_4$ (1.78 g, 5.4 eq.), tricyclohexylphosphine (0.096 g, 0.22 eq.), and finally $Pd(OAc)_2$ (0.039 g, 0.11 eq.). The reaction flask was closed with a septum and the mixture was allowed to react for 16 h at 100° C. Pouring onto crashed ice, twofold extraction with AcOEt, washing with water, drying over sodium sulfate, and evaporation of the solvents, followed by flash chromatography (silica gel, hexane/AcOEt=9/1) afforded 0.306 g of the title compound as yellow solid.
MS (EI): 234.2 [M]$^+$.

Example 159

6-Chloro-N-[1-(3,5-diethoxy-4-fluoro-benzyl)-piperidin-4-yl]-nicotinamide

The title compound was prepared in analogy to example 151, but using in the reductive amination step 3,5-diethoxy-4-fluoro-benzaldehyde instead of 3-ethoxy-4-methyl-benzaldehyde, as white crystals.
MS (ISP): 436.2 (M+H)$^+$.

Example 160

N-[1-(3,5-Diethoxy-4-fluoro-benzyl)-piperidin-4-yl]-6-isopropylamino-nicotinamide The title compound was prepared in analogy to example 159, but running the reductive amination step with 6-isopropylamino-N-piperidin-4-yl-nicotinamide instead of 6-chloro-N-piperidin-4-yl-nicotinamide, as white crystals.
MS (ISP): 459.3 (M+H)$^+$.
The necessary intermediate 6-Isopropylamino-N-piperidin-4-yl-nicotinamide was prepared as follows:
4-[(6-Chloro-pyridine-3-carbonyl)-amino]-piperidine-1-carboxylic acid tert-butyl ester (intermediate of example 150, 1.000 g, 2.94 mmol) was dissolved in 5 ml of abs. EtOH and 5 ml of isopropylamine and heated for 5 h at 125° C. in a microwave oven. Cooling and evaporation of all volatiles, followed by flash chromatography (silica gel, hexane/AcOEt=1/1 to AcOEt) yielded 0.453 g of 4-[(6-isopropylamino-pyridine-3-carbonyl)-amino]-piperidine-1-carboxylic acid tert-butyl esteras light brown foam.
MS (ISP): 363.4 [M+H]$^+$.
The BOC group was cleaved by dissolving the above prepared product in 5 ml of $CH_2Cl_2$ and treating it with 1.0 ml of trifluoroacetic acid. After stirring for 16 h at ambient temperature, TLC indicated the absence of starting material. Evaporation of all volatiles left 0.702 g of the title compound as trifluoroacetate as light brown amorphous solid which was used without further purification.
MS (ISP): 263.3 [M+H]$^+$.

Example 161

N-[1-(3-Ethoxy-4-methyl-benzyl)-piperidin-4-yl]-6-isopropylamino-nicotinamide

The compound was prepared in analogy to example 160, but using in the reductive amination step 3-ethoxy-4-methyl-benzaldehyde instead of 3,5-diethoxy-4-fluoro-benzaldehyde, as white crystals.
MS (ISP): 411.1 (M+H)$^+$.

Example 162

N-[1-(3,5-Diisopropoxy-benzyl)-piperidin-4-yl]-6-isopropylamino-nicotinamide

The title compound was prepared in analogy to example 160, but using in the reductive amination step 3,5-diisopropoxy-benzaldehyde instead of 3,5-diethoxy-4-fluoro-benzaldehyde, as white foam.
MS (ISP): 469.2 (M+H)$^+$.

Example 163

N-[1-(2-Ethoxy-4'-fluoro-biphenyl-4-ylmethyl)-piperidin-4-yl]-6-isopropylamino-nicotinamide The title compound was prepared in analogy to example 160, but using in the reductive amination step 2-ethoxy-4'-fluoro-biphenyl-4-carbaldehyde instead of 3,5-diethoxy-4-fluoro-benzaldehyde, as white solid.
MS (ISP): 491.2 (M+H)$^+$.

Example 164

N-[1-(4-Cyclopropyl-3-ethoxy-benzyl)-piperidin-4-yl]-5-methyl-nicotinamide

The title compound was prepared in analogy to example 152, but using in the reductive amination step 4-cyclopropyl-3-ethoxy-benzaldehyde instead of 2,6-diethoxy-biphenyl-4-carbaldehyde, as white solid.
MS (ISP): 394.2 (M+H)$^+$.
The necessary intermediate 4-Cyclopropyl-3-ethoxy-benzaldehyde was prepared as described in example 158, but using 3-ethoxy-4-iodo-benzaldehyde (synthesized from 3-ethoxy-4-iodo-benzoic acid ethyl ester (CAS NO. 741699-04-7) by DIBAL-H reduction followed by $MnO_2$ oxidation) as starting material, as light brown oil.
MS (EI): 190.2 [M]$^+$.

Example 165

6-Amino-N-[1-(4-cyclopropyl-3-ethoxy-benzyl)-piperidin-4-yl]-nicotinamide

The title compound was prepared in analogy to example 164, but starting the whole reaction sequence with 6-aminonicotinic acid instead of 5-methylnicotinic acid, as white solid.
MS (ISP): 395.2 (M+H)$^+$.

Example 166

N-[1-(4-Cyclopropyl-3-ethoxy-benzyl)-piperidin-4-yl]-6-methylamino-nicotinamide

The compound was prepared in analogy to example 164, but starting the whole reaction sequence with 6-methylaminonicotinic acid instead of 5-methylnicotinic acid, as off-white solid.
MS (ISP): 409.2 (M+H)$^+$.

Example 167

6-Amino-N-[1-(2,6-diethoxy-4'-fluoro-biphenyl-4-ylmethyl)-piperidin-4-yl]-nicotinamide The title compound was prepared in analogy to example 140, but starting the whole reaction sequence with 6-aminonicotinic acid instead of 6-methylaminonicotinic acid, as white solid.
MS (ISP): 493.4 (M+H)$^+$.

Example 168

4-{3-[1-(3,5-Diethoxy-4-fluoro-benzyl)-piperidin-4-ylcarbamoyl]-5-methoxy-phenoxy}-butyric acid methyl ester

4-[3-Methoxy-5-(3-methoxycarbonyl-propoxy)-benzoylamino]-piperidine-1-carboxylic acid tert-butyl ester 1.60 g (4.6 mmol) of 4-(3-hydroxy-5-methoxy-benzoylamino)-piperidine-1-carboxylic acid tert-butyl ester [prepared from 3-hydroxy-5-methoxy-benzoic acid by reaction with 4-amino-piperidine-carboxylic acid tert-butyl ester, N-(3-dimethylaminopropyl)-N'-ethyl-carbodiimide hydrochloride and N,N-dimethyl-4-aminopyridine in dichloromethane/tetrahydrofuran between 0° C. and rt in analogy to example 60d)] was dissolved in 65 mL of MeCN at rt; 1.29 g (9.4 mmol) of anhydrous potassium carbonate was added at 5° C.; then, 0.61 mL (0.87 g=4.8 mmol) of 4-bromo-butyric acid methyl ester was added drop by drop. The reaction mixture was stirred at 95° C. for 22 hours. It was then cooled down to ambient temperature, poured into crashed ice and extracted twice with EtOAc. The organic phases were washed with water and brine, dried over MgSO$_4$, filtered and evaporated i.V. to yield 1.91 g of the title compound as colorless solid. MS: 451.1 (MH$^+$).

4-{3-[1-(3,5-Diethoxy-4-fluoro-benzyl)-piperidin-4-ylcarbamoyl]-5-methoxy-phenoxy}-butyric acid methyl ester In analogy to the procedure described in example 50k), 4-[3-methoxy-5-(piperidin-4-ylcarbamoyl)-phenoxy]-butyric acid methyl ester [prepared from 4-[3-methoxy-5-(3-methoxycarbonyl-propoxy)-benzoylamino]-piperidine-1-carboxylic acid tert-butyl ester by Boc cleavage in analogy to example 50i)] was reacted with 3,5-diethoxy-4-fluoro-benzaldehyde (example 50 g), sodium cyanoborohydride, N-ethyl-diisopropylamine and acetic acid in ethanol at 50° C. to yield the title compound as colorless solid. MS: 547.3 (MH$^+$).

Example 169

4-{3-[1-(3,5-Diisopropoxy-benzyl)-piperidin-4-ylcarbamoyl]-5-methoxy-phenoxy}-butyric acid methyl ester In analogy to the procedure described in example 50k), 4-[3-methoxy-5-(piperidin-4-ylcarbamoyl)-phenoxy]-butyric acid methyl ester (example 168b) was reacted with 3,5-diisopropoxy-benzaldehyde (example 126b), sodium cyanoborohydride, N-ethyl-diisopropylamine and acetic acid in ethanol at 50° C. to yield the title compound as colorless oil. MS: 557.3 (MH$^+$).

Example 170

N-[1-(3,5-Diethoxy-4-fluoro-benzyl)-piperidin-4-yl]-3-methoxy-5-(1H-tetrazol-5-ylmethoxy)-benzamide

(1-Trityl-1H-tetrazol-5-yl)-methanol and/or (2-trityl-2H-tetrazol-5-yl)-methanol 2.55 g (25.5 mMol) of (2H-tetrazol-5-yl)-methanol (PCT Int. Appl. (1998), 101 pp., WO 98/14450 A1) was suspended under Ar in 30 mL of THF at rt; while stirring, 2.71 g (1.05 eq.) of triethylamine was added. Then, 7.45 g (1.05 eq.) of triphenyl-chloromethane dissolved in 30 mL of THF was added at 40° C. within 5 min. Subsequently, the reaction mixture was stirred at 40° C. for 2 h. Then, it was cooled down, poured into 50 mL of ice cold water and extracted tree times with 100 mL of ethylacetate; the organic phases were washed with water, dried over MgSO$_4$, filtered and evaporated i.v. The crude product was purified by chromatography (silicagel, eluent:gradient of ethylacetate/heptane) to yield 7.3 g of the title compound as colorless crystals. MS: 342.1 (M$^+$).

4-[3-Methoxy-5-(1-trityl-1H-tetrazol-5-ylmethoxy)-benzoylamino]-piperidine-1-carboxylic acid tert-butyl ester and/or 4-[3-Methoxy-5-(2-trityl-2H-tetrazol-5-ylmethoxy)-benzoylamino]-piperidine-1-carboxylic acid tert-butyl ester 1.60 g (4.6 mMol) of 4-(3-hydroxy-5-methoxy-benzoylamino)-piperidine-1-carboxylic acid tert-butyl ester (example 168a), 1.72 g (1.10 eq.) of (1-trityl-1H-tetrazol-5-yl)-methanol and/or (2-trityl-2H-tetrazol-5-yl)-methanol and 1.57 g (1.30 eq.) of triphenylphosphine were dissolved in 20 mL of THF and the reaction mixture was cooled down to 15° C.; a solution of 1.34 g (1.25 eq.) of di-tert-butyl azodicarboxylate in 10 mL of THF was added drop by drop. Then, the reaction mixture was warmed up to ambient temperature. After 5 hours, the solvent was evaporated i.V. and the residue (6.54 g) was purified by chromatography (silicagel, eluent: gradient of n-heptane/EtOAc) to yield 2.21 g of the title compound as colorless solid. MS: 692.3 (M+NH$_4$)$^+$.

N-[1-(3,5-Diethoxy-4-fluoro-benzyl)-piperidin-4-yl]-3-methoxy-5-(1H-tetrazol-5-ylmethoxy)-benzamide In analogy to the procedure described in example 50k), 3-methoxy-N-piperidin-4-yl-5-(1H-tetrazol-5-ylmethoxy)-benzamide [prepared from 4-[3-methoxy-5-(1-trityl-1H-tetrazol-5-ylmethoxy)-benzoylamino]-piperidine-1-carboxylic acid tert-butyl ester and/or 4-[3-methoxy-5-(2-trityl-2H-tetrazol-5-ylmethoxy)-benzoylamino]-piperidine-1-carboxylic acid tert-butyl ester by reaction with trifluoroacetic acid in dichloromethane in analogy to the procedure described in example 50i)] was reacted with 3,5-diethoxy-4-fluoro-benzaldehyde (example 50 g), sodium cyanoborohydride, N-ethyl-diisopropylamine and acetic acid in ethanol at 50° C. to yield the title compound as off-white solid. MS: 529.2 (MH$^+$).

Example 171

N-[1-(3,5-Diethoxy-4-pyrrol-1-yl-benzyl)-piperidin-4-yl]-3-methoxy-5-(1H-tetrazol-5-ylmethoxy)-benzamide In analogy to the procedure described in example 50k), 3-methoxy-N-piperidin-4-yl-5-(1H-tetrazol-5-ylmethoxy)-benzamide (example 170c) was reacted with 3,5-diethoxy-4-pyrrol-1-yl-benzaldehyde (example 40b), sodium cyanoborohydride, N-ethyl-diisopropylamine and acetic acid in ethanol at 50° C. to yield the title compound as off-white solid. MS: 576.2 (MH$^+$).

Example 172

N-[1-(3,5-Diisopropoxy-benzyl)-piperidin-4-yl]-3-methoxy-5-(1H-tetrazol-5-ylmethoxy)-benzamide In analogy to the procedure described in example 50k), 3-methoxy-N-piperidin-4-yl-5-(1H-tetrazol-5-ylmethoxy)-benzamide (example 170c) was reacted with 3,5-diisopropoxy-benzaldehyde (example 126b), sodium cyanoborohydride, N-ethyl-diisopropylamine and acetic acid in ethanol at 50° C. to yield the title compound as off-white solid. MS: 539.4 (MH$^+$).

Example 173

4-{3-[1-(3,5-Diethoxy-4-fluoro-benzyl)-piperidin-4-ylcarbamoyl]-5-methoxy-phenoxy}-butyric acid In analogy to the procedure described in example 53, 4-{3-[1-(3,5-diethoxy-4-fluoro-benzyl)-piperidin-4-ylcarbamoyl]-5-methoxy-phenoxy}-butyric acid methyl ester (example 168) was saponified to yield the title compound as colorless solid. MS: 533.3 (MH$^+$).

Example 174

4-{3-[1-(3,5-Diisopropoxy-benzyl)-piperidin-4-ylcarbamoyl]-5-methoxy-phenoxy}-butyric acid In analogy to the procedure described in example 53, 4-{3-[1-(3,5-diisopropoxy-benzyl)-piperidin-4-ylcarbamoyl]-5-methoxy-phenoxy}-butyric acid methyl ester (example 169) was saponified to yield the title compound as colorless solid. MS: 565.4 (MNa$^+$).

Example 175 rac-3-(2,3-Dihydroxy-propoxy)-N-[1-(3,5-diisopropoxy-benzyl)-piperidin-4-yl]-5-methoxy-benzamide rac-4-[3-(2,2-Dimethyl-[1,31 dioxolan-4-yl-methoxy)-5-methoxy-benzoylamino]-piperidine-1-carboxylic acid tert-butyl ester 1.60 g (4.6 mmol) of 4-(3-hydroxy-5-methoxy-benzoylamino)-piperidine-1-carboxylic acid tert-butyl ester (example 168a) was dissolved in 50 ml of MeCN at rt; 1.29 g (9.4 mmol) of anhydrous potassium carbonate was added, followed by 1.495 g (4.8 mmol) of rac-2,2-dimethyl-1,3-dioxolan-4-yl-methyl p-toluenesulfonate. The reaction mixture was stirred at reflux for 22 hours. It was then cooled down to ambient temperature and poured into crashed ice and extracted twice with EtOAc. The organic phases were washed with water and brine, dried over MgSO$_4$, filtered and evaporated i.V. and the residue (2.11 g) was purified by chromatography (SiO$_2$, MeCl$_2$/MeOH) to yield 1.52 g of the title compound as a colorless amorphous solid. MS: 465.2 (MH$^+$).

b] rac-3-(2,3-Dihydroxy-propoxy)-5-methoxy-N-piperidin-4-yl-benzamide trifluoroacetate 1.45 g (3.1 mmol) of rac-4-[3-(2,2-dimethyl-[1,3]dioxolan-4-ylmethoxy)-5-methoxy-benzoylamino]-piperidine-1-carboxylic acid tert-butyl ester was dissolved in 14 mL of MeCl$_2$; while stirring, 2.39 mL (3.559 g=31.2 mmol) of trifluoroacetic acid was added drop by drop. After 16 hours, the reaction mixture was warmed up to reflux and stirred for another 21 hours; it was then evaporated and dried at high vacuum to yield 1.86 g of the crude title compound, which was used without further purification. MS: 325.4 (MH$^+$).

rac-3-(2,3-Dihydroxy-propoxy)-N-[1-(3,5-diisopropoxy-benzyl)-piperidin-4-yl]-5-methoxy-benzamide In analogy to the procedure described in example 50k), crude rac-3-(2,3-dihydroxy-propoxy)-5-methoxy-N-piperidin-4-yl-benzamide trifluoroacetate was reacted with 3,5-diisopropoxy-benzaldehyde (example 126b), sodium cyanoborohydride, N-ethyl-diisopropylamine and acetic acid in ethanol at 50° C. to yield the title compound as colorless amorphous solid. MS: 531.3 (MH$^+$).

Example 176 rac-N-[1-(3,5-Diethoxy-4-pyrrol-1-yl-benzyl)-piperidin-4-yl]-3-(2,3-dihydroxy-propoxy)-5-methoxy-benzamide In analogy to the procedure described in example 50k), crude rac-3-(2,3-dihydroxy-propoxy)-5-methoxy-N-piperidin-4-yl-benzamide trifluoroacetate (example 175b) was reacted with 3,5-diethoxy-4-pyrrol-1-yl-benzaldehyde (example 40b), sodium cyanoborohydride, N-ethyl-diisopropylamine and acetic acid in ethanol at 50° C. to yield the title compound as yellow oil. MS: 568.5 (MH$^+$).

Example 177 rac-N-[1-(3,5-Diethoxy-4-fluoro-benzyl)-piperidin-4-yl]-3-(2,3-dihydroxy-propoxy)-5-methoxy-benzamide In analogy to the procedure described in example 50k), crude rac-3-(2,3-dihydroxy-propoxy)-5-methoxy-N-piperidin-4-yl-benzamide trifluoroacetate (example 175b) was reacted with 3,5-diethoxy-4-fluoro-benzaldehyde (example 50 g), sodium cyanoborohydride, N-ethyl-diisopropylamine and acetic acid in ethanol at 50° C. to yield the title compound as colorless amorphous solid. MS: 521.4 (MH$^+$).

Example 178

N-[1-(3,5-Diethoxy-4-fluoro-benzyl)-piperidin-4-yl]-3-(2H-tetrazol-5-yl)-benzamide In analogy to the procedure described in example 50k), N-piperidin-4-yl-3-(1H-tetrazol-5-yl)-benzamide [prepared from 3-(1H-tetrazol-5-yl)-benzoic acid by reaction with 4-amino-piperidine-carboxylic acid tert-butyl ester, N-(3-dimethylaminopropyl)-N'-ethyl-carbodiimide hydrochloride and N,N-dimethyl-4-aminopyridine in dichloromethane at rt in analogy to example 60d) to give 4-[3-(2H-tetrazol-5-yl)-benzoylamino]-piperidine-1-carboxylic acid tert-butyl ester followed by Boc cleavage in analogy to example 50i)] was reacted with 3,5-diethoxy-4-fluoro-benzaldehyde (example 50 g), sodium cyanoborohydride, N-ethyl-diisopropylamine and acetic acid in ethanol at 50° C. to yield the title compound as colorless solid. MS: 469.4 (MH+).

Example 179

6-Amino-N-[1-(3,5-diethoxy-4-imidazol-1-yl-benzyl)-piperidin-4-yl]-nicotinamide

The title compound was prepared in analogy to example 157, but starting the whole reaction sequence with 6-aminonicotinic acid instead of 6-amino-5-methyl-nicotinic acid, as off-white solid.
MS (ISP): 465.2 (M+H)+.

Example 180

N-[1-(4-Cyclopropyl-3,5-diethoxy-benzyl)-piperidin-4-yl]-6-methylamino-nicotinamide The title compound was prepared in analogy to example 158, but starting the whole reaction sequence with 6-methylamino-nicotinic acid instead of 5-methyl-nicotinic acid, as colorless amorphous solid.
MS (ISP): 453.3 (M+H)+.

Example 181

6-Amino-N-[1-(4-cyclopropyl-3,5-diethoxy-benzyl)-piperidin-4-yl]-5-methyl-nicotinamide The title compound was prepared in analogy to example 180, but starting the whole reaction sequence with 6-amino-5-methyl-nicotinic acid instead of 6-methylamino-nicotinic acid, as off-white solid.
MS (ISP): 453.3 (M+H)+.

Example 182

Methanesulfonic acid 3-[1-(4-cyclopropyl-3,5-diethoxy-benzyl)-piperidin-4-ylcarbamoyl]-phenyl ester The title compound was prepared in analogy to example 180, but starting the whole reaction sequence with 3-methanesulfonyloxy-benzoic acid instead of 6-methylamino-nicotinic acid, as colorless foam.
MS (ISP): 517.2 (M+H)+.

Example 183

N-[1-(4-Cyclopropyl-3-ethoxy-benzyl)-piperidin-4-yl]-3-methanesulfonyl-benzamide The title compound was prepared in analogy to example 164, but starting the whole reaction sequence with 3-methylsulfonylbenzoic acid instead of 5-methyl-nicotinic acid, as white crystals.
MS (ISP): 457.2 (M+H)+.

Example 184

N-[1-(2,6-Diethoxy-4'-fluoro-biphenyl-4-ylmethyl)-piperidin-4-yl]-6-isopropylamino-nicotinamide The title compound was prepared in analogy to example 160, but using for the reductive amination 2,6-diethoxy-4'-fluoro-biphenyl-4-carbaldehyde instead of 3,5-diethoxy-4-fluoro-benzaldehyde, as white crystals.
MS (ISP): 535.4 (M+H)+.

Example 185

6-Amino-N-[1-(2,6-diethoxy-biphenyl-4-ylmethyl)-piperidin-4-yl]-nicotinamide

The title compound was prepared in analogy to example 156, but starting the whole reaction sequence with 6-aminonicotinic acid instead of 6-methylamino-nicotinic acid, as white solid.
MS (ISP): 475.2 (M+H)+.

Example 186

N-[1-(4-Cyclopropyl-3-ethoxy-benzyl)-piperidin-4-yl]-6-isopropylamino-nicotinamide The title compound was prepared in analogy to example 184, but using for the reductive amination 4-cyclopropyl-3-ethoxy-benzaldehyde (example 164) instead of 2,6-diethoxy-4'-fluoro-biphenyl-4-carbaldehyde, as white crystals.
MS (ISP): 437.4 (M+H)+.

Example 187

N-[1-(4-Cyclopropyl-3,5-diethoxy-benzyl)-piperidin-4-yl]-3-methanesulfonyl-benzamide The title compound was prepared in analogy to example 182, but starting the whole reaction sequence with 3-methylsulfonylbenzoic acid instead of 3-methanesulfonyloxy-benzoic acid, as white solid.
MS (ISP): 501.1 (M+H)+.

Example 188

6-Cyclopropylamino-N-[1-(3,5-diethoxy-4-fluoro-benzyl)-piperidin-4-yl]-nicotinamide The title compound was prepared in analogy to example 160, but running the reductive amination step with 6-cyclopropylamino-N-piperidin-4-yl-nicotinamide instead of 6-isopropylamino-N-piperidin-4-yl-nicotinamide, as white crystals.
MS (ISP): 457.3 (M+H)+.

The necessary intermediate 6-Isopropylamino-N-piperidin-4-yl-nicotinamide was prepared as described in example 160, but using for the nucleophilic substitution cyclopropylamine instead of isopropylamine, as light brown gum.
MS (ISP): 261.3 (M+H)+.

Example 189

6-Cyclopropylamino-N-[1-(3,5-diisopropoxy-benzyl)-piperidin-4-yl]-nicotinamide

The title compound was prepared in analogy to example 188, but using for the reductive amination 3,5-diisopropoxy-benzaldehyde instead of of 3,5-diethoxy-4-fluoro-benzaldehyde, as white crystals.
MS (ISP): 467.2 (M+H)+.

Example 190

6-Cyclopropylamino-N-[1-(3-ethoxy-4-methyl-benzyl)-piperidin-4-yl]-nicotinamide

The title compound was prepared in analogy to example 188, but using for the reductive amination 3-ethoxy-4-methyl-benzaldehyde instead of 3,5-diethoxy-4-fluoro-benzaldehyde, as white crystals.
MS (ISP): 409.3 (M+H)+.

Example 191

6-Cyclopropylamino-N-[1-(2-ethoxy-4'-fluoro-biphenyl-4-ylmethyl)-piperidin-4-yl]-nicotinamide The title compound was prepared in analogy to example 188, but using for the reductive amination 2-ethoxy-4'-fluoro-biphenyl-4-carbaldehyde instead of 3,5-diethoxy-4-fluoro-benzaldehyde, as white crystals.
MS (ISP): 489.3 (M+H)$^+$.

Example 192

N-[1-(4-Cyclopropyl-3,5-diethoxy-benzyl)-piperidin-4-yl]-5-methyl-6-methylamino-nicotinamide This compound was prepared in analogy to example 121, but using for the reductive amination 4-cyclopropyl-3,5-diethoxy-benzaldehyde instead of 3,5-diethoxy-4-fluoro-benzaldehyde, as yellow foam.
MS (ISP): 467.4 (M+H)$^+$.

Example 193

N-[1-(2,6-Diethoxy-biphenyl-4-ylmethyl)-piperidin-4-yl]-5-methyl-6-methylamino-nicotinamide The title compound was prepared in analogy to example 121, but using for the reductive amination 2,6-diethoxy-biphenyl-4-carbaldehyde instead of 3,5-diethoxy-4-fluoro-benzaldehyde, as yellow foam.
MS (ISP): 503.3 (M+H)$^+$.

Example 194

6-Cyclopropylamino-N-[1-(4-cyclopropyl-3-ethoxy-benzyl)-piperidin-4-yl]-nicotinamide The title compound was prepared in analogy to example 188, but using for the reductive amination 4-cyclopropyl-3-ethoxy-benzaldehyde instead of 3,5-diethoxy-4-fluoro-benzaldehyde, as white crystals.
MS (ISP): 435.1 (M+H)$^+$.

Example 195

N-[1-(2,6-Diethoxy-4'-fluoro-biphenyl-4-ylmethyl)-piperidin-4-yl]-5-methyl-6-methylamino-nicotinamide The compound was prepared in analogy to example 121, but using for the reductive amination 2,6-diethoxy-4'-fluoro-biphenyl-4-carbaldehyde instead of 3,5-diethoxy-4-fluoro-benzaldehyde, as light yellow solid.
MS (ISP): 521.3 (M+H)$^+$.

Example 196

N-[1-(4-Cyclopropyl-3-ethoxy-benzyl)-piperidin-4-yl]-5-methyl-6-methylamino-nicotinamide The title compound was prepared in analogy to example 121, but using for the reductive amination 4-cyclopropyl-3-ethoxy-benzaldehyde instead of 3,5-diethoxy-4-fluoro-benzaldehyde, as yellow foam.
MS (ISP): 523.1 (M+H)$^+$.

Example 197

6-Cyclopropylamino-N-[1-(4-cyclopropyl-3,5-diethoxy-benzyl)-piperidin-4-yl]-nicotinamide The title compound was prepared in analogy to example 188, but using for the reductive amination 4-cyclopropyl-3,5-diethoxy-benzaldehyde instead of 3,5-diethoxy-4-fluoro-benzaldehyde, as white crystals.
MS (ISP): 479.3 (M+H)$^+$.

Example 198

N-[1-(3,5-Diethoxy-4-[1,2,4]triazol-1-yl-benzyl)-piperidin-4-yl]-3-(2H-tetrazol-5-yl)-benzamide In analogy to the procedure described in example 50k), N-piperidin-4-yl-3-(1H-tetrazol-5-yl)-benzamide (example 178) was reacted with 3,5-diethoxy-4-[1,2,4]triazol-1-yl-benzaldehyde (example 129a), sodium cyanoborohydride, N-ethyl-diisopropylamine and acetic acid in ethanol at 50° C. to yield the title compound as light yellow solid. MS: 518.2 (MH$^+$).

Example 199

N-[1-(3,5-Diisopropoxy-benzyl)-piperidin-4-yl]-3-(2H-tetrazol-5-yl)-benzamide

In analogy to the procedure described in example 50k), N-piperidin-4-yl-3-(1H-tetrazol-5-yl)-benzamide (example 178) was reacted with 3,5-diisopropoxy-benzaldehyde (example 126b), sodium cyanoborohydride, N-ethyl-diisopropylamine and acetic acid in ethanol at 50° C. to yield the title compound as colorless solid. MS: 479.3 (MH$^+$).

Example 200

N-[1-(3,5-Diethoxy-4-pyrrol-1-yl-benzyl)-piperidin-4-yl]-3-(2H-tetrazol-5-yl)-benzamide In analogy to the procedure described in example 50k), N-piperidin-4-yl-3-(1H-tetrazol-5-yl)-benzamide (example 178) was reacted with 3,5-diethoxy-4-pyrrol-1-yl-benzaldehyde (example 40b), sodium cyanoborohydride, N-ethyl-diisopropylamine and acetic acid in ethanol at 50° C. to yield the title compound as off-white solid. MS: 516.2 (MH$^+$).

Example 201

6-Cyclopropylamino-N-[1-(2,6-diethoxy-4'-fluoro-biphenyl-4-ylmethyl)-piperidin-4-yl]-nicotinamide The title compound was prepared in analogy to example 197, but using for the reductive amination 2,6-diethoxy-4'-fluoro-biphenyl-4-carbaldehyde instead of 4-cyclopropyl-3,5-diethoxy-benzaldehyde, as white crystals.
MS (ISP): 533.4 (M+H)$^+$.

Example 202

N-[1-(4-Cyclopropyl-3,5-diethoxy-benzyl)-piperidin-4-yl]-3,5-dimethoxy-benzamide The title compound was prepared in analogy to example 197, but starting the reaction sequence with 3,5-dimethoxy-benzoic acid instead of 6-cyclopropylamino-nicotinic acid, as white solid.
MS (ISP): 483.3 (M+H)$^+$.

Example 203

N-[1-(2,6-Diethoxy-4'-fluoro-biphenyl-4-ylmethyl)-piperidin-4-yl]-3,5-dimethoxy-benzamide The title compound was prepared in analogy to example 202, but using for the reductive amination 2,6-diethoxy-4'-fluoro-biphenyl-4-carbaldehyde instead of 4-cyclopropyl-3,5-diethoxy-benzaldehyde, as off-white solid.
MS (ISP): 537.3 (M+H)$^+$.

Example 204

N-[1-(3-Ethoxy-4-methyl-benzyl)-piperidin-4-yl]-3,5-dimethoxy-benzamide

The title compound was prepared in analogy to example 202, but using for the reductive amination 3-ethoxy-4-methyl-benzaldehyde instead of 4-cyclopropyl-3,5-diethoxy-benzaldehyde, as colorless foam.
MS (ISP): 413.2 (M+H)$^+$.

Example 205

N-[1-(4-Cyclopropyl-3-ethoxy-benzyl)-piperidin-4-yl]-3,5-dimethoxy-benzamide

The title compound was prepared in analogy to example 202, but using for the reductive amination 4-cyclopropyl-3-ethoxy-benzaldehyde instead of 4-cyclopropyl-3,5-diethoxy-benzaldehyde, as white foam.
MS (ISP): 439.2 (M+H)$^+$.

Example 206

N-[1-(2-Ethoxy-4'-fluoro-biphenyl-4-ylmethyl)-piperidin-4-yl]-3,5-dimethoxy-benzamide This compound was prepared in analogy to example 202, but using for the reductive amination 2-ethoxy-4'-fluoro-biphenyl-4-carbaldehyde instead of 4-cyclopropyl-3,5-diethoxy-benzaldehyde, as white solid.
MS (ISP): 439.2 (M+H)$^+$.

Example 207

N-[1-(3,5-Diisopropoxy-benzyl)-piperidin-4-yl]-3,5-dimethoxy-benzamide

The compound was prepared in analogy to example 202, but using for the reductive amination 3,5-diisopropoxy-benzaldehyde instead of 4-cyclopropyl-3,5-diethoxy-benzaldehyde, as white solid.
MS (ISP): 471.0 (M+H)$^+$.

Example 208

N-[1-(3,5-Diethoxy-4-fluoro-benzyl)-piperidin-4-yl]-3,5-dimethoxy-benzamide

The title compound was prepared in analogy to example 202, but using for the reductive amination 3,5-diethoxy-4-fluoro-benzaldehyde instead of 4-cyclopropyl-3,5-diethoxy-benzaldehyde, as white solid.
MS (ISP): 461.1 (M+H)$^+$.

Example 209

N-[1-(2,6-Diethoxy-biphenyl-4-ylmethyl)-piperidin-4-yl]-3,5-bis-(2-fluoro-ethoxy)-benzamide The title compound was prepared in analogy to example 202, but starting the reaction sequence with 3,5-bis-(2-fluoro-ethoxy)-benzoic acid instead of 3,5-dimethoxybenzoic acid, and using for the reductive amination 2,6-diethoxy-biphenyl-4-carbaldehyde instead of 2,6-diethoxy-4'-fluoro-biphenyl-4-carbaldehyde, as white solid.
MS (ISP): 583.3 (M+H)$^+$.
The necessary intermediate was prepared as follows:

3,5-Bis-(2-fluoro-ethoxy)-benzoic acid methyl ester

To a solution of methyl 3,5-dihydroxybenzoate (1.00 g, 5.95 mmol) in 5.9 ml of DMF was added 3.0 eq. of 1-iodo-2-fluoroethane (3.10 g) and 3.0 eq. of K$_2$CO$_3$ (2.47 g) and the mixture kept for 12 h at 50° C. Pouring onto crashed ice/NH$_4$Cl, twofold extraction with AcOEt, washing with water and brine, drying over sodium sulfate, and evaporation of the solvents, followed by flash chromatography (SiO$_2$, hexane/AcOEt=7/3) left 1.45 g of the title compound as white solid.
MS (EI): 260.1 [M]$^+$.

3,5-Bis-(2-fluoro-ethoxy)-benzoic acid

The above prepared 3,5-bis-(2-fluoro-ethoxy)-benzoic acid methyl ester (1.45 g, 5.57 mmol) was dissolved in 19 ml of THF/ethanol=1/1 and treated with 9.3 ml of aq. NaOH (3M, 5 eq.). The mixture was stirred for 1.5 h at ambient temperature and was then poured onto crashed ice/AcOEt/HCl dil.; the organic layer was washed with water, dried over sodium sulfate, and evaporated to dryness to leave 1.36 g of the title compound as white solid.
MS (ISN): 245.2 [M−H]$^-$.

Example 210

N-[1-(3-Ethoxy-4-methyl-benzyl)-piperidin-4-yl]-3,5-bis-(2-fluoro-ethoxy)-benzamide The title compound was prepared in analogy to example 209, but using for the reductive amination 3-ethoxy-4-methyl-benzaldehyde instead of 2,6-diethoxy-biphenyl-4-carbaldehyde, as colorless semisolid.
MS (ISP): 477.1 (M+H)$^+$.

Example 211

N-[1-(3,5-Diethoxy-4-fluoro-benzyl)-piperidin-4-yl]-3,5-bis-(2-fluoro-ethoxy)-benzamide The compound was prepared in analogy to example 209, but using for the reductive amination 3,5-diethoxy-4-fluoro-benzaldehyde instead of 2,6-diethoxy-biphenyl-4-carbaldehyde, as white solid.
MS (ISP): 525.2 (M+H)$^+$.

Example 212

N-[1-(4-Cyclopropyl-3,5-diethoxy-benzyl)-piperidin-4-yl]-3,5-bis-(2-fluoro-ethoxy)-benzamide The title compound was prepared in analogy to example 209, but using for the reductive amination 4-cyclopropyl-3, 5-diethoxy-benzaldehyde instead of 2,6-diethoxy-biphenyl-4-carbaldehyde, as white solid.
MS (ISP): 547.3 (M+H)+.

Example 213

N-[1-(4-Chloro-3-ethoxy-benzyl)-piperidin-4-yl]-3,5-bis-(2-fluoro-ethoxy)-benzamide The title compound was prepared in analogy to example 209, but using for the reductive amination 4-chloro-3-ethoxy-benzaldehyde instead of 2,6-diethoxy-biphenyl-4-carbaldehyde, as colorless foam.
MS (ISP): 497.0 (M+H)+.

Example 214

N-[1-(3,5-Diisopropoxy-benzyl)-piperidin-4-yl]-3,5-bis-(2-fluoro-ethoxy)-benzamide The title compound was prepared in analogy to example 209, but using for the reductive amination 3,5-diisopropoxy-benzaldehyde instead of 2,6-diethoxy-biphenyl-4-carbaldehyde, as white foam.
MS (ISP): 535.4 (M+H)+.

Example 215

N-[1-(2,6-Diethoxy-4'-fluoro-biphenyl-4-ylmethyl)-piperidin-4-yl]-3,5-bis-(2-fluoro-ethoxy)-benzamide The title compound was prepared in analogy to example 209, but using for the reductive amination 2,6-diethoxy-4'-fluoro-biphenyl-4-carbaldehyde instead of 2,6-diethoxy-biphenyl-4-carbaldehyde, as white solid.
MS (ISP): 601.3 (M+H)+.

Example 216

N-[1-(2-Ethoxy-4'-fluoro-biphenyl-4-ylmethyl)-piperidin-4-yl]-3,5-bis-(2-fluoro-ethoxy)-benzamide The title compound was prepared in analogy to example 209, but using for the reductive amination 2-ethoxy-4'-fluoro-biphenyl-4-carbaldehyde instead of 2,6-diethoxy-biphenyl-4-carbaldehyde, as white foam.
MS (ISP): 557.2 (M+H)+.

Example 217

N-[1-(3,5-Diethoxy-4-fluoro-benzyl)-piperidin-4-yl]-3-hydroxymethyl-5-methoxy-benzamide In analogy to the procedure described in example 50k), 3-hydroxymethyl-5-methoxy-N-piperidin-4-yl-benzamide [prepared by i) saponification of 3-hydroxymethyl-5-methoxy-benzoic acid methyl ester [Synthetic Communications, 31(12), 1921-1926; 2001] with LiOH in THF/MeOH (2:1) to give 3-hydroxymethyl-5-methoxy-benzoic acid in analogy to the procedure described in example 53; ii) subsequent condensation with 4-amino-piperidine-carboxylic acid tert-butyl ester to give 4-(3-hydroxymethyl-5-methoxy-benzoylamino)-piperidine-1-carboxylic acid tert-butyl ester, using N-(3-dimethylaminopropyl)-N'-ethyl-carbodiimide hydrochloride and N,N-dimethyl-4-aminopyridine in MeCl$_2$ in analogy to the procedure described in example 60d); iii) Boc cleavage with TFA in analogy to the procedure described in example 50i)] was reacted with 3,5-diethoxy-4-fluoro-benzaldehyde (example 50 g), sodium cyanoborohydride, N-ethyl-diisopropylamine and acetic acid in ethanol at 50° C. to yield the title compound as off-white solid. MS: 461.1 (MH+).

Example 218

N-[1-(3,5-Diisopropoxy-benzoyl)-piperidin-4-yl]-3-hydroxymethyl-5-methoxy-benzamide In analogy to the procedure described in example 50k), 3-hydroxymethyl-5-methoxy-N-piperidin-4-yl-benzamide (example 217) was reacted with 3,5-diisopropoxy-benzaldehyde (example 126b), sodium cyanoborohydride, N-ethyl-diisopropylamine and acetic acid in ethanol at 50° C. to yield the title compound as colorless solid. MS: 471.1 (MH+).

Example 219

N-[1-(4-Chloro-3,5-diethoxy-benzyl)-piperidin-4-yl]-3-hydroxymethyl-5-methoxy-benzamide
4-Chloro-3,5-diethoxy-benzoic acid ethyl ester To a solution of 4-amino-3,5-diethoxy-benzoic acid ethyl ester (5.1 g, 20.13 mmol, 1.0 eq.; prepared as described in I. Kompis, A. Wick *Helv. Chim. Acta* 1977, 60, 3025-3034) in water (40 mL) and 37% hydrochloric acid (40 mL) at 0° C. was added sodium nitrite (1.67 g, 24.16 mmol, 1.2 eq.). After 10 min, copper(I) chloride (12.0 g, 120.81 mmol, 6.0 eq.) was added, the reaction mixture stirred for an additional 5 h at 0° C. and then the ice bath was removed. After stirring for 18 h the crude reaction mixture was adjusted to pH=8 by addition of a solution of 1 M NaOH and the aqueous layer extraced with ethyl acetate (3×100 mL). The combined organic phases were dried over MgSO$_4$, concentrated by evaporation under reduced pressure and the crude material purified with silica column chromatography using a MPLC system (CombiFlash Companion, Isco Inc.) eluting with a gradient of heptane/ethyl acetate providing 5.0 g (91%) of the title compound as off-white solid. MS: 273.3 (MH+).

N-[1-(4-Chloro-3,5-diethoxy-benzyl)-piperidin-4-yl]-3-hydroxymethyl-5-methoxy-benzamide In analogy to the procedure described in example 50k), 3-hydroxymethyl-5-methoxy-N-piperidin-4-yl-benzamide (example 217) was reacted with 4-chloro-3,5-diethoxy-benzaldehyde [prepared from 4-chloro-3,5-diethoxy-benzoic acid ethyl ester (example 219a) by reduction with di-isobutylaluminium hydride followed by oxidation with MnO$_2$ in analogy to the procedures described in example 1a)], sodium cyanoborohydride, N-ethyl-diisopropylamine and acetic acid in ethanol at 50° C. to yield the title compound as colorless oil. MS: 477.0 (MH+).

Example 220

N-[1-(2,6-Diethoxy-4'-fluoro-biphenyl-4-ylmethyl)-piperidin-4-yl]-3-hydroxymethyl-5-methoxy-benzamide In analogy to the procedure described in example 50k), 3-hydroxymethyl-5-methoxy-N-piperidin-4-yl-benzamide (example 217) was reacted with 2,6-diethoxy-4'-fluoro-biphenyl-4-carbaldehyde (example 102), sodium cyanoboro-

Example 221

6-Chloro-N-[1-(4-chloro-3,5-diethoxy-benzyl)-piperidin-4-yl]-nicotinamide

The title compound was prepared in analogy to example 150, but using in the reductive amination step 4-chloro-3,5-diethoxy-benzaldehyde instead of 3,5-diisopropoxy-benzaldehyde, as white crystals.

MS (ISP): 452.1 (M+H)$^+$.

Example 222

6-Chloro-N-[1-(4-cyclopropyl-3,5-diethoxy-benzyl)-piperidin-4-yl]-nicotinamide

The title compound was prepared in analogy to example 150, but using in the reductive amination step 4-cyclopropyl-3,5-diethoxy-benzaldehyde instead of 3,5-diisopropoxy-benzaldehyde, as white crystals.

MS (ISP): 458.2 (M+H)$^+$.

Example 223

3-Cyclopropyl-N-[1-(3-ethoxy-4-pyridin-4-yl-benzyl)-piperidin-4-yl]-5-methoxy-benzamide The title compound was prepared in analogy to example 111, but starting the reaction sequence with 3-cyclopropyl-5-methoxy-benzoic acid instead of 5-methyl-nicotinic acid, as white foam.

MS (ISP): 486.5 (M+H)$^+$.

The necessary intermediate was prepared as follows:

3-Methoxy-5-trifluoromethanesulfonyloxy-benzoic acid methyl ester

To a solution of 3-hydroxy-5-methoxy-benzoic acid methyl ester [CAS No. 19520-74-2] (0.930 g, 5.10 mmol) in 10 ml of CH$_2$Cl$_2$ was added at 0° C. 2.5 eq. of pyridine (1.01 g) followed by 1.2 eq. of trifluoromethanesulfonic anhydride (1.728 g), and the mixture kept for 0.25 h at 0° C. Warming to ambient temperature, pouring onto crashed ice/HCl, twofold extraction with AcOEt, washing with water and brine, drying over sodium sulfate, and evaporation of the solvents left 1.72 g of the title compound which was used in the next step without further purification.

3-Cyclopropyl-5-methoxy-benzoic acid methyl ester

The above prepared 3-methoxy-5-trifluoromethanesulfonyloxy-benzoic acid methyl ester (0.350 g, 1.11 mmol) was dissolved under Ar in 4.5 ml of abs. toluene and 0.49 ml of water and treated successively with cyclopropyl boronic acid (0.191 g, 2 eq.), K$_3$PO$_4$ (1.272 g, 5.4 eq.), tricyclohexylphosphine (0.069 g, 0.22 eq.), and finally Pd(OAc)$_2$ (0.028 g, 0.11 eq.). The reaction flask was closed with a septum and the mixture was allowed to react for 16 h at 100° C. Pouring onto crashed ice/NH$_4$Cl, twofold extraction with AcOEt, washing with water, drying over sodium sulfate, and evaporation of the solvents, followed by flash chromatography (silica gel, hexane/AcOEt=9/1), afforded 0.221 g of the title compound as yellow oil, 97% pure according to GC-analysis.

MS (EI): 206.2 [M]$^+$.

3-Cyclopropyl-5-methoxy-benzoic acid

The above prepared 3-cyclopropyl-5-methoxy-benzoic acid methyl ester (0.221 g, 1.07 mmol) was dissolved in 3.6 ml of THF/ethanol=1/1 and treated with 1.79 ml of aq. NaOH (3M, 5 eq.). The mixture was stirred for 1.5 h at ambient temperature and was then poured onto crashed ice/AcOEt/HCl dil.; the organic layer was washed with water, dried over sodium sulfate, and evaporated to dryness to leave 0.202 g of the title compound as white solid.

MS (EI): 192.2 [M]$^+$.

Example 224

3-Cyclopropyl-N-[1-(4-cyclopropyl-3,5-diethoxy-benzyl)-piperidin-4-yl]-5-methoxy-benzamide The title compound was prepared in analogy to example 223, but using in the reductive amination step 4-cyclopropyl-3,5-diethoxy-benzaldehyde instead of 3-ethoxy-4-pyridin-3-yl-benzaldehyde, as off-white semisolid.

MS (ISP): 493.4 (M+H)$^+$.

Example 225

3-Cyclopropyl-N-[1-(3,5-diethoxy-4-fluoro-benzyl)-piperidin-4-yl]-5-methoxy-benzamide The title compound was prepared in analogy to example 223, but using in the reductive amination step 3,5-diethoxy-4-fluoro-benzaldehyde instead of 3-ethoxy-4-pyridin-3-yl-benzaldehyde, as white foam.

MS (ISP): 471.0 (M+H)$^+$.

Example 226

3-Cyclopropyl-N-[1-(2,6-diethoxy-4'-fluoro-biphenyl-4-ylmethyl)-piperidin-4-yl]-5-methoxy-benzamide The title compound was prepared in analogy to example 223, but using in the reductive amination step 2,6-diethoxy-4'-fluoro-biphenyl-4-carbaldehyde instead of 3-ethoxy-4-pyridin-3-yl-benzaldehyde, as white solid.

MS (ISP): 547.3 (M+H)$^+$.

Example 227

6-Chloro-N-[1-(3,5-diethoxy-4-pyrrol-1-yl-benzyl)-piperidin-4-yl]-nicotinamide

The title compound was prepared in analogy to example 150, but using in the reductive amination step 3,5-diethoxy-4-pyrrol-1-yl-benzaldehyde (example 40b) instead of 3,5-diisopropoxy-benzaldehyde, as light yellow crystals.

MS (ISP): 483.2 (M+H)$^+$.

Example 228

N-[1-(2,6-Diethoxy-4'-fluoro-biphenyl-4-ylmethyl)-piperidin-4-yl]-3-methoxy-5-pyridin-4-yl-benzamide This compound was prepared in analogy to example 226, but starting the reaction sequence with 3-methoxy-5-pyridin-4-yl-benzoic acid instead of 3-cyclopropyl-5-methoxy-benzoic acid, as light yellow oil.

MS (ISP): 584.3 (M+H)$^+$.

The necessary starting material 3-Methoxy-5-pyridin-4-yl-benzoic acid was prepared as described in example 223b)-c), but using for the Suzuki—coupling 4-pyridylboronic acid instead of cyclopropyl boronic acid, as white solid.
MS (ISP): 230.3 (M+H)$^+$.

Example 229

4'-Fluoro-5-methoxy-biphenyl-3-carboxylic acid[1-(2,6-diethoxy-4'-fluoro-biphenyl-4-ylmethyl)-piperidin-4-yl]-amide The title compound was prepared in analogy to example 226, but starting the reaction sequence with 4'-fluoro-5-methoxy-biphenyl-3-carboxylic acid instead of 3-cyclopropyl-5-methoxy-benzoic acid, as white solid.
MS (ISP): 601.3 (M+H)$^+$.

The necessary starting material 4'-Fluoro-5-methoxy-biphenyl-3-carboxylic acid was prepared as described in example 223b)-c), but using for the Suzuki—coupling 4-fluorophenylboronic acid instead of cyclopropyl boronic acid, as off-white solid.
MS (ISP): 245.1 (M–H)$^-$.

Example 230

4'-Fluoro-5-methoxy-biphenyl-3-carboxylic acid[1-(3,5-diethoxy-4-fluoro-benzyl)-piperidin-4-yl]-amide The title compound was prepared in analogy to example 229, but using in the reductive amination step 3,5-diethoxy-4-fluoro-benzaldehyde instead of 2,6-diethoxy-4'-fluoro-biphenyl-4-carbaldehyde, as white solid.
MS (ISP): 525.2 (M+H)$^+$.

Example 231

4'-Fluoro-5-methoxy-biphenyl-3-carboxylic acid[1-(2-ethoxy-4'-fluoro-biphenyl-4-ylmethyl)-piperidin-4-yl]-amide The title compound was prepared in analogy to example 229, but using in the reductive amination step 2-ethoxy-4'-fluoro-biphenyl-4-carbaldehyde instead of 2,6-diethoxy-4'-fluoro-biphenyl-4-carbaldehyde, as white foam.
MS (ISP): 557.2 (M+H)$^+$.

Example 232

4'-Fluoro-5-methoxy-biphenyl-3-carboxylic acid[1-(3-ethoxy-4-methyl-benzyl)-piperidin-4-yl]-amide The title compound was prepared in analogy to example 229, but using in the reductive amination step 3-ethoxy-4-methyl-benzaldehyde instead of 2,6-diethoxy-4'-fluoro-biphenyl-4-carbaldehyde, as light yellow solid.
MS (ISP): 477.0 (M+H)$^+$.

Example 233

4'-Fluoro-5-methoxy-biphenyl-3-carboxylic acid[1-(4-cyclopropyl-3,5-diethoxy-benzyl)-piperidin-4-yl]-amide The title compound was prepared in analogy to example 229, but using in the reductive amination step 4-cyclopropyl-3,5-diethoxy-benzaldehyde instead of 2,6-diethoxy-4'-fluoro-biphenyl-4-carbaldehyde, as white solid.
MS (ISP): 547.3 (M+H)$^+$.

Example 234

4'-Fluoro-5-methoxy-biphenyl-3-carboxylic acid[1-(3,5-diisopropoxy-benzyl)-piperidin-4-yl]-amide The title compound was prepared in analogy to example 229, but using in the reductive amination step 3,5-diisopropoxy-benzaldehyde instead of 2,6-diethoxy-4'-fluoro-biphenyl-4-carbaldehyde, as off-white foam.
MS (ISP): 535.4 (M+H)$^+$.

Example 235

N-[1-(4-Chloro-3,5-diethoxy-benzyl)-piperidin-4-yl]-5-methoxy-isophthalamic acid methyl ester In analogy to the procedure described in example 50k), 5-methoxy-N-piperidin-4-yl-isophthalamic acid methyl ester (example 143) was reacted with 4-chloro-3,5-diethoxy-benzaldehyde (example 219), sodium cyanoborohydride, N-ethyl-diisopropylamine and acetic acid in ethanol at 50° C. to yield the title compound as off-white solid. MS: 505.2 (MH$^+$).

Example 236

N-[1-(2,6-Diethoxy-4'-fluoro-biphenyl-4-ylmethyl)-piperidin-4-yl]-5-methoxy-isophthalamic acid methyl ester In analogy to the procedure described in example 50k), 5-methoxy-N-piperidin-4-yl-isophthalamic acid methyl ester (example 143) was reacted with 2,6-diethoxy-4'-fluoro-biphenyl-4-carbaldehyde (example 102), sodium cyanoborohydride, N-ethyl-diisopropylamine and acetic acid in ethanol at 50° C. to yield the title compound as off-white solid. MS: 565.3 (MH$^+$).

Example 237

N-[1-(4-Chloro-3,5-diethoxy-benzyl)-piperidin-4-yl]-5-methoxy-isophthalamic acid In analogy to the procedure described in example 53, N-[1-(4-chloro-3,5-diethoxy-benzyl)-piperidin-4-yl]-5-methoxy-isophthalamic acid methyl ester (example 235) was saponified to yield the title compound as colorless solid. MS: 489.3 [(M–H)$^-$].

Example 238

N-[1-(2,6-Diethoxy-4'-fluoro-biphenyl-4-ylmethyl)-piperidin-4-yl]-5-methoxy-isophthalamic acid In analogy to the procedure described in example 53, N-[1-(2,6-diethoxy-4'-fluoro-biphenyl-4-ylmethyl)-piperidin-4-yl]-5-methoxy-isophthalamic acid methyl ester (example 236) was saponified to yield the title compound as off-white solid. MS: 549.3 [(M–H)$^-$].

Example 239

N-[1-(4-Chloro-3,5-diethoxy-benzyl)-piperidin-4-yl]-6-methylamino-nicotinamide

The title compound was prepared in analogy to example 180, but using in the reductive amination step 4-chloro-3,5- diethoxy-benzaldehyde instead of 4-cyclopropyl-3,5-diethoxy-benzaldehyde, as white crystals.

MS (ISP): 447.1 (M+H)$^+$.

The necessary intermediate 6-Methylamino-N-piperidin-4-yl-nicotinamide could not only be prepared as described in example 103, but more conveniently by the procedure used in example 160 relying on nucleophilic substitution of the chloro-pyridine with methylamine (30% in ethanol). Microwave conditions are in that particular case not necessary.

Example 240

N-[1-(2,6-Diethoxy-3',5'-difluoro-biphenyl-4-ylmethyl)-piperidin-4-yl]-5-methyl-nicotinamide The title compound was prepared in analogy to example 98, but using in the reductive amination step 2,6-diethoxy-3',5'-difluoro-biphenyl-4-carbaldehyde instead of 3,5-diisopropoxy-benzaldehyde, as off-white solid.

MS (ISP): 510.3 (M+H)$^+$.

The necessary intermediate 2,6-Diethoxy-3',5'-difluoro-biphenyl-4-carbaldehyde was prepared as described in example 158, but using for the Suzuki—coupling with 3,5-diethoxy-4-iodo-benzaldehyde 3,5-difluorophenylboronic acid instead of cyclopropyl boronic acid, as light yellow solid.

MS (EI): 306.2 [M]$^+$.

Example 241

N-[1-(3,5-Diisopropoxy-benzyl)-piperidin-4-yl]-3-methoxy-5-pyridin-3-yl-benzamide The title compound was prepared in analogy to example 207, but but starting the reaction sequence with 3-methoxy-5-pyridin-3-yl-benzoic acid instead of 3,5-dimethoxy-benzoic acid, as white foam.

MS (ISP): 518.3 (M+H)$^+$.

The necessary starting material 3-Methoxy-5-pyridin-3-yl-benzoic acid was prepared as described in example 228, but using for the Suzuki—coupling 3-pyridylboronic acid instead of 4-pyridylboronic acid, as white solid.

MS (ISP): 230.4 (M+H)$^+$.

Example 242

N-[1-(3,5-Diethoxy-4-fluoro-benzyl)-piperidin-4-yl]-3-methoxy-5-pyridin-3-yl-benzamide The title compound was prepared in analogy to example 241, but using in the reductive amination step 3,5-diethoxy-4-fluoro-benzaldehyde instead of 3,5-diisopropoxy-benzaldehyde, as white solid.

MS (ISP): 508.4 (M+H)$^+$.

Example 243

N-[1-(2,6-Diethoxy-4'-fluoro-biphenyl-4-ylmethyl)-piperidin-4-yl]-3-methoxy-5-pyridin-3-yl-benzamide The title compound was prepared in analogy to example 241, but using in the reductive amination step 2,6-diethoxy-4'-fluoro-biphenyl-4-carbaldehyde instead of 3,5-diisopropoxy-benzaldehyde, as yellow solid.

MS (ISP): 584.3 (M+H)$^+$.

Example 244

N-[1-(2,6-Diethoxy-4'-trifluoromethoxy-biphenyl-4-ylmethyl)-piperidin-4-yl]-5-methyl-nicotinamide The title compound was prepared in analogy to example 240, but using in the reductive amination step 2,6-diethoxy-4'-trifluoromethoxy-biphenyl-4-carbaldehyde instead of 3,5-diisopropoxy-benzaldehyde, as white solid.

MS (ISP): 558.3 (M+H)$^+$.

The necessary intermediate 2,6-Diethoxy-4'-trifluoromethoxy-biphenyl-4-carbaldehyde was prepared as described in example 158, but using for the Suzuki—coupling with 3,5-diethoxy-4-iodo-benzaldehyde 4-trifluoromethoxyphenylboronic acid instead of cyclopropyl boronic acid, as light yellow solid.

MS (EI): 354.1 [M]$^+$.

Example 245

3-Cyanomethoxy-N-[1-(3,5-diethoxy-4-fluoro-benzyl)-piperidin-4-yl]-5-methoxy-benzamide In analogy to the procedure described in example 50k), 3-cyanomethoxy-5-methoxy-N-piperidin-4-yl-benzamide [prepared by i) reaction of 4-(3-hydroxy-5-methoxy-benzoylamino)-piperidine-1-carboxylic acid tert-butyl ester (example 168a) with bromo-acetonitrile in MeCN at rt in the presence of anhydrous potassium carbonate to give 4-(3-cyanomethoxy-5-methoxy-benzoylamino)-piperidine-1-carboxylic acid tert-butyl ester; ii) Boc cleavage using trifluoro acetic acid (90%) in MeCl$_2$ at rt in analogy to the procedure described in example 50i)] was reacted with 3,5-diethoxy-4-fluoro-benzaldehyde (example 50 g), sodium cyanoborohydride, N-ethyl-diisopropylamine and acetic acid in ethanol at 50° C. to yield the title compound as off-white solid. MS: 486.3 (MH$^+$).

Example 246

N-[1-(4-Chloro-3,5-diethoxy-benzyl)-piperidin-4-yl]-3-cyanomethoxy-5-methoxy-benzamide In analogy to the procedure described in example 50k), 3-cyanomethoxy-5-methoxy-N-piperidin-4-yl-benzamide (example 245) was reacted with 4-chloro-3,5-diethoxy-benzaldehyde (example 219), sodium cyanoborohydride, N-ethyl-diisopropylamine and acetic acid in ethanol at 50° C. to yield the title compound as off-white solid. MS: 502.2 (MH$^+$).

Example 247

3-Cyanomethoxy-N-[1-(2,6-diethoxy-4'-fluoro-biphenyl-4-ylmethyl)-piperidin-4-yl]-5-methoxy-benzamide In analogy to the procedure described in example 50k), 3-cyanomethoxy-5-methoxy-N-piperidin-4-yl-benzamide (example 245) was reacted with 2,6-diethoxy-4'-fluoro-biphenyl-4-carbaldehyde (example 102), sodium cyanoborohydride, N-ethyl-diisopropylamine and acetic acid in ethanol at 50° C. to yield the title compound as off-white solid. MS: 562.3 (MH$^+$).

Example 248 rac-N-[1-(4-Chloro-3,5-diethoxy-benzyl)-piperidin-4-yl]-3-(2,3-dihydroxy-propoxy)-5-methoxy-benzamide In analogy to the procedure described in example 50k), rac-3-(2,3-dihydroxy-propoxy)-5-methoxy-N-piperidin-4-yl-benzamide hydrochloride (prepared from rac-4-[3-(2,2-dimethyl-[dioxolan-4-ylmethoxy)-5-methoxy-benzoylamino]-piperidine-1-carboxylic acid tert-butyl ester (example 175a) by reaction with HCl/dioxane in EtOH in analogy to the procedure described in example 250b)] was reacted with 4-chloro-3,5-diethoxy-benzaldehyde (example 219), sodium cyanoborohydride, N-ethyl-diisopropylamine and acetic acid in ethanol at 50° C. to yield the title compound as light brown solid. MS: 537.4 (MH$^+$).

Example 249 rac-N-[1-(2,6-Diethoxy-4'-fluoro-biphenyl-4-ylmethyl)-piperidin-4-yl]-3-(2,3-dihydroxy-propoxy)-5-methoxy-benzamide In analogy to the procedure described in example 50k), rac-3-(2,3-dihydroxy-propoxy)-5-methoxy-N-piperidin-4-yl-benzamide hydrochloride (example 248) was reacted with 2,6-diethoxy-4'-fluoro-biphenyl-4-carbaldehyde (example 102), sodium cyanoborohydride, N-ethyl-diisopropylamine and acetic acid in ethanol at 50° C. to yield the title compound as colorless solid. MS: 597.3 (MH$^+$).

Example 250

3-Carbamoylmethoxy-N-[1-(3,5-diethoxy-4-fluoro-benzyl)-piperidin-4-yl]-5-methoxy-benzamide 4-(3-Carbamoylmethoxy-5-methoxy-benzoylamino)-piperidine-1-carboxylic acid tert-butyl ester 2.10 g (5.4 mmol) of 4-(3-cyanomethoxy-5-methoxy-benzoylamino)-piperidine-1-carboxylic acid tert-butyl ester (example 245) and 0.15 g (1.1 mmol) of potassium carbonate were suspended under argon in 10 mL of DMSO at rt; while stirring, 0.93 mL (1.05 g=2.0 eq.) of hydrogen peroxide solution (35% in water) was added below 25° C. and stirring continued at ambient temperature for 24 hours. Then, the reaction mixture was poured into crashed ice and extracted three times with MeCl$_2$/2-propanol (4:1); the organic phases were evaporated i.V. to yield 2.26 g of the crude title compound as colorless solid. MS: 408.1 (MH$^+$).

3-Carbamoylmethoxy-5-methoxy-N-piperidin-4-yl-benzamide hydrochloride and [3-methoxy-5-(piperidin-4-ylcarbamoyl)-phenoxy]-acetic acid ethyl ester hydrochloride 2.20 g (5.4 mmol) of 4-(3-carbamoylmethoxy-5-methoxy-benzoylamino)-piperidine-1-carboxylic acid tert-butyl ester was suspended under argon in 40 mL of EtOH at rt; while stirring, 6.75 mL of HCl/dioxane (4 molar) was added; the heterogeneous reaction mixture was heated up to reflux to achieve a clear solution. After cooling down to rt, the solvents were removed by evaporation i.V. and the residue was dried in high vacuum at rt for 5 hours. This crude product was recrystallised from MeCN to yield 1.53 g of 3-carbamoylmethoxy-5-methoxy-N-piperidin-4-yl-benzamide hydrochloride as colorless solid [MS: 308.3 (MH$^+$)]; the mother liquor contained 0.80 g of [3-methoxy-5-(piperidin-4-ylcarbamoyl)-phenoxy]-acetic acid ethyl ester hydrochloride as light yellow amorphous solid. MS: 337.3 (MH$^+$).

3-Carbamoylmethoxy-N-[1-(3,5-diethoxy-4-fluoro-benzyl)-piperidin-4-yl]-5-methoxy-benzamide In analogy to the procedure described in example 50k), 3-carbamoylmethoxy-5-methoxy-N-piperidin-4-yl-benzamide hydrochloride was reacted with 3,5-diethoxy-4-fluoro-benzaldehyde (example 50 g), sodium cyanoborohydride, N-ethyl-diisopropylamine and acetic acid in ethanol at 50° C. to yield the title compound as colorless solid. MS: 504.3 (MH$^+$).

Example 251

3-Carbamoylmethoxy-N-[1-(4-chloro-3,5-diethoxy-benzyl)-piperidin-4-yl]-5-methoxy-benzamide In analogy to the procedure described in example 50k), 3-carbamoylmethoxy-5-methoxy-N-piperidin-4-yl-benzamide hydrochloride (example 250b) was reacted with 4-chloro-3,5-diethoxy-benzaldehyde (example 219), sodium cyanoborohydride, N-ethyl-diisopropylamine and acetic acid in ethanol at 50° C. to yield the title compound as colorless solid. MS: 520.4 (MH$^+$).

Example 252

3-Carbamoylmethoxy-N-[1-(2,6-diethoxy-4'-fluoro-biphenyl-4-ylmethyl)-piperidin-4-yl]-5-methoxy-benzamide In analogy to the procedure described in example 50k), 3-carbamoylmethoxy-5-methoxy-N-piperidin-4-yl-benzamide hydrochloride (example 250b) was reacted with 2,6-diethoxy-4'-fluoro-biphenyl-4-carbaldehyde (example 102), sodium cyanoborohydride, N-ethyl-diisopropylamine and acetic acid in ethanol at 50° C. to yield the title compound as colorless solid. MS: 580.2 (MH$^+$).

Example 253

6-Cyano-N-[1-(2,6-diethoxy-4'-fluoro-biphenyl-4-ylmethyl)-piperidin-4-yl]-5-methyl-nicotinamide The title compound was prepared in analogy to example 153, but using in the reductive amination step 6-cyano-5-methyl-N-piperidin-4-yl-nicotinamide instead of 5-methyl-N-piperidin-4-yl-nicotinamide, as white crystals.

MS (ISP): 517.2 (M+H)$^+$.

The necessary intermediate was prepared as follows:

4-[(5-Methyl-1-oxy-pyridine-3-carbonyl)-amino]-piperidine-1-carboxylic acid tert-butyl ester 4-[(5-Methyl-pyridine-3-carbonyl)-amino]-piperidine-1-carboxylic acid tert-butyl ester (1.620 g, 5.07 mmol, intermediate of example 98) was dissolved in 42 ml of abs. CH$_2$Cl$_2$, treated with MCPBA (1.313 g (70%), 1.05 eq.), and kept for 1 h at ambient temperature. Sodium pyrosulfite (0.20 g) and potassium carbonate (2 g) was added, the mixture diluted with CH$_2$Cl$_2$, dried over magnesium sulfate, and evaporated i.V. Flash chromatography (silica gel, CH$_2$Cl$_2$/MeOH=93/7) afforded finally 1.264 g of the title compound as white foam.

MS (ISP): 336.5 [M+H]$^+$, 280.3 [M-tBu+H]$^+$.

4-[(6-Cyano-5-methyl-pyridine-3-carbonyl)-amino]-piperidine-1-carboxylic acid tert-butyl ester To the above prepared 4-[(5-methyl-1-oxy-pyridine-3-carbonyl)-amino]-piperidine-1-carboxylic acid tert-butyl ester (1.263 g, 3.77 mmol), dissolved in 8 ml of 1,2-dimethoxyethane, was added trimethylsilyl cyanide (0.71 ml, 1.5 eq.) and dimethylcarbamoyl chloride (0.52 ml, 1.5 eq.), and the mixture was allowed to react for 60 Min. at 90° C. Pouring onto crashed ice/NaHCO$_3$-solution, twofold extraction with AcOEt, washing with water and brine, drying over magnesium sulfate, and evaporation i. V., followed by flash chromatography (silica gel, CH$_2$Cl$_2$/MeOH=96/4) and crystallization from hexane/AcOEt, afforded 0.668 g of the title compound as white crystals. The mother liquor contained some 2-cyano-regioisomer.
MS (ISP): 345.1 [M+H]$^+$, 362.1 [M+NH$_4$]$^+$.

6-Cyano-5-methyl-N-piperidin-4-yl-nicotinamide

To the above prepared 4-[(6-cyano-5-methyl-pyridine-3-carbonyl)-amino]-piperidine-1-carboxylic acid tert-butyl ester (0.363 g, 1.05 mmol), dissolved in 3 ml of dioxane, was added 5.27 ml of 4N HCl (dioxane) and the resulting suspension stirred at ambient temperature for another h. Careful evaporation left 0.375 g of the title compound as hydrochloride as off-white crystals.
MS (ISP): 245.3 (M+H)$^+$.

Example 254

N-[1-(4-Chloro-3,5-diethoxy-benzyl)-piperidin-4-yl]-6-cyano-5-methyl-nicotinamide The title compound was prepared in analogy to example 253, but using in the reductive amination step 4-chloro-3,5-diethoxy-benzaldehyde instead of 2,6-diethoxy-4'-fluoro-biphenyl-4-carbaldehyde, as white crystals.
MS (ISP): 457.3 (M+H)$^+$.

Example 255

6-Cyano-N-[1-(3,5-diethoxy-4-fluoro-benzyl)-piperidin-4-yl]-5-methyl-nicotinamide The title compound was prepared in analogy to example 253, but using in the reductive amination step 3,5-diethoxy-4-fluoro-benzaldehyde instead of 2,6-diethoxy-4'-fluoro-biphenyl-4-carbaldehyde, as white crystals.
MS (ISP): 441.4 (M+H)$^+$.

Example 256

6-Chloro-N-[1-(2,6-diethoxy-4'-trifluoromethoxy-biphenyl-4-ylmethyl)-piperidin-4-yl]-nicotinamide The title compound was prepared in analogy to example 150, but using in the reductive amination step 2,6-diethoxy-4'-trifluoromethoxy-biphenyl-4-carbaldehyde (example 244) instead of 3,5-diisopropoxy-benzaldehyde, as white crystals.
MS (ISP): 578.3 (M+H)$^+$.

Example 257

N-[1-(3,5-Diethoxy-4-fluoro-benzyl)-piperidin-4-yl]-3-hydroxy-5-methoxy-benzamide In analogy to the procedure described in example 50k), 3-hydroxy-5-methoxy-N-piperidin-4-yl-benzamide hydrochloride [prepared from 4-(3-hydroxy-5-methoxy-benzoylamino)-piperidine-1-carboxylic acid tert-butyl ester (example 168a) by Boc cleavage using HCl/dioxane in EtOH at rt in analogy to the procedure described in example 250b)] was reacted with 3,5-diethoxy-4-fluoro-benzaldehyde (example 50 g), sodium cyanoborohydride, N-ethyl-diisopropylamine and acetic acid in ethanol at 50° C. to yield the title compound as colorless solid. MS: 447.2 (MH$^+$).

Example 258

N-[1-(4-Chloro-3,5-diethoxy-benzyl)-piperidin-4-yl]-3-hydroxy-5-methoxy-benzamide In analogy to the procedure described in example 50k), 3-hydroxy-5-methoxy-N-piperidin-4-yl-benzamide hydrochloride (example 257) was reacted with 4-chloro-3,5-diethoxy-benzaldehyde (example 219), sodium cyanoborohydride, N-ethyl-diisopropylamine and acetic acid in ethanol at 50° C. to yield the title compound as colorless amorphous solid. MS: 463.3 (MH$^+$).

Example 259

N-[1-(2,6-Diethoxy-4'-fluoro-biphenyl-4-ylmethyl)-piperidin-4-yl]-3-hydroxy-5-methoxy-benzamide In analogy to the procedure described in example 50k), 3-hydroxy-5-methoxy-N-piperidin-4-yl-benzamide hydrochloride (example 257) was reacted with 2,6-diethoxy-4'-fluoro-biphenyl-4-carbaldehyde (example 102), sodium cyanoborohydride, N-ethyl-diisopropylamine and acetic acid in ethanol at 50° C. to yield the title compound as colorless amorphous solid. MS: 523.3 (MH$^+$).

Example 260

Methanesulfonic acid 3-[1-(3,5-diethoxy-4-fluoro-benzyl)-piperidin-4-ylcarbamoyl]-5-methoxy-phenyl ester In analogy to the procedure described in example 72a), N-[1-(3,5-diethoxy-4-fluoro-benzyl)-piperidin-4-yl]-3-hydroxy-5-methoxy-benzamide (example 257) was reacted with methanesulfonyl chloride, N-ethyl-diisopropylamine in CH$_2$Cl$_2$ at rt to yield the title compound as colorless solid. MS: 525.2 (MH$^+$).

Example 261

Methanesulfonic acid 3-[1-(4-chloro-3,5-diethoxy-benzyl)-piperidin-4-ylcarbamoyl]-5-methoxy-phenyl ester In analogy to the procedure described in example 72a), N-[1-(4-chloro-3,5-diethoxy-benzyl)-piperidin-4-yl]-3-hydroxy-5-methoxy-benzamide (example 258) was reacted with methanesulfonyl chloride, N-ethyl-diisopropylamine in CH$_2$Cl$_2$ at rt to yield the title compound as colorless solid. MS: 541.2 (MH$^+$).

Example 262

Methanesulfonic acid 3-[1-(2,6-diethoxy-4'-fluoro-biphenyl-4-ylmethyl)-piperidin-4-ylcarbamoyl]-5-methoxy-phenyl ester In analogy to the procedure described in example 72a), N-[1-(2,6-diethoxy-4'-fluoro-biphenyl-4-ylmethyl)-piperidin-4-yl]-3-hydroxy-5-methoxy-benzamide (example 259) was reacted with methanesulfonyl chloride, N-ethyl-diisopropylamine in CH$_2$Cl$_2$ at rt to yield the title compound as colorless solid. MS: 601.3 (MH$^+$).

Example 263

{3-[1-(2,6-Diethoxy-4'-fluoro-biphenyl-4-ylmethyl)-piperidin-4-ylcarbamoyl]-5-methoxy-phenoxy}-acetic acid ethyl ester In analogy to the procedure described in example 50k), [3-methoxy-5-(piperidin-4-ylcarbamoyl)-phenoxy]-acetic acid ethyl ester hydrochloride (example 250b) was reacted with 2,6-diethoxy-4'-fluoro-biphenyl-4-carbaldehyde (example 102), sodium cyanoborohydride, N-ethyl-diisopropylamine and acetic acid in ethanol at 50° C. to yield the title compound as colorless solid. MS: 609.3 (MH$^+$).

Example 264

{3-[1-(4-Chloro-3,5-diethoxy-benzyl)-piperidin-4-ylcarbamoyl]-5-methoxy-phenoxy}-acetic acid ethyl ester In analogy to the procedure described in example 50k), [3-methoxy-5-(piperidin-4-ylcarbamoyl)-phenoxy]-acetic acid ethyl ester hydrochloride (example 250b) was reacted with 4-chloro-3,5-diethoxy-benzaldehyde (example 219), sodium cyanoborohydride, N-ethyl-diisopropylamine and acetic acid in ethanol at 50° C. to yield the title compound as light yellow oil. MS: 549.3 (MH$^+$).

Example 265

{3-[1-(2,6-Diethoxy-4'-fluoro-biphenyl-4-ylmethyl)-piperidin-4-ylcarbamoyl]-5-methoxy-phenoxy}-acetic acid In analogy to the procedure described in example 53, {3-[1-(2,6-diethoxy-4'-fluoro-biphenyl-4-ylmethyl)-piperidin-4-ylcarbamoyl]-5-methoxy-phenoxy}-acetic acid ethyl ester (example 263) was saponified to yield the title compound as off-white solid. MS: 579.2 [(M−H)$^-$].

Example 266

{3-[1-(4-Chloro-3,5-diethoxy-benzyl)-piperidin-4-ylcarbamoyl]-5-methoxy-phenoxy}-acetic acid In analogy to the procedure described in example 53, {3-[1-(4-chloro-3,5-diethoxy-benzyl)-piperidin-4-ylcarbamoyl]-5-methoxy-phenoxy}-acetic acid ethyl ester (example 264) was saponified to yield the title compound as colorless solid. MS: 519.3 [(M−H)$^-$].

Example 267

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example 268

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 269

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example 270

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated soya bean oil | 8.0 mg |
| Partially hydrogenated plant oils | 34.0 mg |
| Soya bean oil | 110.0 mg |
| Weight of capsule contents | 165.0 mg |

-continued

| Gelatin capsule | |
|---|---|
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 271

Sachets containing the following ingredients can be manufactured in a conventional manner:

| Compound of formula (I) | 50.0 mg |
|---|---|
| Lactose, fine powder | 1015.0 mg |
| Microcristalline cellulose (AVICEL PH102) | 1400.0 mg |
| Sodium carboxymethyl cellulose | 14.0 mg |
| Polyvinylpyrrolidone K30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidone in water. The granulate is mixed with magnesiumstearate and the flavouring additives and filled into sachets.

\* \* \*

It is to be understood that the invention is not limited to the particular embodiments of the invention described above, as variations of the particular embodiments may be made and still fall within the scope of the appended claims.

The invention claimed is:

1. A compound of the formula I:

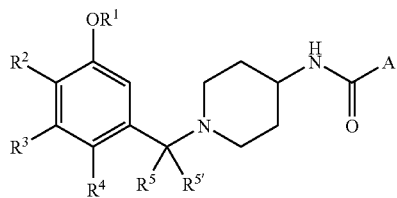

wherein
$R^1$ is selected from the group consisting of ethyl, 2-fluoroethyl, isopropyl and isobutyl;
$R^2$ is phenyl, phenyl substituted by one to three substituents selected from the group consisting of halogen, halogen-$C_{1-7}$-alkyl and halogen-$C_{1-7}$-alkoxy, imidazolyl and pyrrolyl;

$R^3$ is selected from the group consisting of hydrogen, $C_{1-7}$-alkoxy, amino, —NH—C(O)-$R^8$, wherein $R^8$ is $C_{1-7}$-alkyl, —O-benzyl and —O-tetrahydropyranyl;
or $R^2$ and $R^3$ are bonded to each other to form a ring together with the carbon atoms they are attached to and $R^2$ and $R^3$ together are —CH=CH—NH—;
$R^4$ is selected from the group consisting of hydrogen, halogen, pyridyl and pyrimidyl;
$R^5$ and $R^{5'}$ independently from each other are selected from hydrogen or methyl;
A is pyridyl or pyridyl substituted by one or two substituents selected from the group consisting of $C_{1-7}$alkyl, amino, $C_{1-7}$alkylamino, cyano and halogen;
and pharmaceutically acceptable salts thereof.

2. The compound according to claim 1, wherein $R^2$ is phenyl substituted by one to three substituents selected from the group consisting of halogen, halogen-$C_{1-7}$-alkyl and halogen-$C_{1-7}$-alkoxy.

3. The compound according to claim 1, wherein $R^3$ and $R^4$ are hydrogen.

4. The compound according to claim 1, wherein $R^3$ is $C_{1-7}$-alkoxy or —O-tetrahydropyranyl.

5. The compound according to claim 1, wherein $R^4$ is pyridyl or pyrimidyl.

6. The compound according to claim 5, wherein $R^3$ is hydrogen.

7. The compound according to claim 1, wherein $R^5$ and $R^{5'}$ are hydrogen.

8. The compound according to claim 1, wherein $R^1$ is ethyl.

9. The compound according to claim 1, selected from the group consisting of:
N-[1-(2-ethoxy-4'-fluoro-biphenyl-4-ylmethyl)-piperidin-4-yl]-5-methyl-nicotinamide,
N-[1-(2-ethoxy-4'-fluoro-biphenyl-4-ylmethyl)-piperidin-4-yl]-6-methylamino-nicotinamide,
N-[1-(3,5-diethoxy-4-imidazol-1-yl-benzyl)-piperidin-4-yl]-5-methyl-nicotinamide,
N-[1-(2,6-diethoxy-4'-fluoro-biphenyl-4-ylmethyl)-piperidin-4-yl]-6-methylamino-nicotinamide,
N-[1-(2,6-diethoxy-4'-fluoro-biphenyl-4-ylmethyl)-piperidin-4-yl]-5-methyl-nicotinamide,
6-chloro-N-[1-(2,6-diethoxy-4'-fluoro-biphenyl-4-ylmethyl)-piperidin-4-yl]-nicotinamide,
6-amino-N-[1-(2,6-diethoxy-4'-fluoro-biphenyl-4-ylmethyl)-piperidin-4-yl]-nicotinamide,
N-[1-(2,6-diethoxy-4'-fluoro-biphenyl-4-ylmethyl)-piperidin-4-yl]-6-isopropylamino-nicotinamide,
N-[1-(2,6-diethoxy-3',5'-difluoro-biphenyl-4-ylmethyl)-piperidin-4-yl]-5-methyl-nicotinamide,
6-cyano-N-[1-(2,6-diethoxy-4'-fluoro-biphenyl-4-ylmethyl)-piperidin-4-yl]-5-methyl-nicotinamide,
and pharmaceutically acceptable salts thereof.

10. A pharmaceutical composition, comprising a therapeutically effective amount of a compound according to claim 1 as well as a pharmaceutically acceptable carrier and/or adjuvant.

\* \* \* \* \*